United States Patent [19]

Dhanoa et al.

[11] Patent Number: 5,374,638

[45] Date of Patent: Dec. 20, 1994

[54] SIX MEMBERED RING FUSED IMIDAZOLES SUBSTITUTED WITH PHENOXYPHENYLACETIC ACID DERIVATIVES USED TO TREAT ASTHMA

[75] Inventors: Daljit S. Dhanoa, Secaucus; Kenneth J. Fitch, Scotch Plains, both of N.J.; Daniel F. Veber, Ambler, Pa.; Thomas F. Walsh, Westfield, N.J.; David L. Williams, Jr., Telford, Pa.

[73] Assignee: Merck & Co., Inc., Rahway, N.J.

[21] Appl. No.: 34,456

[22] Filed: Mar. 19, 1993

[51] Int. Cl.$^5$ ............ A61K 31/445; A61K 31/41
[52] U.S. Cl. .................... 514/326; 514/319; 514/323; 514/327; 514/381; 514/826; 514/405; 514/410; 514/413; 514/303
[58] Field of Search ............ 514/326, 381, 323, 382, 514/387, 388, 826

[56] References Cited

U.S. PATENT DOCUMENTS

| | | | |
|---|---|---|---|
| 5,070,086 | 12/1991 | Friary | 514/183 |
| 5,082,838 | 1/1992 | Naka et al. | |
| 5,114,918 | 5/1992 | Ishikawa et al. | |
| 5,187,195 | 2/1993 | Oohata et al. | |
| 5,200,422 | 4/1993 | Olesen | 514/387 |
| 5,240,938 | 8/1993 | Greenlee et al. | 514/303 |

FOREIGN PATENT DOCUMENTS

| | | |
|---|---|---|
| 0436189A1 | 7/1990 | European Pat. Off. |
| 0457195A2 | 11/1991 | European Pat. Off. |
| 0460679A2 | 12/1991 | European Pat. Off. |
| 0496452A1 | 7/1992 | European Pat. Off. |
| 0510526A1 | 10/1992 | European Pat. Off. |
| 0526642A1 | 2/1993 | European Pat. Off. |
| 0526708A1 | 2/1993 | European Pat. Off. |
| WO92/15321 | 9/1992 | WIPO |
| WO92/20706 | 11/1992 | WIPO |

OTHER PUBLICATIONS

K. Noguchi, et al., European Journal of Pharmacology 233, pp. 47–51 (1993).
J. G. Filep, et al., European Journal of Pharmacology 239, pp. 231–236 (1993).
T. Masaki, et al., Medicinal Research Reviews, 12, No. 4, pp. 391–421 (1992).
Burger; Medicinal Chemistry, published by Wiley-Interscience, New York, N.Y.–(1971) p. 77.
07/744,557, 08001991, Greenlee, W. J. et al.

Primary Examiner—Marianne M. Cinthins
Assistant Examiner—T. J. Criares
Attorney, Agent, or Firm—Valerie J. Camara; Mark R. Daniel; Joseph F. DiPrima

[57] ABSTRACT

Phenoxyphenylacetic acids and derivatives of general structural formula I

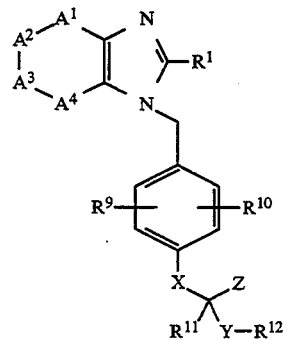

have endothelin antagonist activity and are therefore useful in treating cardiovascular disorders, such as hypertension, congestive heart failure, postischemic renal failure, vasospasm, cerebral and cardiac ischemia, myocardial infarction, inflammatory diseases, Raynaud's disease, and endotoxic shock, and asthma.

6 Claims, No Drawings

SIX MEMBERED RING FUSED IMIDAZOLES SUBSTITUTED WITH PHENOXYPHENYLACETIC ACID DERIVATIVES USED TO TREAT ASTHMA

SUMMARY OF THE INVENTION

This invention is concerned with non-peptidic endothelin receptor antagonists and their method of use. The compounds of the present invention are therapeutic agents particularly useful for the treatment of asthma, hypertension, pulmonary hypertension, arteriosclerosis, congestive heart failure, renal failure, particularly post-ischemic renal failure, cyclosporin nephrotoxicity, vasospasm, vascular restenosis, cerebral and cardiac ischemia and other ischemic states, myocardial infarction, Raynaud's disease, inflammatory bowel diseases, including Crohn's disease and ulcerative colitis, as well as other inflammatory diseases, or endotoxic shock caused by or associated with endothelin.

BACKGROUND OF THE INVENTION

Endothelin is a 21-amino acid peptide produced by endothelial cells. The peptide is secreted not only by endothelial cells but also by tracheal epithelial cells or from kidney cells. Endothelin (ET-1) has a potent vasoconstrictor effect. The vasoconstricting effect is caused by the binding of endothelin to its receptor on the vascular smooth muscle cells.[1-3]

Endothelin-1 (ET-1 ) is one of three recently identified potent vasoconstricting peptides which also includes endothelin-2 (ET-2) and endothelin-3 (ET-3) which differ from ET-1 by two and six amino acids, respectively.[4]

Increased levels of endothelin are found in the blood of patients with essential hypertension, acute myocardial infarction, pulmonary hypertension, Raynaud's disease or atherosclerosis or in the washing fluids of the respiratory tract of patients with asthma compared to normal levels.[5-8]

An experimental model of cerebral vasospasm and a second model of acute renal failure have led to the conclusion that endothelin is one of the mediators causing cerebral vasospasm following a subarachnoid hemorrhage, and renal failure.[9-10]

Endothelin was also found to control the release of many physiological substances such as renin, atrial natriuretic peptide, endothelium-derived relaxing factor (EDRF), thromboxane $A_2$,[14] prostacyclin, norepinephrine, angiotensin II and substance P.[11-16] Further, endothelin causes contraction of the smooth muscle of the gastrointestinal tract and the uterine smooth muscle.[1,7-19] Endothelin has also been shown to promote the growth of rat vascular smooth muscle cells which would suggest a possible relevance to arterial hypertrophy.[20]

Endothelin receptors are present in high concentration in the peripheral tissues and also in the central nervous system, and cerebral administration of endothelin has been shown to induce behavioral changes in animals, suggesting that endothelin may play an important role in controlling neural functions.[21]

Endotoxin has been shown to promote the release of endothelin. This finding has suggested that endothelin is an important mediator for endotoxin-induced diseases.[22-23]

A study has shown that cyclosporin added to a renal cell culture, increased endothelin secretion.[24] Another study has shown that administration of cyclosporin to rats led to a decrease in the glomerular filtration rate and an increase in the blood pressure, in association with a remarkable increase in the circulating endothelin level. This cyclosporin-induced renal failure can be suppressed by the administration of anti-endothelin antibody.[25] These studies suggest that endothelin is significantly involved in the pathogenesis of cyclosporin-induced renal disease.

A recent study in patients with congestive heart failure demonstrated a good correlation between the elevated levels of endothelin in the plasma and the severity of the disease.[26]

Substances which specifically inhibit the binding of endothelin to its receptor are believed to block the physiological effects of endothelin and would be useful in treating patients with endothelin related disorders. The present invention discloses potent non-peptidic endothelin antagonists.

Endothelin is an endogenous substance which directly or indirectly (through the controlled release of various other endogenous substances) induces sustained contraction of vascular or non-vascular smooth muscles. Its excess production or excess secretion is believed to be one of the factors responsible for hypertension, pulmonary hypertension, Raynaud's disease, bronchial asthma, acute renal failure, myocardial infarction, angina pectoris, arteriosclerosis, cerebral vasospasm and cerebral infarction.

The novel compounds of the present invention are useful as non-peptidic endothelin antagonists, and have not been disclosed in any issued patents or patent applications. Fujisawa in European Patent Application EP 457,195, Banyu in EP 436,189 and 460,679, and Takeda in Patent Cooperation Treaty International Publication No. WO 91/13089 have applications disclosing linear and cyclic peptidic compounds as endothelin antagonists. Fujisawa has also disclosed anthraquinone derivatives produced by a fermentation process using Streptomyces sp. No. 89009 in EP 405,421.

A Roussel-Uclaf European Patent Application (EP 498,723) disclosed a series of substituted (1,4-quinolinoxy)methylbiphenylcarboxylic acids as both endothelin antagonists and angiotensin II antagonists. A patent from Hoffmann-La Roche (EP 510,526) has also appeared claiming the endothelin antagonist properties of a series of N-(4-pyrimidinyl)benzenesulfonamides.

REFERENCES

1 Nature, 332, 411–415 (1988).
2 FEBS Letters, 231, 440–444 (1988).
3 Biochem. Biophys. Res. Commun. 154, 868–875 (1988).
4 TIPS, 13, 103–108, March, 1992.
5 Japan J. Hypertension 12, 79 (1989).
6 J. Vascular Medicine Biology, 2, 207 (1990).
7 J. Am. Med. Association, 264, 2868 (1990).
8 The Lancet, ii, 207 (1990) and The Lancet, ii, 747–748 (1989).
9 Japan. Soc. Cereb. Blood Flow & Metabol. 1, 73 (1989).
10 J. Clin. Invest., 83, 1762–1767 (1989).
11 Biochem. Biophys. Res. Comm. 157, 1164–1168 (1988).
12 Biochem. Biophys. Res. Comm. 155, 167–172 (1989).
13 Proc. Natl. Acad. Sci. USA, 85, 9797–9800 (1989).
14 J. Cardiovasc. Pharmacol., 13, 589–592 (1989).
15 Japan. J. Hypertension 12, 76 (1989).
16 Neuroscience Letters, 102, 179–184 (1989).

17 FEBS Letters, 247, 337–340 (1989).
18 Eur. J. Pharmacol. 154, 227–228 (1988).
19 Biochem. Biophys. Res. Commun., 159, 317–323 (1989).
20 Atherosclerosis, 78, 225–228 (1989).
21 Neuroscience Letters, 97, 276–279 (1989).
22 Biochem. Biophys. Res. Commun. 161, 1220–1227 (1989).
23 Acta. Physiol. Scand., 137, 317–318 (1989).
24 Eur. J. Pharmacol., 180, 191–192 (1990).
25 Kidney Int. 37, 1487–1491 (1990).
26 Mayo Clinic Proc., 67, 719–724 (1992).

DETAILED DESCRIPTION OF THE INVENTION

This invention relates to compounds of the general Formula I useful in this novel method of treatment:

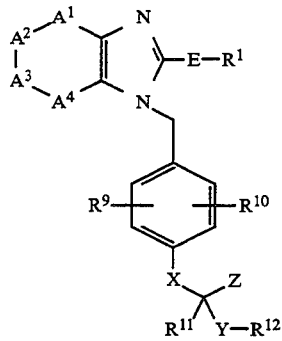

or a pharmaceutically acceptable salt thereof wherein:

$R^1$ is:

(a) $(C_1-C_6)$-alkyl, $(C_2-C_6)$-alkenyl or $(C_2-C_6)$-alkynyl each of which is unsubstituted or substituted with a substituent selected from the group consisting of:
  i) phenyl or naphthyl as defined in $R^1$(b),
  ii) $(C_3-C_7)$-cycloalkyl,
  iii) Cl, Br, I, F,
  iv) OH,
  v) $NH_2$,
  vi) $NH(C_1-C_4)$-alkyl,
  vii) $N[(C_1-C_4)$-alkyl$]_2$,
  viii) $NHSO_2R^2$,
  ix) $CF_3$,
  x) $COOR^2$, or
  xi) $SO_2NHR^{2a}$; and (b) phenyl or naphthyl which is unsubstituted, mono- or disubstituted with substituents selected from the group consisting of:
  i) Cl, Br, I, F,
  ii) $(C_1-C_4)$-alkyl,
  iii) $(C_1-C_4)$-alkoxy,
  iv) $NO_2$,
  v) $CF_3$,
  vi) $SO_2NR^{2a}R^{2a}$,
  vii) $(C_1-C_4)$-alkylthio,
  viii) hydroxy,
  ix) amino,
  x) $(C_3-C_7)$-cycloalkyl,
  xi) $(C_3-C_{10})$-alkenyl; and (c) heteroaryl, wherein heteroaryl is defined as a 5- or 6-membered heteroaromatic moiety selected from the group consisting of thiophene, furan, oxazole, pyridine or pyrimidine, which is unsubstituted, mono- or disubstituted with substituents selected frown the group consisting of:
  i) Cl, Br, I, F,
  ii) OH,
  iii) SH,
  iv) $NO_2$,
  v) $(C_1-C_4)$-alkyl,
  vi) $(C_2-C_4)$-alkenyl,
  vii) $(C_2-C_4)$-alkynyl,
  viii) $(C_1-C_4)$-alkoxy, or
  ix) $CF_3$, or (d) $(C_1-C_4)$-perfluoroalkyl; and $—A^1—A^2—A^3—A^4—$ is:

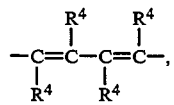 (a)

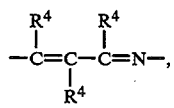 (b)

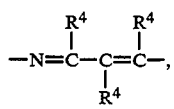 (c)

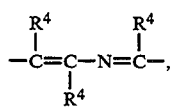 (d)

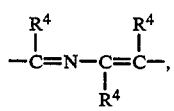 (e)

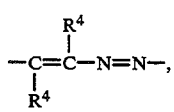 (f)

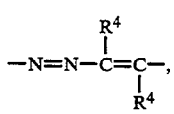 (g)

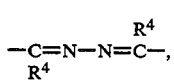 (h)

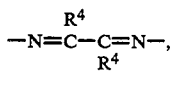 (i)

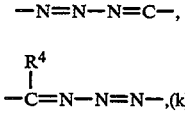 (j)

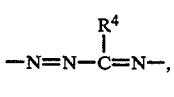(k)

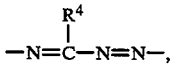 (l)

 (m)

-continued
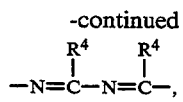 (n)
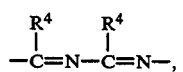 (o)
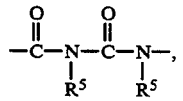 (p)
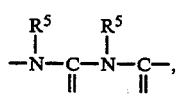 (q)
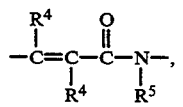 (r)
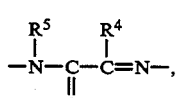 (s)
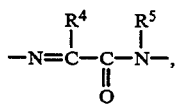 (t)
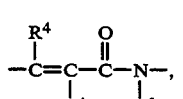 (u)
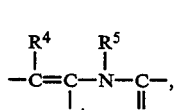 (v)
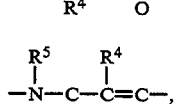 (w)
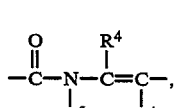 (x)
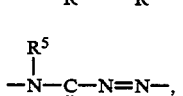 (y)
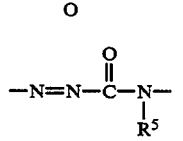 (z)
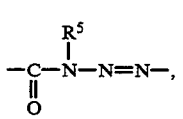 (aa)
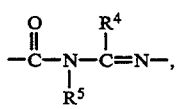 (ab)
-continued
 (ac)
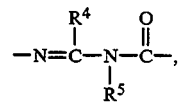 (ad)
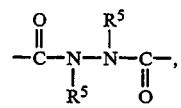 (ae)
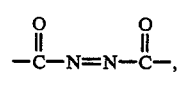 (af)
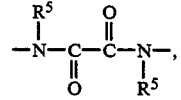 (ag)
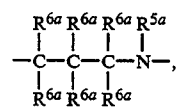 (ah)
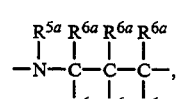 (ai)
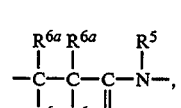 (aj)
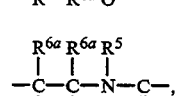 (ak)
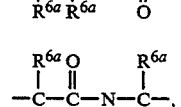 (al)
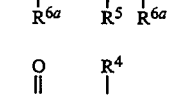 (am)
or
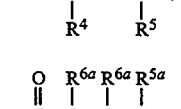 (an)
E is:
(a) a single bond,
(b) —S(O)$_n$(CH$_2$)$_s$—, or
(c) —O—; and
n is 0 to 2; and
s is 0 to 5; and
R$^2$ is:
(a) H, or
(b) (C$_1$–C$_6$)-alkyl; and $R^{2a}$ is:
(a) $R^2$,
(b) $CH_2$-aryl, or
(c) aryl; and $R^4$ groups are independently:
(a) H,
(b) $(C_1-C_6)$-alkyl, $(C_2-C_6)$-alkenyl, or $(C_2-C_6)$-alkynyl, each of which is unsubstituted or substituted with:
  i) OH,
  ii) $(C_1-C_4)$-alkoxy,
  iii) $CO_2R^2$,
  iv) $OCOR^2$,
  v) $CONHR^{2a}$,
  vi) $CON(R^{2a})_2$,
  vii) $N(R^{2a})C(=O)R^2$,
  viii) $NH_2$,
  ix) $(C_1-C_4)$-alkylamino,
  x) di[$(C_1-C_4)$-alkyl]amino,
  xi) $-S-(C_1-C_4)$-alkyl,
  xii) aryl,
  xiii) heteroaryl,
(c) Cl, Br, I, F,
(d) $CF_3$,
(e) $CO_2R^{2a}$,
(f) $C(=O)N(R^{2a})_2$, or
(g) $-C(=O)$-aryl,
(h) $(C_3-C_7)$-cycloalkyl,
(i) $-OR^{22}$,
(j) $-SH$,
(k) $-S(O)_n-(C_1-C_4)$-alkyl,
(l) $-SO_3H$,
(m) $-NR^2R^{15}$
(n) $-NR^2C(=O)R^{15}$,
(o) $-NR^2COOR^{15}$,
(p) $-SO_2NR^{2a}R^{2a}$,
(q) $-NO_2$,
(r) $-NHSO_2-(C_1-C_4)$-alkyl, or
(s) when $R^4$ groups are on adjacent carbon atoms they may join to form a phenyl ring; and $R^5$ is:
(a) H, or
(b) $(C_1-C_6)$-alkyl or $(C_2-C_6)$-alkenyl, optionally substituted with:
  i) hydroxy, or
  ii) $(C_1-C_4)$-alkoxy; and $R^{5a}$ is
(a) $R^5$, or
(b) $(C_1-C_4)$-acyl; and $R^6$ is:
(a) H,
(b) $(C_1-C_6)$-alkyl, or
(c) $(C_1-C_6)$-alkyl substituted with hydroxy; and $R^{6a}$ is:
(a) $R^6$, or
(b) $(C_1-C_6)$-alkyl substituted with:
  i) $CO_2R^2$,
  ii) $CONHR^2$,
  iii) $CON(R^2)_2$; and $R^9$ and $R^{10}$ are independently:
(a) H,
(b) $(C_1-C_6)$-alkyl, unsubstituted or substituted with $(C_3-C_7)$-cycloalkyl,
(c) $(C_2-C_6)$-alkenyl,
(d) $(C_2-C_6)$-alkynyl,
(e) Cl, Br, F, I,
(f) $(C_1-C_6)$-alkoxy,
(g) when $R^9$ and $R^{10}$ are on adjacent carbons, they can be joined to form a phenyl ring,
(h) perfluoro-$(C_1-C_6)$-alkyl,
(i) $(C_3-C_7)$-cycloalkyl, unsubstituted or substituted with $(C_1-C_6)$-alkyl,
(j) aryl,
(k) $(C_1-C_6)$-alkyl-$S(O)_n-(CH_2)_n-$,
(l) hydroxy-$(C_1-C_6)$-alkyl,
(m) $-CF_3$,
(n) $-CO_2R^{2a}$,
(o) $-OH$,
(p) $-NR^2R^{15}$,
(q) $-[(CH_1-C_6)$-alkyl]$NR^2R^{15}$,
(r) $-NO_2$,
(s) $-(CH_2)_n-SO_2-N(R^2)_2$,
(t) $-NR^2CO-(C_1-C_4)$-alkyl, or
(u) $-CON(R^2)_2$;

X is:
(a) $-O-$,
(b) $-S(O)_n-$,
(c) $-NR^{13}-$
(d) $-CH_2O-$,
(e) $-CH_2S(O)_n-$,
(f) $-CH_2NR^{13}-$,
(g) $-OCH_2-$,
(h) $-NR^{13}CH_2-$,
(i) $-S(O)_nCH_2-$, or
(j) single bond;

Y is:
(a) single bond,
(b) $-O-$,
(c) $-S(O)_n-$, or
(d) $-NR^{13}-$; and
except that X and Y are not defined in such a way that the carbon atom to which Z is attached is also simultaneously bonded to two heteroatoms (O, N, S, SO, $SO_2$);

$R^{11}$ and $R^{12}$ are independently:
(a) H,
(b) $(C_1-C_6)$-alkyl, unsubstituted or substituted with a substituent selected from the group consisting of:
  (i) aryl,
  (ii) $(C_3-C_7)$-cycloalkyl,
  (iii) $NR^2R^{15}$,
  (iv) morpholin-4-yl,
  (v) OH,
  (vi) $CO_2R^{2a}$, or
  (vii) $CON(R^2)_2$,
(c) phenyl, naphthyl, phenyl-$(C_1-C_2)$-alkyl, or naphthyl-$(C_1-C_2)$-alkyl, unsubstituted or substituted with 1 to 3 substituents selected from the group consisting of:
  (i) Cl, Br, I, F,
  (ii) $(C_1-C_6)$-alkyl,
  (iii) [$(C_1-C_5)$-alkenyl]$CH_2-$,
  (iv) [$(C_1-C_5)$-alkynyl]$CH_2-$,
  (v) $(C_1-C_6)$-alkyl$-S(O)_n-(CH_2)_n-$,
  (vi) $-CF_3$,
  (vii) $-CO_2R^{2a}$,
  (viii) $-OH$,
  (ix) $-NR^2R^{15}$,
  (x) $-NO_2$,
  (xi) $-NR^2COR^2$,
  (xii) $-CON(R^2)_2$,
  (xiii) $-G^1-[(C_1-C_6)$-alkyl]$-R^{18}$,
  (xiv) $-N[CH_2CH_2]_2Q^1$, or
  (xv) $-P(O)[O-(C_1-C_4)$-alkyl]$_2$, and can additionally be substituted with 1 or 2 substituents selected from the group consisting of: Br, Cl, or F,
  (d) $(C_3-C_7)$-cycloalkyl, or
  (e) when Y is single bond, $R^{11}$ and $R^{12}$ can be joined to form a ring of 5 to 7 carbon atoms, the ring can be benzo-fused and one carbon of which can be replaced with a heteroatom selected from the group consisting of: O, $S(O)_n$ and $NR^{17}$; and $G^1$ is: a single bond, O, $S(O)_n$ or $NR^{18}$; and
$Q^1$ is: O, $S(O)_n$ or $NR^{17}$; and
$R^{13}$ is:
  (a) H,
  (b) $(C_1-C_6)$-alkyl,
  (c) phenyl or naphthyl as defined in $R^1$(b)
  (d) phenyl-$(C_1-C_6)$-alkyl—(C=O)— or naphthyl-$(C_1-C_6)$-alkyl-(C=O)—,
  (e) $(C_1-C_6)$-alkyl-(C=O)—,
  (f) $[(C_2-C_5)$-alkenyl]$CH_2$—,
  (g) $[(C_2-C_5)$-alkynyl]$CH_2$—, or
  (h) phenyl-$CH_2$— or naphthyl-$CH_2$—; and Z is:
  (a) —$CO_2H$,
  (b) —$CO_2R^{19}$,
  (c) -tetrazol-5-yl,
  (d) —CONH(tetrazol-5-yl)
  (e) —$CONHSO_2$-phenyl, or $CONHSO_2$-naphthyl, wherein phenyl or naphthyl is unsubstituted or substituted as defined in $R^1$(b),
  (f) —$CONHSO_2$—$(C_1-C_8)$-alkyl, wherein the alkyl group is unsubstituted or substituted with a substituent selected from the group consisting of: —OH, —SH, —O$(C_1-C_4)$-alkyl, —S—$(C_1-C_4)$-alkyl, —$CF_3$, Cl, Br, F, I, —$NO_2$, —$CO_2H$, —$CO_2$—$(C_1-C_4)$-alkyl, —$NH_2$, NH[$(C_1-C_4)$-alkyl], or —N[$(C_1-C_4)$-alkyl]$_2$,
  (g) —$CONHSO_2$—$(C_1-C_4)$-perfluoroalkyl,
  (h) —$CONHSO_2$-heteroaryl,
  (i) —$CONHSO_2NR^{2a}R^{2a}$,
  (j) —$SO_2NHCO$—phenyl or —$SO_2NH$-CO—naphthyl, wherein phenyl or naphthyl is unsubstituted or substituted as defined in $R^1$(b),
  (k) —$SO_2NHCO$—$(C_1-C_8)$-alkyl, wherein the alkyl group is unsubstituted or substituted with a substituent selected from the group consisting of: —OH, —SH, —O$(C_1-C_4)$-alkyl, —S—$(C_1-C_4)$-alkyl, —$CF_3$, Cl, Br, F, I, —$NO_2$, —$CO_2H$, —$CO_2$—$(C_1-C_4)$-alkyl, —$NH_2$, —NH[$(C_1-C_4)$-alkyl], or —N[$(C_1-C_4)$-alkyl]$_2$,
  (l) —$SO_2NHCO$—$(C_1-C_4)$-perfluoroalkyl,
  (m) —$SO_2NHCO$—heteroaryl,
  (n) —$SO_2CONR^{2a}R^{2a}$,
  (o) —$PO(OH)_2$,
  (p) —$PO(OR^2)_2$, or
  (q) —$PO(OH)(OR^2)$; and $R^{14}$ is:
  (a) H,
  (b) $(C_1-C_6)$-alkyl,
  (c) allyl,
  (d) $(C_3-C_6)$-cycloalkyl,
  (e) $(C_1-C_4)$-acyl,
  (f) benzyl, or
  (g) phenyl; and $R^{15}$ is:
  (a) H, or
  (b) $(C_1-C_4)$-alkyl, unsubstituted or substituted with:
    i) $NH_2$,
    ii) NH[$(C_1-C_4)$-alkyl],
    iii) N[$(C_1-C_4)$-alkyl]$_2$,
    iv) $CO_2H$,
    v) $CO_2(C_1-C_4)$-alkyl,
    vi) OH,
    vii) $SO_3H$, or
    viii) $SO_2NH_2$; and $R^{16}$ is:
  (a) H,
  (b) $(C_1-C_6)$-alkyl,
  (c) phenyl or naphthyl,
  (d) phenyl-$(C_1-C_5)$-alkyl or naphthyl-$(C_1-C_5)$-alkyl; and $R^{17}$ is:
  (a) H,
  (b) $(C_1-C_4)$-alkyl,
  (c) $(C_1-C_4)$-alkoxyl,
  (d) phenyl or naphthyl,
  (e) phenyl-$(C_1-C_4)$-alkyl or naphthyl-$(C_1-C_4)$-alkyl,
  (f) $CO_2R^{2a}$,
  (g) $CON(R^2)_2$,
  (h) $SO_2R^{2a}$,
  (i) $SO_2N(R^2)_2$,
  (j) $P(O)[(C_1-C_4)$-alkoxyl]$_2$, or
  (k) imidazol-2-yl or imidazol-4-yl, in which the imidazolyl can be substituted with $(C_1-C_4)$-alkyl; and $R^{18}$ is:
  (a) OH,
  (b) $NR^2R^{15}$,
  (c) $CO_2R^{2a}$,
  (d) $CON(R^2)_2$,
  (e) $S(O)_n$—$(C_1-C_4)$-alkyl,
  (f) $N(CH_2CH_2)_2Q'$; and $R^{19}$ is:
  (a) $(C_1-C_4)$-alkyl,
  (b) $CHR^{20}$—O—$COR^{21}$,
  (c) $CH_2CH_2$—N[$(C_1-C_2)$-alkyl]$_2$,
  (d) $CH_2CH_2$—N[$(CH_2-CH_2)_2$O],
  (e) $(CH_2CH_2O)_y$—O—[$(C_1-C_4)$-alkyl], wherein y is 1 or 2,
  (f) phenyl, naphthyl, $CH_2$—phenyl or $CH_2$-naphthyl, where phenyl or naphthyl is optionally substituted with $CO_2$—$(C_1-C_4)$-alkyl,

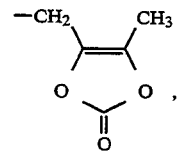

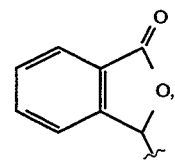

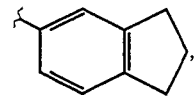

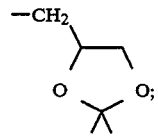

$R^{20}$ and $R^{21}$ independently are $(C_1-C_6)$-alkyl or phenyl; and $R^{22}$ groups are independently:
 (a) H,
 (b) $(C_1-C_6)$-alkyl, which is unsubstituted or substituted with a substituent selected from the group consisting of: Cl, Br, I, F, —$CO_2R^{19}$, hydroxy-$(C_1-C_4)$-alkyl, or $(C_1-C_4)$-acyl, or
 (c) aryl or aryl-$(C_1-C_4)$-alkyl.

Wherein a preferred embodiment is when:

$R^1$ is:
 (a) $(C_1-C_6)$-alkyl or $(C_2-C_6)$-alkenyl or $(C_2-C_6)$-alkynyl each of which is unsubstituted or substituted with a substituent selected from the group consisting of:
  i) $(C_1-C_4)$-alkylthio,
  ii) $(C_1-C_4)$-alkoxy,
  iii) $CF_3$,
  iv) $CF_2-CF_3$, or
  v) $(C_3-C_5)$-cycloalkyl,
 (b) $(C_1-C_4)$-perfluoroalkyl, or
 (c) $(C_3-C_5)$-cycloalkyl; and —$A^1$—$A^2$—$A^3$—$A^4$— is:

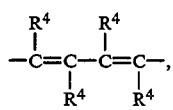 (a)

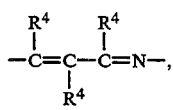 (b)

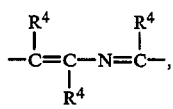 (c)

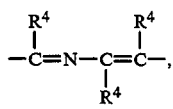 (d)

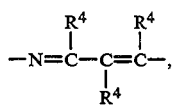 (e)

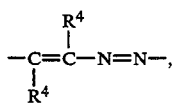 (f)

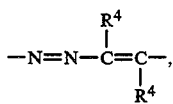 (g)

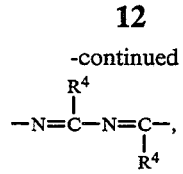 (h)

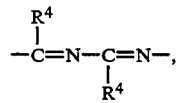 (i)

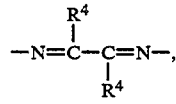 (j)

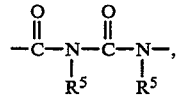 (k)

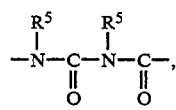 (l)

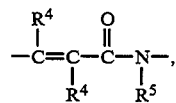 (m)

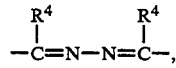 (n)

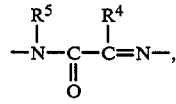 (o)

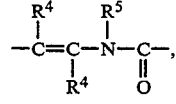 (p)

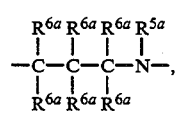 (q)

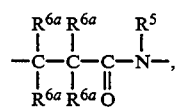 (r)

or

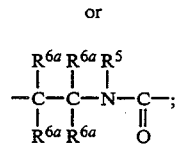 (s)

E is:
 (a) single bond,
 (b) —S—, or
 (c) —O—; and
n is 0, 1, or 2; and $R^2$ is:
 (a) H, or
 (b) $(C_1-C_6)$-alkyl; and $R^{2a}$ is:
 (a) $R^2$, (b) benzyl, or
(c) phenyl; and $R^4$ groups are independently:
(a) H,
(b) ($C_1$-$C_6$)-alkyl, which is unsubstituted or substituted with:
  i) OH,
  ii) $CO_2R^2$,
  iii) $NH_2$,
  iv) ($C_1$-$C_4$)-alkylamino,
  v) di[($C_1$-$C_4$)-alkyl]amino,
(c) Cl, Br, I, F,
(d) $CF_3$,
(e) $CO_2R^{2a}$,
(f) C(=O)$NR^{2a}R^{2a}$,
(g) —C(=O)-aryl,
(h) —$OR^{22}$,
(i) —S—($C_1$-$C_4$)-alkyl,
(j) —N[($C_1$-$C_4$)-alkyl]$_2$,
(k) —NHC(=O)($C_1$-$C_4$)-alkyl,
(l) —NHCOO($C_1$-$C_4$)-alkyl,
(m) —$SO_2$NH($C_1$-$C_4$)-alkyl,
(n) —$NO_2$,
(o) —$NHSO_2CH_3$,
(p) ($C_3$-$C_7$)-cycloalkyl, or
(q) when $R^4$ groups are on adjacent carbon atoms they may join to form a phenyl ring; and $R^5$ is:
(a) H, or
(b) ($C_1$-$C_6$)-alkyl, which is unsubstituted or substituted with: hydroxyl, or $CO_2R^2$; and $R^{5a}$ is:
(a) H,
(b) ($C_1$-$C_4$)-alkyl, or
(c) ($C_1$-$C_4$)-acyl; and $R^{6a}$ is:
(a) H, or
(b) ($C_1$-$C_4$)-alkyl; and $R^9$ and $R^{10}$ are independently:
(a) H,
(b) ($C_1$-$C_6$)-alkyl, unsubstituted or substituted with ($C_3$-$C_7$)cycloalkyl,
(c) ($C_2$-$C_6$)-alkenyl,
(d) ($C_2$-$C_6$)-alkynyl,
(e) Cl, Br, F, I,
(f) ($C_1$-$C_6$)-alkoxy, or
(g) when $R^9$ and $R^{10}$ are on adjacent carbons, they can be joined to form a phenyl ring,
(h) ($C_1$-$C_6$)-perfluoroalkyl,
(i) ($C_3$-$C_7$)cycloalkyl, which is unsubstituted or substituted with ($C_1$-$C_6$)-alkyl,
(j) phenyl or naphthyl,
(k) ($C_1$-$C_6$)-alkyl—S(O)$_n$—(CH$_2$)$_n$—,
(l) hydroxy-($C_1$-$C_6$)-alkyl,
(m) —$CF_3$,
(n) —$CO_2R^{2a}$,
(o) —OH,
(p) —$NR^2R^{15}$,
(q) —[($C_1$-$C_6$)-alkyl]$NR^2R^{15}$,
(r) —$NO_2$,
(s) —(CH$_2$)$_n$—$SO_2$—N($R^2$)$_2$,
(t) —$NR^2$CO—($C_1$-$C_4$)-alkyl, or
(u) —CON($R^2$)$_2$;

X is:
(a) —O—,
(b) —S(O)$_n$—,
(c) —$NR^{13}$—
(d) —CH$_2$O—,
(e) —CH$_2$S(O)$_n$,
(f) —CH$_2NR^{13}$—,
(g) —OCH$_2$—,
(h) —$NR^{13}CH_2$—,
(i) —S(O)$_n$CH$_2$—, or
(j) single bond; and Y is:
(a) single bond,
(b) —O—,
(d) —S(O)$_n$—, or
(e) —$NR^{13}$—; and
except that X and Y are not defined in such a way that the carbon atom to which Z is attached is also simultaneously bonded to two heteroatoms (O, N, S, SO, $SO_2$);

$R^{11}$ and $R^{12}$ are independently:
(a) H,
(b) ($C_1$-$C_6$)-alkyl, unsubstituted or substituted with a substituent selected from the group consisting of:
  (i) phenyl or naphthyl,
  (ii) ($C_3$-$C_7$)-cycloalkyl,
  (iii) $NR^2R^{15}$,
  (iv) morpholin-4-yl,
  (v) OH,
  (vi) $CO_2R^{2a}$, or
  (vii) CON($R^2$)$_2$,
(c) phenyl, naphthyl, phenyl-($C_1$-$C_2$)-alkyl, or naphthyl-($C_1$-$C_2$)-alkyl, unsubstituted or substituted with 1 to 3 substituents selected from the group consisting of:
  (i) Cl, Br, I, F,
  (ii) ($C_1$-$C_6$)-alkyl,
  (iii) [($C_1$-$C_5$)-alkenyl]CH$_2$—,
  (iv) [($C_1$-$C_5$)-alkynyl]CH$_2$—,
  (v) ($C_1$-$C_6$)-alkyl—S(O)$_n$—(CH$_2$)$_n$—,
  (vi) —$CF_3$,
  (vii) —$CO_2R^{2a}$,
  (viii) —OH,
  (ix) —$NR^2R^{15}$,
  (x) —$NO_2$,
  (xi) —$NR^2COR^2$,
  (xii) —CON($R^2$)2,
  (xiii) —$G^1$—[($C_1$-$C_6$)-alkyl]-$R^{18}$,
  (xiv) —N[CH$_2$CH$_2$]$_2$Q$^1$, or
  (xv) —P(O)[O—($C_1$-$C_4$)-alkyl]$_2$,
and can additionally be substituted with 1 or 2 substituents selected from the group consisting of: Br, Cl or F,
(d) ($C_3$-$C_7$)-cycloalkyl, or
(e) when Y is single bond, $R^{11}$ and $R^{12}$ can be joined to form a ring of 5 to 7 carbon atoms, the ring can be benzo-fused and one carbon of which can be replaced with a heteroatom selected from the group consisting of: O, S(O)$_n$ and $NR^{17}$; and $G^1$ is: a single bond, O, S(O)$_n$ or $NR^{18}$; and
$Q^1$ is: O, S(O)$_n$ or $NR^{17}$; and
$R^{13}$ is:
(a) H,
(b) ($C_1$-$C_6$)-alkyl,
(c) phenyl or naphthyl,
(d) phenyl-($C_1$-$C_6$)-alkyl—(C=O)— or naphthyl-($C_1$-$C_6$)-alkyl—(C=O)—, or
(e) ($C_1$-$C_6$)-alkyl—(C=O)—; and Z is:
(a) —$CO_2H$,
(b) $CO_2R^{19}$,
(c) -tetrazol-5-yl, (d) —CONH(tetrazol-5-yl),
(e) —CONHSO$_2$-aryl,
(f) —CONHSO$_2$—(C$_1$-C$_4$)-alkyl,
(g) —CONHSO$_2$—(C$_1$-C$_4$)-perfluoroalkyl,
(h) —CONHSO$_2$-heteroaryl, wherein heteroaryl is defined as a 5 or 6 membered aromatic ring containing one or two heteroatoms selected from the group consisting of O, N, or S;
(i) —CONHSO$_2$NR$^{2a}$R$^{2a}$,
(j) —SO$_2$NHCO—phenyl or—SO$_2$NHCO—naphthyl, wherein phenyl or naphthyl is unsubstituted or substituted as defined in R$^1$(b),
(k) —SO$_2$NHCO—(C$_1$-C$_6$)-alkyl,
(l) —SO$_2$NHCO—(C$_1$-C$_4$)-perfluoroalkyl,
(m) —SO$_2$NHCO—heteroaryl, wherein heteroaryl is defined as a 5 or 6 membered aromatic ring containing one or two heteroatoms selected from the group consisting of O, N, or S,
(n) —SO$_2$NHCONR$^{2a}$R$^{2a}$,
(o) —PO(OH)$_2$,
(p) —PO(OR$^2$)$_2$, or
(q) —PO(OH)(OR$^2$); and R$^{16}$ is:
(a) H,
(b) (C$_1$-C$_6$)-alkyl,
(c) phenyl or naphthyl, or
(d) phenyl-(C$_1$-C$_5$)-alkyl or naphthyl-(C$_1$-C$_5$)-alkyl; and R$^{17}$ is:
(a) H,
(b) (C$_1$-C$_4$)-alkyl,
(c) (C$_1$-C$_4$)-alkoxyl,
(d) phenyl or naphthyl,
(e) phenyl-(C$_1$-C$_4$)-alkyl or naphthyl-(C$_1$-C$_4$)-alkyl,
(f) CO$_2$R$^{2a}$,
(g) CON(R$^2$)$_2$,
(h) SO$_2$R$^{2a}$,
(i) SO$_2$N(R$^2$)$_2$,
(j) P(O)[(C$_1$-C$_4$)-alkoxyl]$_2$, or
(k) imidazol-2-yl or imidazol-4-yl, in which the imidazolyl can be substituted with (C$_1$-C$_4$)-alkyl; and R$^{18}$ is:
(a) OH,
(b) NR$^2$R$^{15}$,
(c) CO$_2$R$^{2a}$,
(d) CON(R$^2$)$_2$,
(e) S(O)$_n$—(C$_1$-C$_4$)-alkyl,
(f) N(CH$_2$CH$_2$)$_2$Q; and R$^{19}$ is:
(a) (C$_1$-C$_4$)-alkyl,
(b) CHR$^{20}$—O—COR$^{21}$,
(c) CH$_2$CH$_2$-N[(C$_1$-C$_2$)-alkyl]$_2$,
(d) CH$_2$CH$_2$-N[CH$_2$CH$_2$]$_2$O,
(e) (CH$_2$CH$_2$O)$_y$—O—[(C$_1$-C$_4$)-alkyl], wherein y is 1 or 2,
(f) phenyl, naphthyl, CH$_2$-phenyl or CH$_2$-phenyl, where phenyl or naphthyl is optionally substituted with CO$_2$-(C$_1$-C$_4$)-alkyl,

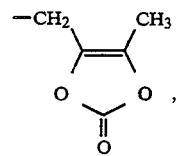

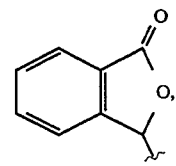

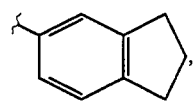

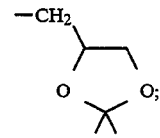

R$^{20}$ and R$^{21}$ independently are (C$_1$-C$_6$)-alkyl or phenyl.

A class of this embodiment of the invention is a compound of

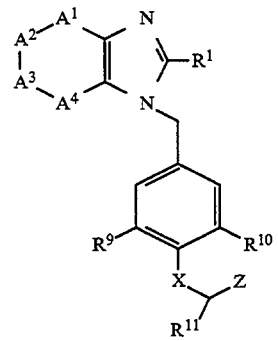

wherein,
—A$^1$—A$^2$—A$^3$—A$^4$— is:

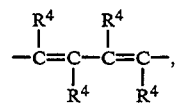

(a)

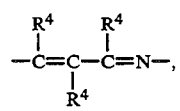

(b)

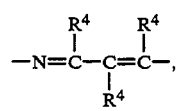

(c)

-continued (d) 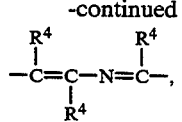

(e) 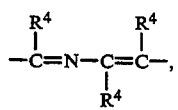

(f) 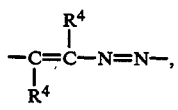

(g) 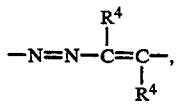

(h) 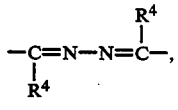

(i) 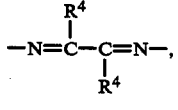

(j) 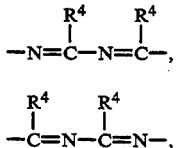

(k) 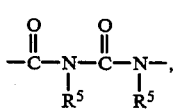

(l) 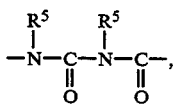

(m) 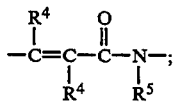

or (n)

$$-\overset{R^4}{\underset{R^4}{C}}=\overset{}{C}-\overset{O}{\overset{\parallel}{C}}-\overset{R^5}{N}-;$$

E is a single bond; and
$R^2$ is:
(a) H,
(b) $(C_1-C_6)$-alkyl; and
$R^{2a}$ is:
(a) $R^2$,
(b) benzyl, or
(c) phenyl; and
$R^4$ groups are independently:
(a) H,
(b) $(C_1-C_6)$-alkyl, which is unsubstituted or substituted with:
  i) OH,
  ii) $CO_2 R^{2a}$,
  iii) $NH_2$,
  iv) $(C_1-C_4)$-alkylamino, v) di[$(C_1-C_4)$-alkyl]amino,
(c) Cl, Br, I, F,
(d) $CF_3$,
(e) $CO_2R^{2a}$,
(f) $C(=O)NR^{2a}R^{2a}$,
(g) $(C_3-C_7)$-cycloalkyl,
(h) $-C(=O)$-phenyl or $-C(=O)$-naphthyl,
(i) $-OR^{22}$,
(j) $-N[(C_1-C_4)$-alkyl$]_2$,
(k) $-NHC(=O)(C_1-C_4)$-alkyl,
(l) $-NHCO_2(C_1-C_4)$-alkyl,
(m) $-SO_2NH-(C_1-C_4)$-alkyl,
(n) $-SO_2NH$-aryl,
(o) $-NO_2$,
(p) $-NHSO_2CH_3$,
$R^5$ is:
(a) H, or
(b) $(C_1-C_6)$-alkyl, unsubstituted or substituted with: hydroxyl, or $CO_2R^2$; and
(c) $(C_1-C_4)$-acyl; and
$R^{6a}$ is:
(a) H, or
(b) $(C_1-C_4)$-alkyl; and
$R^9$ and $R^{10}$ are independently:
(a) H,
(b) $(C_1-C_6)$-alkyl, unsubstituted or substituted with $(C_3-C_7)$-cycloalkyl,
(c) $(C_2-C_6)$-alkenyl,
(d) $(C_2-C_6)$-alkynyl,
(e) Cl, Br, F, I,
(f) $(C_1-C_6)$-alkoxy,
(e) Cl, Br, F, I,
(f) $(C_1-C_6)$-alkoxy,
(g) when $R^9$ and $R^{10}$ are on adjacent carbons, they can be joined to form an aryl ring,
(h) $(C_1-C_6)$-perfluoroalkyl,
(i) $(C_3-C_7)$-cycloalkyl, unsubstituted or substituted with $(C_1-C_6)$-alkyl, or
(j) phenyl; and
X is:
(a) $-O-$,
(b) $-S(O)_n-$,
(c) $-NR^{13}-$
(d) $-CH_2O-$,
(e) $-CH_2S(O)_n$,
(f) $-CH_2NR^{13}-$,
(g) $-OCH_2-$,
(h) $-NR^{13}CH_2-$,
(i) $-S(O)_nCH_2-$, or
(j) single bond; and
$R^{11}$ is:
(a) H,
(b) $(C_1-C_6)$-alkyl, unsubstituted or substituted with:
  i) phenyl or naphthyl, or
  ii) $(C_3-C_7)$-cycloalkyl,
(c) phenyl or naphthyl,
(d) phenyl-$(C_1-C_2)$-alkyl or naphthyl-$(C_1-C_2)$-alkyl, or
(e) $(C_3-C_7)$-cycloalkyl; and
$R^{13}$ is:
(a) H,
(b) $(C_1-C_6)$-alkyl,
(c) phenyl or naphthyl as defined in $R^1$(b),
(d) phenyl-$(C_1-C_6)$-alkyl-$(C=O)-$ or naphthyl-$(C_1-C_6)$-alkyl-$(C=O)-$, or
(e) $(C_1-C_6)$-alkyl-$(C=O)-$; and
Z is:

(a) —CO₂H,
(b) —CO₂—(C₁-C₆)-alkyl,
(c) -tetrazol-5-yl,
(d) —CONH(tetrazol-5-yl),
(e) —CONHSO₂-phenyl or —CONHSO₂-naphthyl, wherein phenyl or naphthyl is unsubstituted or substituted as defined in R¹(b),
(f) —CONHSO₂—(C₁-C₄)-alkyl,
(g) —CONHSO₂—(C₁-C₄)-perfluoroalkyl,
(h) —CONHSO₂-heteroaryl, where in heteroaryl is a 5 or 6 membered aromatic ring containing one or two heteroatoms selected from the group consisting of O, N, or S,
(i) —CONHSO₂NR²ᵃR²ᵃ,
(j) —SO₂NHCO—phenyl or —SO₂NHCO—naphthyl, wherein phenyl or naphthyl is unsubstituted or substituted as defined in R¹(b),
(k) —SO₂NHCO—(C₁-C₄)-alkyl,
(l) —SO₂NHCO—(C₁-C₄)-perfluoroalkyl,
(m) —SO₂NHCO—heteroaryl, where in heteroaryl is a 5 or 6 membered aromatic ring containing one or two heteroatoms selected from the group consisting of O, N, or S,
(n) —SO₂NHCONR²ᵃR²ᵃ,
(o) —PO(OH)₂,
(p) —PO(OR²)₂, or
(q) —PO(OH)(OR²).

Wherein a more preferred embodiment of the invention is when:

R¹ is:
(a) (C₁-C₆)-alkyl, (C₂-C₆)-alkenyl or (C₂-C₆)-alkynyl, each of which is unsubstituted or substituted with a substituent selected from the group consisting of:
  i) (C₁-C₄)-alkylthio,
  ii) (C₁-C₄)-alkoxy,
  iii) CF₃,
  iv) CF₂CF₃, or
  v) (C₃-C₅)-cycloalkyl, or
  (C₁-C₄)-perfluoroalkyl; and —A¹—A²—A³—A⁴— is:

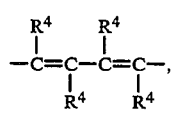 (a)

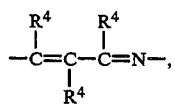 (b)

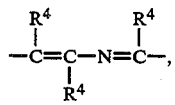 (c)

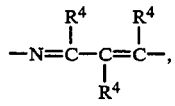 (d)

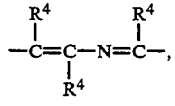 (e)

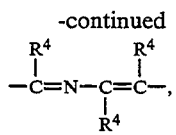 (f)

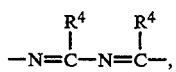 (g)

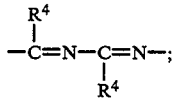 (h)

R⁹ and R¹⁰ are each independently
a) (C₁-C₆)-alkyl,
b) (C₁-C₆)-alkoxy,
c) F, Cl, Br, I,
d) (C₃-C₇)-cycloalkyl or
e) phenyl; and X is:
(a) —O—,
(b) NR¹³, or
(c) —CH₂—;

R¹¹ is
a) phenyl or naphthyl, or
b) phenyl-(C₁-C₂)-alkyl or naphthyl-(C₁-C₂)-alkyl; and Z is
a) —COOH,
b) -tetrazol-5-yl,
c) —CONHSO₂—(C₁-C₄)-alkyl,
d) —CONHSO₂—(C₁-C₄)-phenyl or —CONHSO₂—(C₁-C₄)-naphthyl, wherein phenyl or naphthyl is unsubstituted or substituted as defined in R¹(b),
e) —CONHSO₂—(C₁-C₄)-heteroaryl, or
f) —CONH (tetrazol-5-yl).

The following Tables (I–V) further exemplify the scope of the invention described by formula I (where X is —O— unless specified otherwise).

TABLE I

| R¹ | R⁴ᵃ | R⁴ᵇ | R⁹ | R¹⁰ | R¹¹ | Z |
|---|---|---|---|---|---|---|
| Pr | 4-Me | 7-Me | Me | Me | (3-Me)Ph | COOH |
| Bu | 5-PhCO | H | Bu | H | (3-Me)Ph | COOH |
| Ph | H | H | Pr | H | (3-Me)Ph | COOH |
| Pr | H | H | Cl | H | (3-Me)Ph | COOH |
| Bu | H | H | Br | Br | (3-Me)Ph | COOH |
| Ph | H | H | Cl | Cl | (3-Me)Ph | COOH |
| t-Bu | H | H | Pr | Pr | (3-Me)Ph | COOH |
| Pr | H | H | Pr | Pr | (3-Me)Ph | COOH |
| Bu | H | H | Pr | H | (4-Me)Ph | COOH |
| Ph | 4-Me | 7-Me | Me | Me | (3-Cl)Ph | COOH |
| Pr | Ph | H | Bu | H | (3-Cl)Ph | COOH |

TABLE I-continued

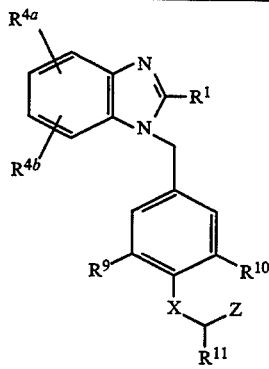

| R¹ | R⁴ᵃ | R⁴ᵇ | R⁹ | R¹⁰ | R¹¹ | Z |
|---|---|---|---|---|---|---|
| Bu | H | H | Cl | Cl | (3-Cl)Ph | COOH |
| Me | H | H | Br | Br | (3-Cl)Ph | COOH |
| Ph | H | H | Pr | Pr | (3-Cl)Ph | COOH |
| Bu | H | H | Pr | H | (2-MePh | COOH |
| Pr | 4-Me | 7-Me | Me | Me | (3-Br)Ph | COOH |
| Ph | 5-PhCO | H | Bu | H | (3-Br)Ph | COOH |
| Pr | H | H | Cl | Cl | (3-Br)Ph | COOH |
| Me | H | H | Br | Br | (3-Br)Ph | COOH |
| Pr | H | H | Pr | Pr | (3-Br)Ph | COOH |
| Bu | 4-Me | 7-Me | Me | Me | (3-NO₂)Ph | COOH |
| Ph | 5-PhCO | H | Bu | H | (3-NO₂)Ph | COOH |
| Pr | H | H | Cl | Cl | (3-NO₂)Ph | COOH |
| Me | H | H | Br | Br | (3-SMe)Ph | COOH |
| Bu | H | H | Pr | Pr | (3-SMe)Ph | COOH |

TABLE I-continued

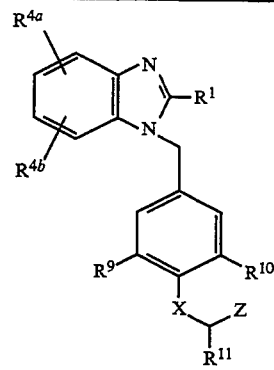

| R¹ | R⁴ᵃ | R⁴ᵇ | R⁹ | R¹⁰ | R¹¹ | Z |
|---|---|---|---|---|---|---|
| Ph | H | H | Pr | Pr | (3-Cl)Ph | tetrazol-5-yl |
| Ph | H | H | Pr | Pr | (3-Cl)Ph | CONHSO₂Me |
| Pr | H | H | Pr | Pr | (3-Br)Ph | CONHSO₂Me |
| Bu | H | H | Pr | Pr | (3-Me)Ph | CONHSO₂Me |
| Ph | H | H | Pr | Pr | (3-Cl)Ph | CONHSO₂Ph |
| Ph | H | H | Pr | Pr | (3-Br)Ph | CONHSO₂Ph |
| Ph | H | H | Pr | H | (3-Cl)Ph | CONHSO₂Ph |
| Ph | H | H | Br | Br | (3-Cl)Ph | CONHSO₂Ph |
| Pr | H | H | Pr | Pr | 2-Naphthyl | COOH |
| Pr | H | H | Pr | Pr | 2-Naphthyl | CONHSO₂Me |
| Pr | H | H | Pr | Pr | 2-Naphthyl | CONHSO₂Ph |
| Pr | H | H | Pr | Pr | 1-Naphthyl | COOH |
| Pr | H | H | Pr | Pr | 1-Naphthyl | CONHSO₂Me |
| Pr | H | H | Pr | Pr | 1-Naphthyl | CONHSO₂Ph. |

TABLE II

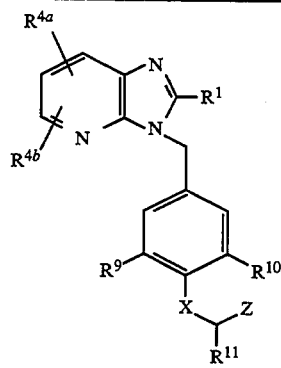

| R¹ | R⁴ᵃ | R⁴ᵇ | R⁹ | R¹⁰ | R¹¹ | Z |
|---|---|---|---|---|---|---|
| Et | 5-Me | 7-Me | Pr | Pr | Ph | COOH |
| Et | 5-Me | 7-Me | Me | Me | (3-Me)Ph | COOH |
| Pr | 6-PhCONH | H | Bu | H | (3-Me)Ph | COOH |
| Et | 5-Me | 7-Me | Pr | H | (3-Me)Ph | COOH |
| Et | 5-Me | 7-Me | Cl | H | (3-Me)Ph | COOH |
| Et | 5-Me | 7-Me | Br | Br | (3-Me)Ph | COOH |
| Ph | H | H | Cl | Cl | (3-Me)Ph | COOH |
| Me | H | H | Br | Br | (3-Me)Ph | COOH |
| Et | 5-Me | 7-Me | Pr | Pr | (3-Me)Ph | COOH |
| Et | 5-Me | 7-Me | Pr | Pr | (4-Me)Ph | COOH |
| Et | 5-Me | 7-Me | Me | Me | (3-Cl)Ph | COOH |
| Et | 5-Me | 7-Me | Bu | H | (3-Cl)Ph | COOH |
| Bu | H | H | Cl | Cl | (3-Cl)Ph | COOH |
| Me | 5-Me | 7-Me | Br | Br | (3-Cl)Ph | COOH |
| Et | 5-Me | 7-Me | Pr | Pr | (3-Cl)Ph | COOH |
| Pr | 5-Me | 7-Me | Pr | H | (4-Cl)Ph | COOH |
| Pr | 5-Me | 7-Me | Pr | H | (2-Cl)Ph | COOH |
| Pr | 5-Me | 7-Me | Pr | H | (3-Cl)Ph | COOH |
| Et | 5-Me | 7-Me | Pr | H | (2-Me)Ph | COOH |
| Et | 5-Me | 7-Me | Me | Me | (3-Br)Ph | COOH |
| Pr | 6-PhCONH | H | Bu | H | (3-Br)Ph | COOH |
| Et | 5-Me | 7-Me | Cl | Cl | (3-Br)Ph | COOH |
| Me | 5-Me | H | Br | Br | (3-Br)Ph | COOH |
| Ph | H | H | Pr | Pr | (3-Br)Ph | COOH |
| Et | 5-Me | 7-Me | Me | Me | (3-NO₂)Ph | COOH |
| Pr | 6-PhCONH | H | Bu | H | (3-NO₂)Ph | COOH |

TABLE II-continued

| R1 | R4a | R4b | R9 | R10 | | Z |
|---|---|---|---|---|---|---|
| Ph | H | H | Cl | Cl | (3-NO$_2$)Ph | COOH |
| Me | H | H | Br | Br | (3-SMe)Ph | COOH |
| Ph | H | H | Pr | Pr | (3-SMe)Ph | COOH |
| Bu | H | H | Pr | Pr | (3-Cl)Ph | tetrazol-5-yl |
| Et | 5-Me | 7-Me | Pr | Pr | (3-Cl)Ph | CONHSO$_2$Me |
| Ph | H | H | Pr | Pr | (3-Br)Ph | CONHSO$_2$Me |
| Ph | H | H | Pr | Pr | (3-Me)Ph | CONHSO$_2$Me |
| Me | 5-Me | 7-Me | Pr | Pr | (3-Cl)Ph | CONHSO$_2$Ph |
| Et | 5-Me | 7-Me | Pr | Pr | (3-Br)Ph | CONHSO$_2$Ph |
| Et | 5-Me | 7-Me | Pr | H | (3-Cl)Ph | CONHSO$_2$Ph |
| Et | 5-Me | 7-Me | Br | Br | (3-Cl)Ph | CONHSO$_2$Ph |
| Et | 5-Me | 7-Me | Pr | Pr | (3,4-di-Cl)Ph | COOH |
| Et | 5-Me | 7-Me | Pr | Pr | (3,4-di-Cl)Ph | CONHSO$_2$Me |
| Et | 5-Me | 7-Me | Pr | Pr | (3,4-di-Br)Ph | COOH |
| Et | 5-Me | 7-Me | Pr | Pr | (3,4-di-Br)Ph | CONHSO$_2$Me |
| Et | 5-Me | 7-Me | Pr | Pr | (3-NBn$_2$)Ph | COOH |
| Et | 5-Me | 7-Me | Pr | Pr | (3-NBn$_2$)Ph | CONHSO$_2$Me |
| Et | 5-Me | 7-Me | Pr | Pr | (3-NMe$_2$)Ph | CONHSO$_2$Me |
| Ph | 5-Me | H | Pr | Pr | (3,4-di-Cl)Ph | COOH |
| Ph | 5-Me | H | Pr | Pr | (3,4-di-Cl)Ph | CONHSO$_2$Me |
| Ph | 5-Me | H | Pr | Pr | (3,4-di-Br)Ph | COOH |
| Ph | 5-Me | H | Pr | Pr | (3,4-di-Br)Ph | CONHSO$_2$Me |
| Ph | 5-Me | H | Pr | Pr | (2-NBn$_2$)Ph | COOH |
| Ph | 5-Me | H | Pr | Pr | (3-NBn$_2$)Ph | CONHSO$_2$Me |
| Et | 5-Me | 7-Me | C$_6$H$_{11}$CH$_2$— | H | Ph | COOH |
| Et | 5-Me | 7-Me | Pr | H | (4-Cl)Ph | COOH |
| Et | 5-Me | 7-Me | Pr | H | (2-MeO)Ph | COOH |
| Et | 5-Me | 7-Me | Pr | H | (2,5-di-Br-3,4-di MeO)Ph | COOH |
| Et | 5-Me | 7-Me | Pr | Pr | (3-NMe$_2$)Ph | CONHSO$_2$Me |
| Et | 5-Me | 7-Me | Pr | Pr | 2-Naphthyl | COOH |
| Et | 5-Me | 7-Me | Pr | Pr | 2-Naphthyl | CONHSO$_2$Me |
| Pr | H | 7-Me | Pr | Pr | 2-Naphthyl | CONHSO$_2$Me |
| Et | 5-Me | 7-Me | Pr | Pr | (3-OPr)Ph | COOH |
| Et | 5-Me | 7-Me | Pr | Pr | (3-OPr)Ph | CONHSO$_2$Me |
| Pr | H | 7-Me | Pr | Pr | (3-OPr)Ph | CONHSO$_2$Me |
| Et | H | 7-Me | Pr | Pr | (3-OEt)Ph | COOH |
| Et | H | 7-Me | Pr | Pr | (3-OEt)Ph | CONHSO$_2$Me |
| Et | 5-Me | 7-Me | Pr | Pr | (3-OEt)Ph | CONHSO$_2$Me |
| Et | 5-Me | 7-Me | Pr | Pr | (3-OEt)Ph | COOH |
| Et | 5-Me | 7-Me | Pr | Pr | (3-NHCOMe)Ph | COOH |
| Et | 5-Me | 7-Me | Pr | Pr | (3-OiPr)Ph | COOH |
| Et | 5-Me | 7-Me | Pr | Pr | (3-NHCOOMe)Ph | COOH |
| Et | 5-Me | 7-Me | Pr | Pr | (3-Et)Ph | COOH |
| Et | 5-Me | 7-Me | Pr | Pr | (3-NMe$_2$)Ph | COOH |
| Pr | H | 7-Me | Pr | H | (2,6-diCl)Ph | COOH |
| Pr | H | 7-Me | Cl | H | (2-NO$_2$)Ph | COOH |
| Pr | H | 7-Me | Pr | H | cyclohexyl | COOH |
| Pr | H | 7-Me | H | H | Propyl | COOH |
| Pr | H | 7-Me | Cl | Pr | (2-COOH)Ph | COOH |
| Pr | H | 7-Me | Bu | H | (3-Me)Ph | Tetrazol-5-yl |
| Et | 5-Me | 7-Me | Cl | H | (2-Me)Ph | COOH |
| Et | 5-Me | 7-Me | Cl | OMe | Ph | COOH |
| Et | 5-Me | 7-Me | Cl | Cl | Ph | COOH |
| Et | 5-Me | 7-Me | Cl | H | Ph | COOH |
| Et | 5-Me | 7-Me | allyl | H | Ph | COOH |
| Et | 5-Me | 7-Me | Pr | H | Ph | COOH |
| Et | 5-Me | 7-Me | Pr | Pr | (2-Me)Ph | COOH |
| Et | 5-Me | 7-Me | Pr | Pr | (2-Cl)Ph | COOH |
| Et | 5-Me | 7-Me | Pr | Pr | (2-Cl)Ph | COOH |
| Et | 5-Me | 7-Me | Pr | Pr | (4-Cl)Ph | COOH |
| Et | 5-Me | 7-Me | Pr | Pr | (3-Br)Ph | COOH |
| Et | 5-Me | 7-Me | Pr | H | (2,5-di-F)Ph | COOH |
| Et | 5-Me | 7-Me | Pr | Pr | (2,5-di-F)Ph | COOH |
| Et | 5-Me | 7-Me | Pr | Pr | (3,5-di-CF$_3$)Ph | COOH |

TABLE II-continued

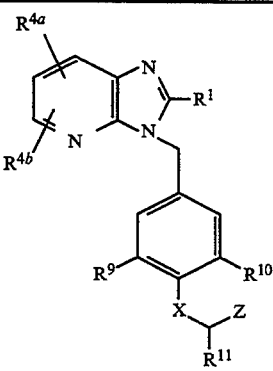

| | | | | | | | |
|---|---|---|---|---|---|---|---|
| Et | 5-Me | 7-Me | Pr | | Pr | (2-MeO)Ph | COOH |
| Et | 5-Me | 7-Me | Pr | | Pr | (3-NMe$_2$)Ph | COOH |
| Et | 5-COOMe | 7-Me | Pr | | H | Ph | COOH |
| Et | 5-COOH | 7-Me | Pr | | H | Ph | COOH |
| Et | 5-COOBzl | 7-Me | Pr | | H | Ph | COOH |

| X is NR$^{13}$ | R$^1$ | R$^{4a}$ | R$^{4b}$ | R$^9$ | R$^{10}$ | R$^{11}$ | Z |
|---|---|---|---|---|---|---|---|
| —NMe | Et | 4-Me | 7-Me | H | H | Ph | COOH |
| —NEt | Et | 5-Me | 7-Me | H | H | Ph | COOH |
| —NPr | Et | 5-Me | 7-Me | H | H | Ph | COOH |
| —NH | Et | 5-Me | 7-Me | H | H | Ph | COOH |
| —N-allyl | Et | 5-Me | 7-Me | H | H | Ph | COOH |
| —N-i-Bu | Et | 5-Me | 7-Me | H | H | Ph | COOH |
| —N—C—Pr | Et | 5-Me | 7-Me | H | H | Ph | COOH |
| —N—Sec—Bu | Et | 5-Me | 7-Me | H | H | Ph | COOH |
| —N-i-Pr | Et | 5-Me | 7-Me | H | H | Ph | COOH |
| —NMe | Et | 5-Me | 7-Me | H | H | Ph | tetrazol-5-yl. |

TABLE III

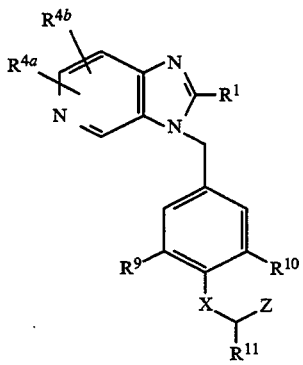

| R$^1$ | R$^{4a}$ | R$^{4b}$ | R$^9$ | R$^{10}$ | R$^{11}$ | Z |
|---|---|---|---|---|---|---|
| Bu | 4-Me | H | Me | Me | (3-Me)Ph | COOH |
| Bu | 6-PhCONH | H | Bu | H | (3-Me)Ph | COOH |
| Pr | 4-Me | 7-Me | Pr | H | (3-Me)Ph | COOH |
| Ph | 4-Cl | H | Cl | H | (3-Me)Ph | COOH |
| Ph | 4-Cl | H | Br | Br | (3-Me)Ph | COOH |
| Pr | H | 7-Cl | Cl | Cl | (3-Me)Ph | COOH |
| Me | 4-Cl | H | Br | Br | (3-Me)Ph | COOH |
| Ph | 4-Me | H | Pr | Pr | (3-Me)Ph | COOH |
| Bu | H | H | Pr | H | (4-Me)Ph | COOH |
| Pr | 4-Me | H | Me | Me | (3-Cl)Ph | COOH |
| Pr | H | 7-Me | Bu | H | (3-Cl)Ph | COOH |
| Ph | 4-Cl | H | Cl | Cl | (3-Cl)Ph | COOH |
| Me | 4-Cl | H | Br | Br | (3-Cl)Ph | COOH |
| Ph | 4-Cl | H | Pr | Pr | (3-Cl)Ph | COOH |
| Et | 4-Me | H | Pr | H | (2-Me)Ph | COOH |
| Ph | 4-Cl | H | Cl | Cl | (3-Br)Ph | COOH |
| Me | 4-Cl | H | Br | Br | (3-Br)Ph | COOH |
| Me | 4-Cl | H | Pr | Pr | (3-Br)Ph | COOH |
| Ph | 4-Cl | H | Me | Me | (3-NO$_2$)Ph | COOH |
| Me | H | H | Br | Br | (3-SMe)Ph | COOH |
| Ph | H | 7-Cl | Pr | Pr | (3-SMe)Ph | COOH |
| Et | 4-Me | H | Pr | Pr | (3-Cl)Ph | CONHSO$_2$Me |
| Ph | 4-Cl | H | Pr | Pr | 2-Naphthyl | COOH |
| Ph | 4-Cl | H | Me | Me | 2-Naphthyl | COOH |

TABLE III-continued

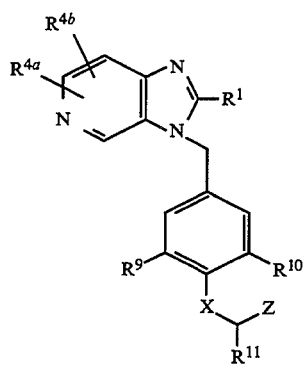

| R¹ | R⁴ᵃ | R⁴ᵇ | R⁹ | R¹⁰ | R¹¹ | Z |
|----|-----|-----|-----|------|------|---|
| Me | H | H | Br | Br | 2-Naphthyl | COOH |
| Ph | H | 7-Cl | Pr | Pr | 2-Naphthyl | COOH. |

TABLE IV

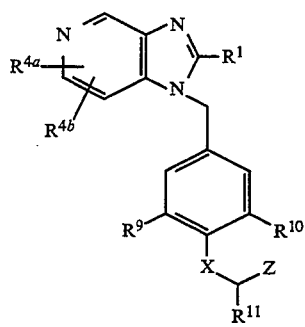

| R¹ | R⁴ᵃ | R⁴ᵇ | R⁹ | R¹⁰ | R¹¹ | Z |
|----|-----|-----|-----|------|------|---|
| Bu | 4-Me | H | Me | Me | (3-Me)Ph | COOH |
| Bu | 6-PhCONH | H | Bu | H | (3-Me)Ph | COOH |
| Pr | 4-Me | 7-Me | Pr | H | (3-Me)Ph | COOH |
| Ph | 4-Cl | H | Cl | H | (3-Me)Ph | COOH |
| Ph | 4-Cl | H | Br | Br | (3-Me)Ph | COOH |
| Pr | H | 7-Cl | Cl | Cl | (3-Me)Ph | COOH |
| Me | 4-Cl | H | Br | Br | (3-Me)Ph | COOH |
| Ph | 4-Me | H | Pr | Pr | (3-Me)Ph | COOH |
| Bu | H | H | Pr | H | (4-Me)Ph | COOH |
| Pr | 4-Me | H | Me | Me | (3-Cl)Ph | COOH |
| Pr | H | 7-Me | Bu | H | (3-Cl)Ph | COOH |
| Ph | 4-Cl | H | Cl | Cl | (3-Cl)Ph | COOH |
| Me | 4-Cl | H | Br | Br | (3-Cl)Ph | COOH |
| Ph | 4-Cl | H | Pr | Pr | (3-Cl)Ph | COOH |
| Et | 4-Me | H | Pr | H | (2-MePh | COOH |
| Ph | 4-Cl | H | Cl | Cl | (3-Br)Ph | COOH |
| Me | 4-Cl | H | Br | Br | (3-Br)Ph | COOH |
| Me | 4-Cl | H | Pr | Pr | (3-Br)Ph | COOH |
| Ph | 4-Cl | H | Me | Me | (3-NO₂)Ph | COOH |
| Me | H | H | Br | Br | (3-SMe)Ph | COOH |
| Ph | H | 7-Cl | Pr | Pr | (3-SMe)Ph | COOH |
| Et | 4-Me | H | Pr | Pr | (3-Cl)Ph | CONHSO₂Me |
| Ph | 4-Cl | H | Pr | Pr | 2-Naphthyl | COOH |
| Ph | 4-Cl | H | Me | Me | 2-Naphthyl | COOH |
| Me | H | H | Br | Br | 2-Naphthyl | COOH |
| Ph | H | 7-Cl | Pr | Pr | 2-Naphthyl | COOH. |

TABLE V

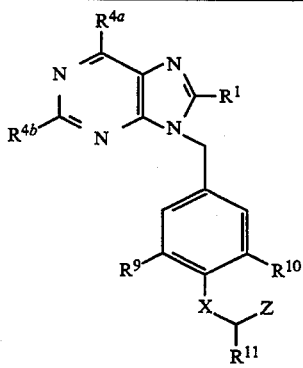

| R¹ | R⁴ᵃ | R⁴ᵇ | R⁹ | R¹⁰ | R¹¹ | Z |
|---|---|---|---|---|---|---|
| Ph | N(Me)₂ | H | Pr | Pr | (3-Me)Ph | COOH |
| Ph | CONH₂ | H | Bu | H | (3-Me)Ph | COOH |
| Pr | Me | Me | Pr | H | (3-Me)Ph | COOH |
| Ph | Cl | H | Cl | H | (3-Me)Ph | COOH |
| Ph | H | Cl | Cl | Cl | (3-Me)Ph | COOH |
| Me | Cl | H | Br | Br | (3-Me)Ph | COOH |
| Ph | H | H | Pr | Pr | (3-Me)Ph | COOH |
| Bu | H | H | H | H | (4-Me)Ph | COOH |
| Me | Me | H | Me | Me | (3-Cl)Ph | COOH |
| Ph | H | Me | Bu | H | (3-Cl)Ph | COOH |
| Ph | Cl | H | Cl | Cl | (3-Cl)Ph | COOH |
| Me | Cl | H | Br | Br | (3-Cl)Ph | COOH |
| Ph | Cl | H | Pr | Pr | (3-Cl)Ph | COOH |
| Pr | Me | H | Pr | H | (2-Me)Ph | COOH |
| Ph | Cl | H | Cl | Cl | (3-Br)Ph | COOH |
| Me | Cl | H | Br | Br | (3-Br)Ph | COOH |
| Ph | Cl | H | Pr | Pr | (3-Br)Ph | COOH |
| Ph | Cl | H | Me | Me | (3-NO₂)Ph | COOH |
| Me | H | H | Br | Br | (3-SMe)Ph | COOH |
| Ph | Cl | H | Pr | Pr | (3-Cl)Ph | tetrazol-5-yl |
| Ph | Me | H | Pr | Pr | (3-Cl)Ph | CONHSO₂Me. |

The alkyl substituents recited above denote straight and branched chain hydrocarbons of the length specified such as methyl, ethyl, isopropyl, isobutyl, neopentyl, isopentyl, etc.

The alkenyl and alkynyl substituents denote alkyl groups as described above which are modified so that each contains a carbon to carbon double bond or triple bond, respectively, such as vinyl, allyl and 2-butenyl.

Cycloalkyl denotes rings composed of 3 to 8 methylene groups, each of which may be substituted or unsubstituted with other hydrocarbon substituents, and include for example cyclopropyl, cyclopentyl, cyclohexyl and 4-methylcyclohexyl.

The alkoxy substituent represents an alkyl group as described above attached through an oxygen bridge.

The heteroaryl substituent recited above represents any 5- or 6-membered aromatic ring containing from one to three heteroatoms selected from the group consisting of nitrogen, oxygen, and sulfur, for example, pyridyl, furyl, pyrrolyl, thienyl, isothiazolyl, imidazolyl, pyrazinyl, pyrimidyl, pyrazolyl, purinyl, carbazolyl, isoxazolyl, thiazolyl, and oxazolyl.

The compounds of Formula (I) can be synthesized using the reactions and techniques described in the International Application WO91/11999 published under the Patent Cooperation Treaty (to Merck & Co.) on Aug. 22, 1991. The above mentioned application discloses the compounds of this invention where they are described as angiotensin II receptor antagonists useful in the treatment of hypertension and ocular hypertension.

The reactions are performed in a solvent appropriate to the reagents and materials employed and suitable for the transformation being effected. It is understood by those skilled in the art of organic synthesis that the functionality present on the heterocycle and in the reactants being employed should be consistent with the chemical transformations being conducted. Depending upon the reactions and techniques employed, optimal yields may require changing the order of synthetic steps or use of protecting groups followed by deprotection.

The compounds useful in the novel method treatment of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases; e.g., dicyclohexylamine salts, N-methyl-D-glucamine, salts with amino acids like arginine, lysine, and the like. Also, salts with organic and inorganic acids may be prepared; e.g., HCl, HBr, H₂SO₄, H₃PO₄, methanesulfonic, toluenesulfonic, maleic, fumaric, camphorsulfonic.

The salts can be formed by conventional means, such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

It will be appreciated that the compounds of general Formula I in this invention may be derivatised at functional groups to provide prodrug derivatives which are capable of conversion back to the parent compounds in vivo. The concept of prodrug administration has been extensively reviewed (e.g. A. A. Sinkula in *Annual Reports in Medicinal Chemistry*, Vol 10, R. V. Heinzelman, Ed., Academic Press, New York London, 1975, Ch. 31, pp. 306–326), H. Ferres, *Drugs of Today*, Vol 19, 499–538 (1983) and *J. Med. Chem.*, 18, 172 (1975). Examples of such prodrugs include the physiologically acceptable and metabolically labile ester derivatives, such as lower alkyl (e.g. methyl or ethyl esters), aryl (e.g. 5-indanyl esters), alkenyl (e.g. vinyl esters), alkoxyalkyl (e.g. methoxymethyl esters), alkylthioalkyl (e.g. methylthiomethyl esters), alkanoyloxyalkyl (e.g. pivaloyloxymethyl esters), and substituted or unsubstituted aminoethyl esters (e.g. 2-dimethylaminoethyl esters). Additionally, any physiologically acceptable equivalents of the compounds of general Formula I, similar to the metabolically labile esters, which are capable of producing the parent compounds of general Formula I in vivo, are within the scope of this invention.

It will be further appreciated that the majority of compounds of general Formula I claimed herein are asymmetric and are produced as racemic mixtures of enantiomers and that both the racemic compounds and the resolved individual enantiomers are considered to be in the scope of this invention. The racemic compounds of this invention may be resolved to provide individual enantiomers utilizing methods known to those skilled in the art of organic synthesis. For example, diastereoisomeric salts, esters or imides may be obtained from a racemic compound of general Formula I and a suitable optically active amine, amino acid, alcohol or the like. The diastereoisomeric salts, esters or imides are separated and purified, the optically active enantiomers are regenerated and the preferred enantiomer is the more potent isomer. The resolved enantiomers of the compounds of general Formula I, their pharmaceutically acceptable salts and their prodrug forms are also included within the scope of this invention.

Endothelin (ET-1), and two closely related bioactive peptides, ET-2 and ET-3, are widely distributed in mammalian tissues, and they can induce numerous biological responses in non-vascular as well as vascular tissues by binding to at least two distinct endothelin receptor subtypes. In addition to cardiovascular smooth muscle, neural and atrial sites, endothelin receptors may also be found in gastrointestinal, kidney, lung, urogenital, uteral and placental tissues.

Endothelin is a potent vasoconstrictor peptide and thus plays an in vivo role in arterial pressure-volume homeostasis. Not only peripheral, but coronary vascular resistance as well, is increased by endothelin. Cardiac output is decreased, while plasma renin activity is increased. There is a reduction in renal blood flow and glomerular filtration rate, while levels of atrial natriuretic factor, vasopressin, and aldosterone become elevated.

It is also considered, in accordance with the present invention, that antagonists for the endothelin receptor may be useful in preventing or reducing restenosis subsequent to denudation following angioplasty. Such denudation results from myointimal thickening following angioplasty, which is caused by increased endothelin release. Endothelin acts as a growth factor with respect to smooth muscle and fibroblastic cells, and possibly other types of cells, as well.

Endothelin is also a neuropeptide, acting on the posterior pituitary, where it modulates the release of the neurosecretory hormones vasopressin and oxytocin. Endothelin released from the posterior pituitary also acts as a circulating hormone, having a wide range of actions as discussed further above. This includes effects on the endocrine system, especially the adrenal glands. Endothelin increases plasma levels of epinephrine.

Consequently, the novel compounds of the present invention, which are receptor antagonists of endothelin, have therapeutic usefulness in preventing, decreasing or modulating the various physiological effects of endothelin discussed above, by wholly or partially blocking access of endothelin to its receptor.

Endothelin Receptor Binding Assays

The binding of the novel compound of this invention to the endothelin receptor was determined in accordance with the assay described in detail immediately below. It is similar to the assay described in Ambar et al. (1989) *Biochem. Biophys. Res. Commun.* 158, 195–201: and Kloog et al. (1989) *FEBS Letters*, 253, 199–202.

The endothelins (ETs) have a number of potent effects on a variety of cells, and exert their action by interacting with specific receptors present on cell membranes. The compounds described in the present invention act as antagonists of ET at the receptors. In order to identify ET antagonists and determine their efficacy in vitro, the following three ligand receptor assays were established.

Receptor binding assay using cow aorta membrane preparation

Thoracic aortae were obtained from freshly slaughtered calves and brought to the lab on wet ice. The adventitia were removed, and the aorta was opened up lengthwise. The lumenal surface of the tissue was scrubbed with cheesecloth to remove the endothelial layer. The tissue was ground in a meat grinder, and suspended in ice-cold 0.25M sucrose, 5 mM tris-HCl, pH 7.4, containing 0.5 µg/mL leupeptin and 7 µg/mL pepstatin A. Tissue was homogenized twice and then centrifuged for 10 minutes at 750×g at 4° C. The supernatant was filtered through cheesecloth and centrifuged again for 30 minutes at 48,000×g at 4° C. The membrane pellet thus obtained was resuspended in the buffer solution described above (including the protease inhibitors), and aliquots were quick-frozen and stored at −70° C. until use. Membranes were diluted into 50 mM KPi, 5 mM EDTA pH 7.5 containing 0.01% human serum albumin. Assays were done in triplicate. Test compounds and 100 pM [$^{125}$I]-endothelin-1 (2000–2200 Ci/µmole, obtained from New England Nuclear or Amersham) were placed in a tube containing this buffer, and the membranes prepared above were added last. The samples were incubated for 60 min at 37° C. At the end of this incubation, samples were filtered onto prewetted (with 2% BSA in water) glass fiber filter pads and washed with 150 mM NaCl, 0.1% BSA. The filters were assayed for $^{125}$I radioactivity in a gamma counter. Nondisplaceable binding of [$^{125}$I]-endothelin-I was measured in the presence of 100 nM unlabelled endothelin-1 [Endothelin-1 (ET-1) was purchased from Peptides International (Louisville, Ky.)]. Specific binding is defined as total binding minus nondisplaceable binding. The inhibitory concentration (IC$_{50}$) which gives 50% displacement of the total specifically bound [$^{125}$I]-endothelin-1 was presented as a measure of the potency of such compound as ET antagonist.

Receptor binding assay using rat hippocampal membrane preparation

Rat hippocampi were obtained from freshly sacrificed male Sprague-Dawley rats and placed in ice cold 0.25M sucrose, 5 mM tris-HCl, pH 7.4 containing 0.5 µg/mL leupeptin, 7 µg/mL pepstatin A. Hippocampi were weighed and placed in a Dounce homogenizer with 25 volumes (wet weight to volume) ice-cold sucrose buffer in the presence of protease inhibitors. Hippocampi were homogenized using the Dounce (glass-glass) homogenizer with type A pestle, with the homogenizer immersed in ice. Tissue homogenate was centrifuged at 750×g for 10 min at 4° C. Supernatant was filtered through dampened cheesecloth, and centrifuged again at 48,000×g for 30 min at 4° C. Membrane pellets were resuspended in sucrose buffer with protease inhibitors. Aliquots of this preparation were quick frozen and stored at −70° C. until use. Membranes were diluted into 50 mM KPi, 5 mM EDTA pH 7.5 containing 0.01% human serum albumin. Assays were done in triplicate. Test compounds and 25 pM [$^{125}$I]-endothelin-1 (2000–2200 Ci/µmole, obtained from New England Nuclear or Amersham) were placed in a tube containing this buffer, and the membranes prepared above were added last. The samples were incubated for 60 min at 37° C. At the end of this incubation, samples were filtered onto prewetted (with 2% BSA in water) glass fiber filter pads and washed with 150 mM NaCl, 0.1% BSA. The filters were assayed for $^{125}$I radioactivity in a gamma counter. Nondisplaceable binding of [$^{125}$I]-endothelin-1 was measured in the presence of 100 nM unlabelled endothelin-1 [Endothelin-1 (ET-1) was purchased from Peptides International (Louisville, Ky.)]. Specific binding is defined as total binding minus nondisplaceable binding. The inhibitory concentration (IC$_{50}$) which gives 50% displacement of the total specifically bound [$^{125}$I]-endothelin-I was presented as a measure of the potency of such compounds as endothelin antagonists.

Receptor binding assay using cloned human ET receptors expressed in Chinese Hamster Ovary Cells Both endothelin receptor subtypes were cloned from a human cDNA library and were individually expressed in Chinese Hamster Ovary cells. Cells were harvested by addition of 126 mM NaCl, 5 mM KCl, 2 mM EDTA, 1 mM NaH$_2$PO$_4$, 15 mM glucose, 10 mM tris/HEPES pH 7.4 Cells were centrifuged at 250×g for 5 minutes. The supernatant was aspirated off, and the cells were resuspended in the 50 mM KPi, 5 mM EDTA pH 7.5 containing 0.01% human serum albumin. Assays were done in triplicate. Test compounds and 25–100 pM [$^{125}$I]-endothelin-1 (2000–2200 Ci/μmole, obtained from New England Nuclear or Amersham) were placed in a tube containing 50 mM KPi, 5 mM EDTA pH 7.5 containing 0.01% human serum albumin, and the cells prepared above were added last. The samples were incubated for 60 min at 37° C. At the end of this incubation, samples were filtered onto prewetted (with 2% BSA in water) glass fiber filter pad and washed with 150 mM NaCl, 0.1% BSA.

The filters were assayed for $^{125}$I radioactivity in a gamma counter. Nondisplaceable binding of [$^{125}$I]-endothelin-1 was measured in the presence of 100 nM unlabelled endothelin-I [Endothelin-1 (ET-1) was purchased from Peptides International (Louisville, Ky.)]. Specific binding is defined as total binding minus nondisplaceable binding. The inhibitory concentration (IC$_{50}$) which gives 50% displacement of the total specifically bound [$^{125}$I]-endothelin-1 was presented as a measure of the potency of such compounds as endothelin antagonists.

The binding assays described above were used to evaluate the potency of interaction of compounds of the invention with endothelin receptors. To determine whether these compounds were endothelin antagonists, assays which measure the ability of these compounds to inhibit endothelin-stimulated phosphatidylinositol hydrolysis were established. Rat uterus contains predominantly one of the known endothelin receptor subtypes (ET$_A$).

Phosphatidylinositol hydrolysis assays using rat uterine slices

Diethylstilbestrol primed female Sprague-Dawley rats were sacrificed and their uteri were collected, dissected of fat and connective tissue and minced. Minced tissue was added to oxygenated (95% O$_2$, 5% CO$_2$) 127 mM NaCl, 25 mM NaHCO$_3$, 10 mM Glucose, 2.5 mM KCl, 1.2 mM KH$_2$PO$_4$, 1.2 mM MgSO$_4$, 1.8 mM CaCl$_2$. To the tissue mince, 1.2 μM myo-[$^3$H]-inositol (Amersham) was added. The mince was incubated 90 min at 37° C., with constant oxygenation. After incubation, the loaded tissue mince was washed five times with the same oxygenated buffer to remove excess radiolabelled inositol. The tissue mince was resuspended in the above buffer, containing 10 mM LiCl, aliquotted into tubes, and 3 nM endothelin-1 with and without test compounds was added to a final concentration of 3 nM to start the assay. Assays were done in quadruplicate. Samples were incubated at 37° C. under blowing O$_2$ in a hooded water bath for 30 minutes. Reaction was stopped by addition of trichloroacetic acid to 6% concentration. Samples were sonicated for 10 min, centrifuged 20 min, then trichloroacetic acid was extracted with water-saturated ethyl ether. An aliquot of each sample was neutralized and diluted by addition of 50 mM tris-HCl pH 7.4. A 100 μL aliquot of this solution was assayed for radioactivity in a beta counter. The diluted neutralized sample was applied to Dowex 1×8-formate columns, washed with water, then washed with 60 mM ammonium formate, 5 mM sodium tetraborate. Samples were eluted with 200 mM ammonium formate. 5 mM sodium tetraborate. The radioactivity of each eluted sample was measured in a beta counter. Radioactivity was normalized by dividing radioactivity in post column sample by radioactivity in precolumn sample. Control values (100% stimulated) are values in the presence of endothelin minus the values in the absence of endothelin (basal). Test sample values are the values in the presence of endothelin and test sample minus basal. Inhibitory concentration (IC$_{50}$) is the concentration of test compound required to give a sample activity of 50% of control value.

Sarafotoxin S6c is a member of the endothelin family which binds preferentially to one of the known endothelin receptor subtypes (ET$_B$).

Phosphatidylinositol hydrolysis assays using rat lung slices

Male Sprague-Dawley rats were sacrificed and their lungs were collected, dissected of fat and connective tissue and minced. Minced tissue was added to oxygenated (95% O$_2$, 5% CO$_2$) 127 mM NaCl, 25 mM NaHCO$_3$, 10 mM Glucose, 2.5 mM KCl, 1.2 mM KH$_2$PO$_4$, 1.2 mM MgSO$_4$, 1.8 mM CaCl$_2$. To the tissue mince, 1.2 μM myo-[$^3$H]-inositol was added. The mince was incubated 60 min at 37° C., with constant oxygenation. After incubation, loaded tissue mince was washed five times with the same oxygenated buffer to remove excess radiolabelled inositol. Tissue mince was resuspended in the above buffer, containing 10 mM LiCl, aliquotted into tubes, and sarafotoxin S6c (to a final concentration of 3 nM) with and without test compounds was added to start the assay. Assays were done in quadruplicate. Samples were incubated at 37° C. under blowing O$_2$ in a hooded water bath for 30 minutes. Reaction was stopped by addition of 0.5 mL 18% trichloroacetic acid to 6% concentration. Samples were sonicated for 10 min, centrifuged 20 min, then trichloroacetic acid was extracted with water-saturated ethyl ether. An aliquot of each sample was neutralized and diluted by addition of 50 mM tris-HCl pH 7.4. A 100 μL aliquot of this solution was assayed for radioactivity in a beta counter. The diluted neutralized sample was applied to Dowex 1×8-formate columns, washed with water, then washed with 60 mM ammonium formate, 5 mM sodium tetraborate. Samples were eluted with 200 mM ammonium formate, 5 mM sodium tetraborate. The radioactivity of each eluted sample was measured in a beta counter. Radioactivity was normalized by dividing radioactivity in post column Sample by radioactivity in precolumn sample. Control values (100% stimulated) are values in the presence of sarafotoxin minus the values in the absence of sarafotoxin (basal). Test sample values are the values in the presence of sarafotoxin and test sample minus basal. Inhibitory concentration (IC$_{50}$) is the concentration of test compound required to give a sample activity of 50% of control value.

Phosphatidylinositol hydrolysis assays using cloned human endothelin receptors expressed in Chinese Hamster Ovary cells.

Endothelin receptors of both receptor subtypes were cloned from a human cDNA library and were individually expressed in Chinese Hamster Ovary cells. Cells were loaded overnight by the addition of 1.2 μM myo-

[³H]-inositol to their growth medium. Cells were harvested by addition of 126 mM NaCl, 5 mM KCl, 2 mM EDTA, 1 mM $NaH_2PO_4$, 15 mM glucose, 10 mM tris/-HEPES pH 7.4 Cells were washed five times by centrifugation at 250×g for 5 minutes to remove excess radiolabelled inositol. The supernatant was aspirated off, and the cells were resuspended in the same oxygenated (95% $O_2$, 5% $CO_2$) buffer containing 10 mM LiCl, aliquotted into tubes, and endothelin-1 (to a final concentration of 0.3 nM) with and without test compounds was added to start the assay. Assays were done in quadruplicate. Samples were incubated at 37° C. under blowing $O_2$ in a hooded water bath for 30 minutes. Reaction was stopped by addition of 0.5 mL 18% trichloroacetic acid to 6% concentration. Samples were sonicated for 10 min, centrifuged 20 min, then trichloroacetic acid was extracted with water-saturated ethyl ether. An aliquot of each sample was neutralized and diluted by addition of 50 mM tris-HCl pH 7.4. A 100 μL aliquot of this solution was assayed for radioactivity in a beta counter. The diluted neutralized sample was applied to Dowex 1×8-formate columns, washed with water, then washed with 60 mM ammonium formate. 5 mM sodium tetraborate. Samples were eluted with 200 mM ammonium formate, 5 mM sodium tetraborate. The radioactivity of each eluted sample was measured in a beta counter. Radioactivity was normalized by dividing radioactivity in post column sample by radioactivity in precolumn sample. Control values (100% stimulated) are values in the presence of endothelin minus the values in the absence of endothelin (basal). Test sample values are the values in the presence of endothelin and test sample minus basal. Inhibitory concentration ($IC_{50}$) is the concentration of test compound required to give a sample activity of 50% of control value.

Using the methodology described above, the compounds of the invention were evaluated and found to exhibit $IC_{50}$ values of at least <50 μM thereby demonstrating and confirming the utility of the compounds of this invention as endothelin antagonists.

Accordingly the novel compounds of the present invention are useful in human therapy for treating asthma, hypertension, pulmonary hypertension, arteriosclerosis, heart failure, renal failure particularly post-ischemic renal failure, cyclosporin nephrotoxicity, vasospasm, vascular restenosis, cerebral and cardiac ischemia and other ischemic states, myocardial infarction, Raynaud's disease, inflammatory bowel diseases, including Crohn's disease and ulcerative colitis, as well as other inflammatory diseases, or endotoxic shock caused by or associated with endothelin, by administration to a patient in need of such treatment of a therapeutically effective amount thereof.

In the management of hypertension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 0.5 mg–1.0 g per patient per day which can be administered in single or multiple doses. Preferably, the dosage range will be about 0.5–500 mg per patient per day; more preferably about 0.5–200 mg per patient per day.

The present invention also relates to pharmaceutical compositions for treating asthma, hypertension, pulmonary hypertension, arteriosclerosis, heart failure, renal failure particularly post-ischemic renal failure, cyclosporin nephrotoxicity, vasospasm, vascular restenosis, cerebral and cardiac ischemia and other ischemic states, myocardial infarction, Raynaud's disease, inflammatory bowel diseases, including Crohn's disease and ulcerative colitis, as well as other inflammatory diseases, or endotoxic shock caused by or associated with endothelin, comprising a therapeutically effective amount of the novel compound of this invention together with a pharmaceutically acceptable carrier therefor.

About 0.5 mg to 1.0 g of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unitform is a capsule, it may contain in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples illustrate the preparation of the compounds of Formula I and their incorporation into pharmaceutical compositions and as such are not to be considered as limiting the invention set forth in the claims appended hereto.

EXAMPLE 1

General Procedure for the Synthesis of 2-Bromophenylacetic Esters from Substituted Aromatic Aldehydes Step A: Preparation of 2-trimethylsilyloxy-2-(aryl)acetonitrile To a solution of 8.33 mmol of an appropriate aromatic aldehyde dissolved in 20 mL of dichloromethane is added 10.0 mmol of trimethylsilylcyanide, 1–2 mg of potassium cyanide, 1-2 mg of 18-crown-6, and the reaction mixture is stirred at room temperature for 3-12 hours. The reaction mixture is then diluted into diethyl ether, washed with NaHCO$_3$, brine, dried (MgSO$_4$), filtered and evaporated. The residual oil is used directly in the next step.

Step B: Preparation of methyl 2-hydroxy-2-arylacetate

To a stirred 0° C. (ice-water bath) solution of 8.35 mmol of the product of Step A dissolved in 10 mL of methanol is introduced a slow stream of anhydrous hydrogen chloride gas. After 5 minutes the hydrogen chloride is turned off and the flask is stoppered and stirred at room temperature 14 hours. The reaction is then poured into ice-water and extracted into chloroform. The chloroform solution is filtered through a pad of silica gel and the silica gel was washed with additional chloroform. The combined filtrate is evaporated in vacuo to give the title compound.

Step C: Preparation of methyl 2-bromo-2-arylacetate

To a cooled (0° C.) solution of 0.425 g (2.19 mmol) of the product of Step B dissolved in 10 mL of dichloromethane is added 2.74 mmol of triphenylphosphine followed by 2.74 mmol of carbon tetrabromide. After 30 minutes the reaction is allowed to warm to room temperature and stirring is continued for 2-12 hours. The reaction mixture is evaporated in vacuo, and the residue is purified on a silica gel flash chromatography column using an appropriate eluting solvent to afford the title compound.

EXAMPLE 2

General Procedure for the Alkylation of Heterocycles with 2-Bromophenylacetic Esters Step A: Alkylation of the heterocycle A suspension of an appropriate heterocycle (5.71 mmol) and NaH (1.1 eq) in DMF (25 mL) is stirred for 1 hour and then cooled to 0° C. 4-Benzyloxybenzyl chloride (1.46 g; 1.1 eq) is then added and the ice bath removed. The reaction mixture is stirred for 2-4 hours and then concentrated in vacuo. The residue is purified on a silica gel flash chromatography column using an appropriate eluting solvent to yield the desired product.

Step B: Removal of the protecting group

To a solution of the product of Step A (1.62 mmol) in 10 mL of MeOH is added 60 mg of a 10% Pd/C catalyst and stirred under an H$_2$ atmosphere (1 atm) for 7 hours. The reaction mixture is filtered and concentrated in vacuo to yield the corresponding phenolic compound.

Step C: Alkylation of the phenolic component

To a suspension of 0.32 mmol of a 35% oil dispersion of potassium hydride in 0.5 mL of DMF is added 0.32 mmol of the phenolic compound (Step B) and the reaction is stirred under an N$_2$ atmosphere. After stirring for 15 minutes, a catalytic amount of 18-crown-6 is added followed by addition of a solution of 0.35 mmol of the product of Example 1 dissolved in 1.0 mL of DMF. The reaction mixture, after stirring for 4 hours, is concentrated in vacuo, and the residue is purified on a silica gel flash chromatography column using an appropriate solvent system to afford the title compound.

Step D: General procedure for ester hydrolysis

To a solution of 0.21 mmol of the product of Step C dissolved in 3 mL of ethanol is added 1 mL of a 1N NaOH solution. The reaction mixture is stirred at room temperature for 1.5 hours, neutralized to pH 7 with 1N HCl and then concentrated in vacuo. The residue is purified on a silica gel flash chromatography column to afford the corresponding carboxylic acid.

EXAMPLE 3

3-[4-(1-Carboxy-1-(2-methylphenyl)methoxy)-3-chlorophenylmethyl]-5,7-dimethyl-2-ethyl-3H-imidazo[4,5-b]pyridine Step A: Preparation of methyl 4-tert-butyldimethylsilyloxy-3-chlorobenzoate To a solution of 5.00 g (26.8 mmol) of methyl 3-chloro-4-hydroxybenzoate dissolved in 40 mL of CH$_2$Cl$_2$ was added 6.55 g (53.6 mmol) of 4-dimethylaminopyridine, 4.85 g (32.2 mmol) of tert-butyldimethylchlorosilane and the mixture was stirred at room temperature for 3.5 hours. The reaction mixture was filtered, diluted with ethyl acetate, washed with 0.1 N HCl, saturated NaHCO$_3$, and brine. The product layer was then dried (MgSO$_4$), filtered and evaporated in vacuo to afford 8.05 g (100%) of the title compound.

$^1$H NMR (300MHz, CDCl$_3$, ppm): δ0.25 (s, 6H), 1.00 (s, 9H), 3.85 (s, 3H), 6.85 (d, 1H), 7.80 (d, 1H), 8.05 (s, 1H).

FAB-MS: m/e 301,303 (M+1).

Step B: Preparation of 4-tert-butyldimethylsilyloxy-3-chlorobenzyl alcohol

To a stirred and cooled (0° C.) solution of 8.00 g (26.7 mmol) of the product of Step A dissolved in 50 mL of anhydrous THF was added 53.3 mL (53.3 mmol) of a 1M solution of lithium aluminum hydride in THF. After the addition was complete the reaction mixture was allowed to warm to room temperature and stirred 2 hours. The stirred reaction was then quenched by dropwise addition of 2.5 mL water, then 2.5 mL of 15% NaOH, and finally 7.5 mL water. The reaction mixture was then filtered and concentrated in vacuo. The residue was dissolved in ethyl acetate, washed with 1N HCl, saturated NaHCO$_3$, dried (MgSO$_4$), and evaporated in vacuo to afford 4.0 g (53%) of the title compound.

$^1$H NMR (300 MHz, CDCl$_3$, ppm): δ0.20 (s, 6H), 1.00 (s, 9H), 1.80 (br s, 1H), 4.55 (s, 2H), 6.85 (d, 1H), 7.10 (d, 1H), 7.35 (s, 1H).

FAB-MS: m/e 255,257 (M+1).

Step C: Preparation of 4-tert-butyldimethylsilyloxy-3-chlorobenzyl bromide

To a stirred and cooled (0° C.) solution of 4.00 g (14.1 mmol) of the product of Step B dissolved in 70 mL of CH$_2$Cl$_2$ was added 5.84 g (17.6 mmol) of carbon tetrabromide and 4.61 g (17.6 mmol) of triphenylphosphine. After the addition the reaction mixture was allowed to of the product of Step B dissolved in 70 mL of CH$_2$Cl$_2$ was added 5.84 g evaporated in vacuo and purified on a silica gel flash chromatography column eluted with 2% ethyl acetate/hexane to afford 4.50 g (92%) of the title compound.

$^1$H NMR (300 MHz, CDCl$_3$, ppm): δ0.20 (s, 6H), 1.00 (s, 9H), 4.40 (s, H), 6.80 (d, 1H), 7.15 (d, 1H), 7.35 (s, 1H).

Step D: Preparation of 3-(4-tert-butyldimethylsilyloxy-3-chlorophenylmethyl) -5,7-dimethyl-2-ethyl-3H-imidazo[4,5-b]-pyridine The product of Step C (1.79 g, 5.15 mmol) was used to alkylate 0.750 g (4.29 mmol) of 5,7-dimethyl-2-ethylimidazo[4,5-b]-pyridine (prepared as described in EP 400,974 published Dec. 5, 1990) according to the procedure described for Step B of Example 2, which after purification afforded 0.294 g (15%) of the title compound.

$^1$H NMR (300 MHz, CDCl$_3$, ppm): d 0.20 (s, 6H), 1.00 (s, 9H), 1.20–1.30 (t, 3H), 2.58 (s, 3H), 2.60 (s, 3H), 2.70–2.80 (m, 2H), 5.35 (s, 2H), 7.75 (d, 1H), 7.85–7.90 (m, 2H), 7.15 (s, 1H).

FAB-MS: m/e 430, 432 (M+1).

Step E: Preparation of 3-(3-chloro-4-hydroxyphenylmethyl)-5,7-dimethyl-2-ethyl-3H-imidazo[4,5-b]pyridine To a solution of 0.294 g (0.661 mmol) of the product of Step D dissolved in 4 mL of THF was added 0.69 mL (0.69 mmol) of a 1.0M solution of tetra-n-butylammonium fluoride in THF, and the reaction mixture was stirred 2 hours at room temperature. The reaction was then concentrated in vacuo and purified by filtration through a silica gel pad eluted with chloroform. Evaporation of the filtrate and drying in vacuo afforded 0.188 g (87%) of the title compound.

$^1$H NMR (300 MHz, CD$_3$OD, ppm): a 1.25–1.35 (t, 3H), 2.65 (s., 3H), 2.67 (s, 3H), 2.85–2.95 (m, 2H), 5.45 (s, 2H), 6.90 (d, 1H), 6.95 (d, 1H), 7.05 (s, 1H), 7.15 (s, 1H).

FAB-MS: m/e 316, 318 (M+1).

Step F: Preparation of 3-[4-( 1-carbomethoxy- 1-(2-methylphenyl)methoxy) - 3-chlorophenylmethyl]-5,7-dimethyl-2-ethyl -3H-imidazo[4,5-b]pyridine To a suspension of 7 mg of a 60% oil dispersion of sodium hydride in 0.75 mL of DMF was added 0.050 g (0.16 mmol) of the product of Step E and the reaction mixture was stirred 10 minutes under an N$_2$ atmosphere. A solution of methyl 2-bromo-2'-methyl-phenylacetate dissolved in 0.75 mL of DMF was then added and the reaction was stirred for 2 hours at room temperature. The reaction mixture was then partitioned between ethyl acetate and water, the organic layer was separated, dried (MgSO$_4$), filtered and evaporated. The residue was purified on a silica gel flash chromatography column eluted with EtOAc/hexane/CHCl$_3$ (50:40:10) to afford 0.070 g (92%) of the title compound.

$^1$H NMR (300 MHz, CDCl$_3$, ppm): δ1.25–1.35 (t, 3H), 2.45 (s, 3H), 2.60 (s, 3H), 3.65 (s, 3H), 2.75–2.85 (m, 2H), 3.70 (s, 3H), 5.35 (s, 2H), 5.60 (s, 1H), 6.75 (d, 1H), 6.85–6.95 (m, 2H), 7.15–7.40 (m, 4H), 7.55–7.65 (m, 1H).

FAB-MS: m/e 478, 480 (M+1, 3:1 ratio).

Step G: Preparation of 3-[4-(1 -carboxy-1-(2-methylphenyl)methoxy) -3-chlorophenylmethyl]-5,7-dimethyl-2-ethyl-3H-imidazo[4,5-b]pyridine Using the general procedure for ester hydrolysis described in Step D of Example 2, 0.040 g (0.15 mmol) of the product of Step F was converted to 0.066 g (97%) of the title compound.

$^1$H NMR (300 MHz, CD$_3$OD, ppm): δ1.25–1.35 (t, 3H), 2.50 (s, 3H), 2.63 (s, 3H), 2.65 (s, 3H), 2.85–2.95 (m, 2H), 5.50 (s, 2H), 5.80 (s, 1H), 6.95–7.10 (m, 3H), 7.20–7.30 (m, 4H), 7.60 (d, 1H).

FAB-MS: m/e 464, 466 (M+1, 3:1 ratio).

EXAMPLE 4

3-[4-(1-Carboxy-1-phenylmethoxy)-3-chloro-5-methoxyphenyl]methyl-5,7-dimethyl-2-ethyl-3H-imidazo[4,5-b]pyridine Step A: Preparation of methyl 2-(2-chloro-4-hydroxymethyl-6-methoxyphenoxy)-2-phenylacetate A mixture of 0.50 g (2.65 mmol) of 3-chloro-4-hydroxy-5-methoxy-benzaldehyde, 0.668 g (2.92 mmol) of methyl 2-bromophenylacetate and K$_2$CO$_3$ (0.73 g, 5.3 mmol) in acetone (8 mL) was refluxed for 14 h. The mixture was cooled, filtered and evaporated in vacuo, and the residue was purified by flash chromatography on a silica gel column using 5% ethylacetate in hexane to afford 0.570 g (64%) of the title compound.

$^1$H NMR (300 MHz, CDCl$_3$, ppm): δ1.65–1.75 (t, 1H), 3.70 (s, 3H), 3.80 (s, 3H), 4.55 (d, 2H), 5.75 (s, 1H), 6.80 (s, 1H), 6.90 (s, 1H). 7.30–7.40 (m, 3H), 7.50–7.60 (m, 2H).

FAB-MS: m/e 337, 339 (M+1, 3:1 ratio).

Step B: Preparation of 2-(4-bromomethyl-2-chloro-6-methoxyphenoxy) -2-phenylacetate To a stirred and cooled (0° C.) solution of 0.570 g (1.69 mmol) of the product of Step A dissolved in 6 mL of CH$_2$Cl$_2$ was added 0.702 g (2.11 mmol) of carbon tetrabromide and 0.555 g (2.11 mmol) of triphenylphosphine. After the addition the reaction mixture was allowed to warm to room temperature and was stirred 4 hours. The mixture was then evaporated in vacuo and purified on a silica gel flash chromatography of the product of Step A dissolved in 6 mL of CH$_2$Cl$_2$ was added 0.702 g the title compound.

$^1$H NMR (300 MHz, CDCl$_3$, ppm): δ3.75 (s, 3H), 3.80 (s, 3H), 4.35 (s, 2H), 5.65 (s, 1H), 6.80 (s, 1H), 6.95 (s, 1H), 7.30–7.40 (m, 3H), 7.50–7.60 (m, 2H).

FAB-MS: m/e 398,400, 402 (M+1).

Step C: Preparation of 3-[4-(1-carbomethoxy-1-phenylmethoxy)-3-chloro-5-methoxyphenylmethyl]-5,7-dimethyl-2-ethyl-3H -imidazo-[4,5-b]pyridine The product of Step B (0.126 g, 0.31 mmol) was used to alkylate 0.050 g (0.29 mmol) of 5,7-dimethyl-2-ethylimidazo[4,5-b]pyridine according to the procedure described for Step B of Example 2, which after purification afforded 0.092 g (65%) of the title compound.

$^1$H NMR (300 MHz, CDCl$_3$, ppm): a 1.20–1.30 (t, 3H), 2.55 (s, 3H), 2.60 (s, 3H), 2.70–2.80 (m, 2H), 3.65 (s, 3H), 3.70 (s, 3H), 5.30 (s, 2H), 5.70 (s, 1H) 6.63 (s, 1H), 6.68 (s, 1H), 6.90 (s, 1H), 7.25–7.35 (m, 3H), 7.45–7.55 (m, 2H).

FAB-MS: m/e 494, 496 (M+1).

Step D: Preparation of 3-[4-(1-carboxy-1-phenylmethoxy)-3-chloro-5-methoxyphenylmethyl]-5,7-dimethyl-2-ethyl-3H-imidazo[4,5-b]pyridine Using the general procedure for ester hydrolysis described in Step D of Example 2, 0.090 g (0.18 mmol) of the product of Step C was converted to 0.070 g (80%) of the title compound.

$^1$H NMR (300 MHz, CD$_3$OD, ppm): δ1.20–1.30 (t, 3H), 2.60 (s, 3H), :2.65 (s, 3H), 2.80–2.90 (m, 2H), 3.75 (s, 3H), 5.45 (s, 2H), 5.70 (s, 1H), 6.60 (s, 1H), 6.85 (s, 1H), 7.05 (s, 1H), 7.35–7.45 (m, 3H), 7.45–7.55 (m, 2H).

FAB-MS: m/e 480, 482 (M+1, 3:1 ratio).

EXAMPLE 5

3-[4-(1-Carboxy-1-phenylmethoxy)-3,5-dichlorophenylmethyl]-5,7-dimethyl -2-ethyl-3H-imidazo [4,5-b]pyridine Step A: Preparation of methyl 4-tert-butyldimethylsilyloxy-3,5-dichlorobenzoate To a solution of 10.00 g (45.2 mmol) of methyl 3,5-dichloro-4-hydroxybenzoate dissolved in 100 mL of CH$_2$Cl$_2$ was added 11.06 g (90.2 mmol) of 4-dimethylaminopyridine and 8.18 g (54.2 mmol) of tertbutyldimethylchlorosilane and the mixture was stirred under N$_2$ for 5 hours. The reaction mixture was then filtered and the filtrate was diluted with ethyl acetate. The solution was washed with water, 1N HCl, saturated NaHCO$_3$, dried (MgSO$_4$), filtered and evaporated. The residue was purified on a silica gel flash chromatography column eluted with 5% ethyl acetate/hexane to afford 7.70 g (51%) of the title compound.

$^1$H NMR (300 MHz, CDCl$_3$, ppm): d 0.30 (s, 6H), 1.00 (s, 9H), 3.90 (s, 3H), 7.95 (s, 2H).

FAB-MS: m/e 335, 337, 339 (M+1).

Step B: Preparation of 4-tert-butyldimethylsilyloxy-3,5-dichlorobenzyl alcohol

To a stirred and cooled (0° C.) solution of 7.70 g (23.0 mmol) of the product of Step A dissolved in 50 mL of anhydrous THF was added 23.0 mL (23.0 mmol) of a 1M solution of lithium aluminum hydride in THF. After the addition was complete the reaction mixture was allowed to warm to room temperature and stirred 3.5 hours. The stirred reaction was then quenched by dropwise addition of 0.88 mL water, then 0.88 mL of 15% NaOH, and finally 2.62 mL water. The reaction mixture was then filtered and concentrated in vacuo. The residue was dissolved in ethyl acetate, washed with 1N HCl, sturated NaHCO$_3$, dried (MgSO$_4$), and evaporated in vacuo to afford 1.83 g (26%) of the title compound.

$^1$H NMR (300 MHz, CDCl$_3$, ppm): d 0.30 (s, 6H), 1.05 (s, 9H), 1.80 (br s, 1H), 4.55 (s, 2H), 7.22 (s, 2H).

FAB-MS: m/e 306 (M+1).

Step C: Preparation of 3,5-dichloro-4-hydroxybenzyl alcohol

To a solution of 1.83 g (5.96 mmol) of the product of Step B dissolved in 6 mL of THF was added 5.96 mL (5.96 mmol) of a 1M solution of tetra-n-butylammonium fluoride in THF and the reaction mixture was stirred at room temperature 30 minutes. The solution was then evaporated in vacuo and the residue was purified on a silica gel flash chromatography column eluted with 4% methanol/chloroform to afford 0.733 g (64%) of the title compound.

$^1$H NMR (300 MHz, CDCl$_3$, ppm): a 1.90–4.10 (br, 2H) 4.60 (s, 2H), 7.27 (s, 2H).

FAB-MS: m/e 192 (M+1).

Step D: Preparation of methyl 2-(2,6-dichloro-4-hydroxymethylphenoxy)-2-phenylacetate Using the K$_2$CO$_3$/acetone conditions for phenol alkylation described in Step A of Example 4, 0.400 g (2.07 mmol) of the product of Step C was alkylated with 0.522 g (2.28 mmol) of methyl 2-bromophenylacetate to afford 0.144 g (20%) of the title compound.

$^1$H NMR (300 MHz, CDCl$_3$, ppm): δ1.70–1.80 (t, 3H), 3.75 (s, 3H), 4.55 (d, 2H), 5.75 (s, 1H), 7.22 (s, 2H), 7.30–7.40 (m, 3H), 7.45–7.55 (m, 2H).

FAB-MS: m/e 341,343,345 (M+1, 10:6:1 ratio).

Step E: Preparation of methyl 2-(4-bromomethyl-2,6-dichlorophenoxy)-2-phenylacetate To a stirred and cooled (0° C.) solution of 0.140 g (0.41 mmol) of the product of Step D dissolved in 2 mL of CH$_2$Cl$_2$ was added 0. 170 g (0.51 mmol) of carbon tetrabromide and 0.135 g (0.51 mmol) of triphenylphosphine. After the addition the reaction mixture was allowed to warm to room temperature and was stirred overnight. The mixture was then evaporated in vacuo and purified on a silica gel flash chromatography of the product of Step D dissolved in 2 mL of CH$_2$Cl$_2$ was added 0. 170 g the title compound.

$^1$H NMR (300 MHz, CDCl$_3$, ppm): δ3.75 (s, 3H), 4.30 (s, 2H), 5.75 (s, 1H), 7.27 (s, 2H), 7.30–7.40 (m, 3H), 7.45–7.55 (m, 2H).

FAB-MS: m/e 405 (M+1).

Step F: Preparation of 3-[4-(1-carbomethoxy-1-phenylmethoxy)-3,5-dichlorophenylmethyl]-5,7-dimethyl-2-ethyl-3H-imidazo[4,5 -b]-pyridine The product of Step E (0.126 g, 0.31 mmol) was used to alkylate 0.050 g (0.29 mmol) of 5,7-dimethyl-2-ethylimidazo[4,5-b]pyridine according to the procedure described for Step B of Example 2, which after purification afforded 0.096 g (68%) of the title compound.

$^1$H NMR (300 MHz, CDCl$_3$, ppm): δ1.20–1.30 (t, 3H), 2.58 (s, 3H), 2.62 (s, 3H), 2.65–2.75 (m, 2H), 3.75 (s, 3H), 5.30 (s, 2H), 5.75 (s, 1H), 6.90 (s, 1H), 7.00 (s, 2H), 7.25–7.35 (m, 3H), 7.45–7.55 (m, 2H).

FAB-MS: m/e 498,500, 502 (M+1).

Step G: Preparation of 3-[4-(1-carboxy-1-phenylmethoxy)-3,5-dichlorophenylmethyl]-5,7-dimethyl-2-ethyl-3H-imidazo[4,5-b]pyridine Using the general procedure for ester hydrolysis described in Step D of Example 2, 0.092 g (0.18 mmol) of the product of Step F was converted to 0.080 g (90%) of the title compound.

$^1$H NMR (300 MHz, CD$_3$OD, ppm): a 1.20–1.30 (t, 3H), 2.61 (s, 3H), 2.65 (s, 3H), 2.80–2.95 (m, 2H), 5.45 (s, 2H), 5.65 (s, 1H), 7.05 (s, 2H), 7.25–7.35 (m, 3H), 7.45–7.55 (m, 2H).

FAB-MS: m/e 484, 486, 488 (M+1, 10:6:1 ratio).

EXAMPLE 6

3-[4-(1-Carboxy-1-phenylmethoxy)-2-chlorophenylmethyl]-5,7-dimethyl -2-ethyl-3H-imidazo[4,5-b]pyridine Step A: Preparation of methyl 2-(3-chloro-4-formylphenoxy)-2-phenylacetate Using the K$_2$CO$_3$/acetone conditions for phenol alkylation described in Step A of Example 4, 1.00 g (6.41 mmol) of 2-chloro-4-hydroxybenzaldehyde was alkylated with 1.61 g (7.05 mmol) of methyl 2-bromophenylacetate to afford 1.49 g (76%) of the title compound.

$^1$H NMR (300 MHz, CDCl$_3$, ppm): δ3.75 (s, 3H), 5.68 (s, 1H), 6.90 (d, 1H), 7.00 (s, 1H), 7.35–7.45 (m, 3H), 7.50–7.60 (m, 2H), 7.85 (d, 1H), 10.30 (s, 1H).

FAB-MS: m/e 305, 307 (M+1).

Step B: Preparation of methyl 2-(3-chloro-4-hydroxymethylphenoxy)-2-phenylacetate A stirred solution of 1.49 g (4.90 mmol) of the product of Step A dissolved in 20 mL of methanol was treated with 0.093 g (2.46 mmol) of sodium borohydride at room temperature. After 5 minutes the reaction mixture was partitioned between ethyl acetate and 1N hydrochloric acid, and the organic layer was separated. The product was washed with water, brine, dried (MgSO$_4$), filtered and evaporated in vacuo. The residue was purified on a silica gel flash chromatography column eluted with 25% ethyl acetate/hexane to afford 1.380 g (92%) of the title compound.

$^1$H NMR (400 MHz, CDCl$_3$, ppm): δ1.80–1.85 (t, 1H), 3.75 (s, 3HI, 4.70 (d, 2H), 5.60 (s, 1H), 6.85 (d, 1H), 7.00 (s, 1H), 7.30–7.45 (m, 4H), 7.50–7.60 (m, 2H).

Step C: Preparation of methyl 2-(4-bromomethyl-3-chlorophenoxy)-2-phenylacetate

To a stirred and cooled (0° C.) solution of 1.38 g (4.51 mmol) of the product of Step D dissolved in 18 mL of CH$_2$Cl$_2$ was added 1.87 g (5.64 mmol) of carbon tetrabromide and 1.48 g (5.64 mmol) of triphenylphosphine. After the addition the reaction mixture was allowed to warm to room temperature and was stirred 3 hours. The mixture was then evaporated in vacuo and purified on a silica gel flash chromatography of the product of Step D dissolved in 18 mL of CH$_2$Cl$_2$ was added 1.87 g title compound.

$^1$H NMR (400 MHz, CDCl$_3$, ppm): δ3.75 (s, 3H), 4.55 (s, 2H), 5.60 (s, 1H), 6.80 (d, 1H), 7.00 (s, 1H), 7.30 (d, 1H), 7.35–7.45 (m, 3H), 7.50–7.6 (m, 2H).

FAB-MS: m/e 369, 371, 373 (M+1).

Step D: Preparation of 3-[4-(1-carbomethoxy-1-phenylmethoxy)-2-chlorophenylmethyl]-5,7-dimethyl-2-ethyl-3H-imidazo[4,5-b]pyridine The product of Step C (0.116 g, 0.31 mmol) was used to alkylate 0.050 g (0.29 mmol) of 5,7-dimethyl-2-ethylimidazo[4,5-b]pyridine according to the procedure described for Step B of Example 2, which after purification afforded 0.094 g (69%) of the title compound.

$^1$H NMR (400 MHz, CDCl$_3$, ppm): δ1.20–1.30 (t, 3H), 2.55 (s, 3H), 2.62 (s, 3H), 2.65–2.75 (m, 2H), 3.70 (s, 3H), 5.45 (s, 2H), 5.55 (s, 1H), 6.45 (d, 1H), 6.65 (d, 1H), 6.90 (s, 1H), 7.05 (s, 1H), 7.35–7.40 (m, 3H), 7.45–7.5 (m, 2H).

FAB-MS: m/e 464, 466 (M+1, 3:1 ratio).

Step E: Preparation of 3-[4-(1-carboxy-1-phenylmethoxy)-2-chlorophenylmethyl]-5,7-dimethyl-2-ethyl-3H-imidazo[4,5-b]pyridine Using the general procedure for ester hydrolysis described in Step D of Example 2, 0.090 g (0.18 mmol) of the product of Step D was converted to 0.030 g (34%) of the title compound.

1H NMR (300 MHz, CD$_3$OD, ppm): δ1.25–1.35 (t, 3H), 2.60 (s, 3H), 2.65 (s, 3H), 2.80–2.90 (m, 2H), 5.55–5.65 (m, 3H), 6.50 (d, 1H), 5.85 (d, 1H), 7.05 (s, 1H), 7.15 (s, 1H), 7.35–7.45 (m, 3H), 7.55–7.65 (m, 2H).

FAB-MS: m/c 450, 452 (M+1, 3:1 ratio).

EXAMPLE 7

3-[4-(1-Carboxy-1-phenylmethoxy)-3-(2-propen-1-yl)phenylmethyl]-5,7-dimethyl-2-ethyl-3H-imidazo[4,5-b]pyridine Step A: Preparation of methyl 4-(2-propen-1-yl)oxybenzoate A 2 L flask was equipped with a mechanical stirrer, a reflux condenser and a stopper, then charged with 50.05 g (0.329 mol) of methyl 4-hydroxybenzoate, 960 mL of acetone, 22.50 g (1.625 mol) of anhydrous potassium carbonate, 80.5 mL (112.6 g, 0.932 mol) of allyl bromide and the mixture was stirred and refluxed for 14 hours. The mixture was cooled to room temperature, filtered and concentrated to an oil. The residual oil was purified by distillation (97° C. @0.03 mm Hg) to afford 53.52 g (86%) of the title compound.

$^1$H NMR (300 MHz, CDCl$_3$, ppm): δ3.84 (s, 3H), 4.56 (d, J=7 Hz, 2H), 5.28 (dd, J=3,12 Hz, 1H), 5.40 (dd, J=3,19 Hz, 1H), 5.96–6.1 (m, 1H), 6.90 (d, J=10 Hz, 2H), 7.96 (d, J=10 Hz, 2H).

FAB-MS: m/e 193 (M+1).

Step B: Preparation of methyl 4-hydroxy-3-(prop-2-en-1-yl)benzoate

A solution of 15.05 g (78.3 mmol) of the product of Step A in 25 mL of 1,2-dichlorobenzene was magnetically stirred and refluxed (183° C.) under an argon atmosphere for 18 hours. At this point, the reaction mixture was cooled to room temperature and applied to a 6 cm diameter by 18 cm silica gel flash chromatography column and eluted with 25% ethyl acetate-hexane to separate the 1,2-dichlorobenzene, then with 40% ethyl acetate-hexane to elute the product. The product fractions were concentrated in vacuo and the residual oil was crystallized from hexane to afford 13.70 g (91%) of the title compound.

$^1$H NMR (300 MHz, CDCl$_3$, ppm): δ3.42 (d, J=8 Hz, 2H), 3.88 (s, 3H), 5.14–5.20 (m, 2H), 5.48 (s, 1H), 5.94–6.06 (m, 1H), 6.82 (d, J=12 Hz, 1H), 7.80–7.85 (m, 2H).

FAB-MS: m/e 193 (M+1).

Step C: Preparation of methyl 4-(tert-butyldimethylsilyloxy)-3-(2-propen-1-yl)benzoate To a solution of 5.168 g (26.9 mmol) of the product of Step B in 50 mL of dichloromethane was added 4.40 mL (2.95 mmol) of triethylamine, 4.46 g (2.95 mmol) of tert-butyldimethylchlorosilane, 0.100 g of 4-dimethylaminopyridine, and the reaction mixture was stirred at room temperature for 2 hours. The mixture was then diluted with 50 mL dichloromethane, washed with 100 mL 1N hydrochloric acid, dried (MgSO$_4$), filtered and evaporated. The residual oil (7.993 g, 97%) was used in the next step without further purification.

$^1$H NMR (300 MHz, CDCl$_3$, ppm): δ0.24 (s, 6H), 1.02 (s, 9H), 3.36 (d, J=8 Hz, 2H), 3.84 (s, 3H), 4.98–5.08 (m, 2H), 5.88–6.03 (m, 1H), 6.78 (d, J=1 1 Hz, 1H), 7.76–8.40 (m, 2H).

FAB-MS: m/e 307 (M+1).

Step D: Preparation of 4-(tert-butyldimethylsilyloxy)-3-(2-propen-1-yl)benzyl alcohol To a magnetically stirred solution of 8.523 g (28.0 mmol) of the product from Step C in 35 mL of anhydrous THF was added 15.0 mL of a 1.0M solution of lithium aluminum hydride in THF, and the reaction mixture was stirred under a nitrogen atmosphere for 2 hours. At this point, the reaction was quenched by cautious addition of 10 mL water, the resulting precipitate was dissolved by addition of 1.0N hydrochloric acid and the product was extracted into ethyl acetate. The organic layer was separated, dried (MgSO$_4$), filtered and evaporated in vacuo to afford 7.258 g (93%) of the title compound.

$^1$H NMR (300 MHz, CDCl$_3$ ppm): δ0.20 (s, 6H) 1.00 (s, 9H), 3.34 (d, J=8 Hz, 2H), 3.84 (s, 1H), 4.57 (s, 2H), 4.97–5.07 (m, 2H), 5.88–6.03 (m, 1H), 6.86 (d, J=10 Hz, 1H), 7.05–7.14 (m, 2H).

FAB-MS: m/e 279, 261 (M+1).

Step E: Preparation of 4-(tert-butyldimethylsilyl)-3-(2-propen-1-yl)benzyl bromide To a magnetically stirred solution of 7.258 g (26 mmol) of the product from Step D and 10.281 g (31 mmol) of carbon tetrabromide in 50 mL of dry dichloromethane was slowly added 8.13 1 g (31 mmol) of triphenylphosphine at 0 ° C. under a nitrogen atmosphere. The reaction mixture was stirred 45 minutes and allowed to warm to room temperature. At this point, the reaction mixture was applied to a silica gel flash chromatography column and was eluted with dichloromethane. Evaporation of the product fractions and drying in vacuo afforded 7.651 g (86%) of the title compound as a viscous oil.

$^1$H NMR (300 MHz, CDCl$_3$, ppm): δ0.23 (s, 6H), 1.00 (s, 9H), 3.34 (d, J=8 Hz, 2H), 4.45 (s, 2H), 4.98–5.09 (m, 2H), 5.86–6.02 (m, 1H), 6.74 J=10 Hz, 1H), 7.08–7.16 (m, 2H).

FAB-MS: m/e 343, 341 (M+1).

Step F: Preparation of 3-[4-tert-butyldimethylsilyloxy-3-(2-propen-1-yl)phenylmethyl]-5,7-dimethyl-2-ethyl-3H-imidazo-[4,5-b]pyridine To a solution of 1.029 g (5.9 mmol) of 5,7-dimethyl-2-ethylimidazo[4,5-b]pyridine dissolved in 10 mL of dry DMF was added 0.258 g (6.5 mmol) of a 60% oil dispersion of sodium hydride and the reaction mixture was stirred under a nitrogen atmosphere for 1 hour. At this point, hydrogen evolution had ceased, and a solution of 2.210 g of the product of Step E dissolved in 2.0 mL of dry DMF was added via syringe. The reaction was stirred an additional 2 hours at room temperature and then partitioned between ethyl acetate and water. The organic layer was extracted, washed with brine, dried (MgSO$_4$), filtered and evaporated. The residual oil was purified on a silica gel flash chromatography column eluted with 50% ethyl acetate-hexane. Evaporation of the purified fraction and drying in vacuo afforded 1.519 g (59%) of the title compound.

$^1$H NMR (300 MHz, CDCl$_3$, ppm): δ0.16 (s, 6H), 0.96 (s, 9H), 1.27 (t, J=9 Hz, 3H), 2.57 (s, 3H), 2.60 (s, 3H), 2.76 (q, J=9 Hz, 2H), 3.28 (d, J=8 Hz, 2H), 4.93–5.03 (m, 2H), 5.33 (s, 2H), 5.81–5.95 (m, 1H), 6.64 (d, J=10 Hz, 1H), 6.76 (dd, J=3, 10 Hz, 1H), 6.86 (s, 1H), 7.00 (d, J=3 Hz, 1H).

FAB-MS: m/e 436 (M+1).

Step G: Preparation of 5,7-dimethyl-2-ethyl-3-[4-hydroxy-3-(2-propen-1-yl)phenylmethyl]-3H-imidazo[4,5-b]pyridine To a solution of 1.519 g (3.48 mmol) of the product of Step F in 8.0 mL of anhydrous THF was added 3.6 mL of a 1.0M solution of tetra-n-butyl-ammonium fluoride in THF and the reaction mixture was stirred for 2.5 hours at room temperature. The reaction mixture was then evaporated in vacuo and the residual oil was chromatographed on a silica gel flash chromatography column eluted with ethyl acetate. The purified fractions were combined, evaporated and dried in vacuo to afford the title compound.

$^1$H NMR (300 MHz, CDCl$_3$, ppm): δ1.24 (t, J=9 Hz, 3H), 2.57 (s, 3H), 2.60 (s, 3H), 2.73 (q, J=9 Hz, 2H), 3.31 (d, J=8 Hz, 2H), 5.03–5.10 (m, 2H), 5.33 (s, 2H), 5.88–6.02 (m, 1H), 6.36 (d, J=10 Hz, 1H), 6.48 (dd, J=3,10 Hz, 1H), 6.84–6.89 (m, 2H), 7.37 (br s, 1H).

FAB-MS: m/e 322 (M+1).

Step H: Preparation of 3-[4-(1-carbomethoxy-1-phenyl-methoxy)-3-(2-propen-1-yl)phenylmethyl]-5,7-dimethyl-2-ethyl-3H-imidazo[4,5-b]pyridine To a solution of 0.17 1 g (0.53 mmol) of the product of Step G dissolved in 2.5 mL of anhydrous DMF was added 0.023 g (0.58 mmol) of a 60% oil dispersion of sodium hydride and the reaction mixture was stirred under a nitrogen atmosphere for 30 minutes at room temperature. A solution of 0.134 g of methyl α-bromophenylacetate in 1.0 mL of DMF was then added via syringe and the reaction mixture was stirred an additional 1.5 hours. The reaction mixture was then partitioned between ethyl acetate and water, the organic layer was separated, dried (MgSO$_4$), filtered and evaporated. The residual oil was purified on a silica gel flash chromatography column eluted with 75% ethyl acetate-hexane to afford after evaporation of the purified fractions and drying in vacuo 0.212 g (85%) of the title compound.

$^1$H NMR (300 MHz, CDCl$_3$, ppm): δ1.26 (t, J=9 Hz, 3H), 2.57 (s, 3H), 2.60 (s, 3H), 2.76 (q, J=9 Hz, 2H), 3.45 (d, J=8 Hz, 2H), 3.66 (s, 3H), 4.99–5.07 (m, 2H), 5.34 (s, 2H), 5.57 (s, 1H), 5.88–6.04 (m, 1H), 6.59 (d, J=10 Hz, 1H), 6.79 (dd, J=3,10 Hz, 1H), 6.86 (s, 1H), 7.05 (d, J=3 Hz, 1H), 7.30–7.40 (m, 3H), 7.48–7.56 (m, 2H).

FAB-MS: m/e 470 (M+1).

Step I: Preparation of 3-[4-(1-carboxy-1-phenylmethoxy)-3-(2-propen-1-yl)phenylmethyl]-5,7-dimethyl-2-ethyl-3H-imidazo[4,5-b]pyridine To a solution of 0.141 g (0.30 mmol) of the product of Step H dissolved in 2.0 mL of methanol was added 0.25 mL of a 1.0N solution of sodium hydroxide and the reaction was stirred at room temperature for 2 hours. The reaction mixture was then adjusted to pH 7 with 1.0N hydrochloric acid and then partitioned between ethyl acetate and water. The organic layer was separated, dried (MgSO$_4$), filtered, evaporated and then purified on a silica gel flash chromatography column eluted with chloroform-methanol-conc. ammonium hydroxide (80:15:1). Evaporation of the purified fractions and drying in vacuo afforded 0.092 g (69%) of the title compound as a white amorphous solid.

$^1$H NMR (300 MHz, CD$_3$OD, ppm): δ1.27 (t, J=9 Hz, 3H), 2.61 (s, 3H), 2.64 (s, 3H), 2.89 (q, J=9 Hz, 2H), 3.40–3.52 (m, 2H), 4.95–5.06 (m, 2H), 5.53 (s, 2H), 5.73 (s, 1H), 5.94–6.13 (m, 1H), 6.84 (d, J=10 Hz, 1H), 6.95 (dd, J=3,10 Hz, 1H), 7.06 (br s, 2H), 7.36–7.44 (m, 3H), 7.57–7.64 (m, 2H).

FAB-MS: m/e 456 (M+1).

EXAMPLE 8

3-[4-(1-Carboxy-1-phenylmethoxy)-3-propylphenylmethyl]-5,7-dimethyl-2-ethyl -3H-imidazo[4,5-b]pyridine Step A: Preparation of 5,7-dimethyl-2-ethyl-3-[4-hydroxy-3-propylphenylmethyl]-3H-imidazo[4,5-b]pyridine A solution of 0.255 (0.79 mmol) of the product of Example 7, Step G in 10 mL ethanol was placed in a small Parr hydrogenation flask and 50 mg of a 10% palladium on carbon catalyst was added. The reaction mixture was then shaken in a Parr apparatus under a 45 psig hydrogen atmosphere for 1 hour at room temperature. The reaction mixture was then removed from the flask, filtered, evaporated and dried in vacuo to afford 0.239g (93%) of the title compound which was used in the next step without further purification.

$^1$H NMR (300 MHz, CDCl$_3$, ppm): δ0.90 (t, J=9 Hz, 3H), 1.24 (t, J=10 Hz, 3H), 1.50–1.62 (m, 2H), 2.48 (t, J=8 Hz, 2H), 2.56 (s, 3H), 2.59 (s, 3H), 2.72 (q, J=9 Hz, 2H), 5.32 (s, 3H), 6.23 (d, J=10 Hz, 1H), 6.38 (dd, J=3,10 Hz, 1H), 6.79 (d, J=3 Hz, 1H), 6.87 (s, 1H), 7.68 (br s, 1H).

FAB-MS: m/e 324 (M+1).

Step B: Preparation of 5,7-dimethyl-2-ethyl-3-[4-(1-carbomethoxy-1-phenylmethoxy)-3-propylphenylmethyl]-3H-imidazo-[4,5-b]pyridine To a solution of 0.062 g (0.19 mmol) of the product of Step A in 1.5 mL of anhydrous DMF was added 8.4 mg of a 60% oil dispersion of sodium hydride and the reaction mixture was stirred under a nitrogen atmosphere. After the reaction mixture had stirred 30 minutes at room temperature, hydrogen evolution had ceased, and a solution of 0.048 g of methyl 2-bromophenylacetate in 0.5 mL of dry DMF was added via syringe. The reaction mixture was stirred an additional 1.5 hours and then partitioned between ethyl acetate and water. The organic layer was separated, washed with brine, dried (MgSO$_4$), filtered, evaporated and then chromatographed on a silica gel flash chromatography column eluted with 50% ethyl acetate-hexane. The purified fractions were combined, evaporated and dried in vacuo to afford 59 mg (66%) of the title compound as a viscous oil.

$^1$H NMR (300 MHz, CDCl$_3$, ppm): δ0.90 (t, J=9 Hz, 3H), 1.25 (t, J=9 Hz, 3H), 1.54–1.68 (m, 2H), 2.56–2.66 (m, 2H), 2.58 (s, 3H), 2.62 (s, 3H), 2.76 (q, J=9 Hz, 2H), 3.66 (s, 3H), 5.35 (s, 2H), 5.57 (s, 1H), 6.59 (d, J=10 Hz, 1H), 6.81 (dd, J=3,10 Hz, 1H), 6.87 (s, 1H), 6.99 (d, J=3 Hz, 1H), 7.28–7.40 (m, 3H), 7.49–7.56 (m, 2H).

FAB-MS: m/e 472 (M+1).

Step C: Preparation of 3-[4-(1-carboxy-1-phenylmethoxy)-3-propylphenylmethyl]-5,7-dimethyl-2-ethyl-3H-imidazo-[4,5-b]pyridine To a solution of 0.042 g (0.09 mmol) of the product of Step B dissolved in 1.0 mL of methanol was added 0.1 mL of a 1.0N solution of sodium hydroxide and the reaction mixture was stirred for 3 hours at room temperature. The reaction mixture was then adjusted to pH 7 with 1.0N hydrochloric acid and then partitioned between ethyl acetate and water. The organic layer was separated, dried (MgSO4), filtered, evaporated and then purified on a silica gel flash chromatography column eluted with chloroform-methanol-conc. ammonium hydroxide (80:15:1). Evaporation of the purified fractions and drying in vacuo afforded 0.21 g (51%) of the title compound as a white amorphous solid.

$^1$H NMR (300 MHz, CD$_3$OD, ppm): δ0.90 (t, J=8 Hz, 3H), 1.26 (t, J=9 Hz, 3H), 1.53–1.67 (m, 2H), 2.61 (s, 3H), 2.65 (s, 3H), 2.66–2.80 (m, 2H), 2.86 (q, J=8 Hz, 2H), 5.49 (s, 2H), 5.54 (s, 1H), 6.80 (d, J=10 Hz, 1H), 6.90 (dd, J=2, 10 Hz, 1H), 6.98 (d, J=2 Hz, 1H), 7.06 (s, 1H), 7.30–7.44 (m, 3H), 7.60–7.66 (m, 2H).

FAB-MS: m/e 458 (M+1).

EXAMPLE 9

3-[4-(1-Carboxy-1-(2-methylphenyl)methoxy)-3-propylphenylmethyl]-5,7-dimethyl-2-ethyl-3H-imidazo[4,5-b]pyridine Step A: Preparation of 3-[4-(1-carbomethoxy-1-(2-methylphenyl)methoxy)-3-propylphenylmethyl]-5,7-dimethyl-2-ethyl-3H-imidazo[4,5-b]pyridine To a suspension of 5.9 mg (2.45 mmol) of a 60% oil dispersion of NaH in 0.8 mL of DMF was added 0.066 g (0.20 mmol) of 5,7-dimethyl-2-ethyl-3-[4-hydroxy-3-propylphenylmethyl]-3H-imidazo[4,5-b]pyridine (Example 8, Step A) and the mixture was stirred at room temperature. After 20 minutes, a solution of 0.060 g (2.45 mmol) of methyl 2-bromo-2'-methylphenylacetate dissolved in 0.5 mL of DMF was added and the reaction mixture was stirred an additional 15 hours. The reaction was then partitioned between ethyl acetate and water, the organic layer was separated, washed with water, dried (MgSO4), filtered and evaporated in vacuo. The residue was purified on a silica gel flash chromatography column eluted with 50% ethyl acetate/hexane to afford 0.082 g (83%) of the title compound.

$^1$H NMR (300 MHz, CDCl$_3$, ppm): δ0.90 (t, J=9 Hz, 3H), 1.25 (t, J=8 Hz, 3H), 1.50–1.65 (m, 2H), 2.44 (s, 3H), 2.56 (s, 3H), 2.60 (s, 3H), 2.52–2.6 (m, 2H), 2.75 (q, J=8 Hz, 2H), 3.67 (s, 3H), 5.34 (s, 2H), 5.74 (s, 1H), 6.55 (d, J=10 Hz, 1H), 6.78 (dd, J=2, 10 Hz, 1H), 6.86 (s, 1H), 6.98 (d, J=2 Hz, 1H), 7.15–7.28 (m, 3H), 7.50–7.56 (m, 1H).

FAB-MS: m/e 486 (M+1).

Step B: Preparation of 3-[4-(1-carboxy-1-(2-methylphenyl)methoxy) -3-propylphenylmethyl]-5,7-dimethyl-2-ethyl-3H-imidazo[4,5-b]pyridine Using the general procedure for ester hydrolysis described in Step D of Example 2, 0.076 g (0.16 mmol) of the product of Step A was converted to 0.040 g (54%) of the title compound.

$^1$H NMR (300 MHz, CD$_3$OD, ppm): δ0.88 (t, J=9 Hz, 3H), 1.27 (t, J=8 Hz, 3H), 1.50–1.65 (m, 2H), 2.49 (s, 3H), 2.62 (s, 3H), 2.65 (s, 3H), 2.55–2.70 (m, 2H), 2.88 (q, J=8 Hz, 2H), 5.48 (s, 2H), 5.83 (s, 1H), 6.78 (d, J=10 Hz, 1H), 6.90 (dd, J=2,10 Hz, 1H), 6.99 (d, J=2 Hz, 1H), 7.06 (s, 1H), 7.20–7.27 (m, 3H), 7.54–7.60 (m, 1H).

FAB-MS: m/e 472 (M+1).

EXAMPLE 10

3-[4-(1-Carboxy-1-(2-chlorophenyl)methoxy)-3-propylphenylmethyl]-5,7-dimethyl-2-ethyl-3H-imidazo[4,5-b]pyridine Step A: Preparation of 3-[4-(1-carbomethoxy-1-(2-chlorophenyl)methoxy) -3-propylphenylmethyl]-5,7-dimethyl-2-ethyl-3H-imidazo[4,5-b]pyridine To a suspension of 6.3 mg (2.63 mmol) of a 60% oil dispersion of NaH in 1.0 mL of DMF was added 0.071 g (0.22 mmol) of 5,7-dimethyl-2-ethyl-3-[4-hydroxy-3-propylphenyl]methyl-3H-imidazo 4,5-b]pyridine (Example 8, Step A) and the mixture was stirred at room temperature. After 20 minutes, a solution of 0.069 g (0.26 mmol) of methyl 2-bromo-2'-chlorophenylacetate dissolved in 0.75 mL of DMF was added and the reaction mixture was stirred an additional 2 hours. The reaction was then partitioned between ethyl acetate and water, the organic layer was separated, washed with water, dried (MgSO4), filtered and evaporated in vacuo. The residue was purified on a silica gel flash chromatography column eluted with 50% ethyl acetate/hexane to afford 0.098 g (88%) of the title compound.

$^1$H NMR (300 MHz, CDCl$_3$, ppm): δ0.89 (t, J=9 Hz, 3H), 1.26 (t, J=8 Hz, 3H), 2.55 (s, 3H), 2.59 (s, 3H), 2.52–2.63 (m, 2H), 2.74 (q, J=8 Hz, 2H), 3.70 (s, 3H), 5.34 (s, 2H), 6.03 (s, 1H), 6.62 (d, J=10 Hz, 1H), 6.78 (dd, J=2,10 Hz, 1H), 6.86 (s, 1H), 6.97 (d, J=2 Hz, 1H), 7.24–7.32 (m, 2H), 7.34–7.42 (m, 1H), 7.57–7.64 (m, 1H).

FAB-MS: m/e 506 (M+1).

Step B: Preparation of 3-[4-(1-carboxy-1-(2-chlorophenyl)methoxy)-3-propylphenylmethyl]-5,7-dimethyl-2-ethyl-3H-imidazo[4,5-b]pyridine Using the general procedure for ester hydrolysis described in Step D of Example 2, 0.098 g (0.19 mmol) of the product of Step A was converted to 0.072 g (76%) of the title compound.

$^1$H NMR (300 MHz, CD$_3$OD, ppm): δ0.85 (t, J=9 Hz, 3H), 1.25 (t, J=8 Hz, 3H), 1.60–1.74 (m, 2H), 2.61 (s, 3H), 2.64 (s, 3H), 2.52–2.60 (m, 2H), 2.88 (q, J=8 Hz, 2H), 5.49 (s, 2H), 6.04 (s, 1H), 6.80 (d, J=10 Hz, 1H), 6.92 (dd, J=2, 10 Hz, 1H), 6.98 (d, J=2 Hz, 1H), 7.06 (s, 1H), 7.33–7.39 (m, 2H), 7.44–7.50 (m, 1H), 7.64–7.70 (m, 1H).

FAB-MS: m/e 492 (M+1).

EXAMPLE 11

3-[4-((1-Carboxy-1-phenyl)methoxy)-3-(1-methylcyclohex-1- yl)phenylmethyl]-5,7 -dimethyl-2-ethyl-3H-imidazo[4,5-b]pyridine Step A: Preparation of methyl 2-(2-(1-methylcyclohex-1-yl)-4-methylphenoxy) -2-phenylacetate Using the K$_2$CO$_3$/acetone conditions for phenol alkylation described in Step A of Example 4, 0.496 g (2.43 mmol) of 2-(1-methylcyclohex-1-yl) -4-methylphenol was alkylated with 0.834 g (3.64 mmol) of methyl 2-bromophenylacetate to afford 0.780 g (91%) of the title compound.

$^1$H NMR (300 MHz, CDCl$_3$, ppm): δ1.41 (s, 3H), 1.36–1.80 (m, 8H), 2.20–2.34 (m, 2H), 2.27 (s, 3H), 3.70 (s, 3H), 5.64 (s, 1H), 6.70 (d, J=10 Hz, 1H), 6.87 (dd, J=2, 10 Hz, 1H), 7.16 (d, J=2 Hz, 1H), 7.32–7.44 (m, 3H), 7.55–7.63 (m, 2H).

FAB-MS: m/e 353 (M+1).

Step B: Preparation of methyl 2-(4-bromomethyl-2-(1-methylcyclohex -1-yl)phenoxy)-2-phenylacetate To a solution of 0.780 g (2.21 mmol) of the product of Step A dissolved in 12 mL of CCl4 was added 0.394 g (2.21 mmol) of N-bromosuccinimide and 20 mg (catalytic amount) of AIBN. The mixture was stirred and refluxed under a N2 atmosphere for 6 hours. The mixture was then cooled, filtered and evaporated in vacuo. The residue was purified on a silica gel flash chromatography column eluted with 7% ethyl acetate/hexane to afford 0.203 g (21%) of the title compound.

$^1$H NMR (300 MHz, CDCl3, ppm): δ1.36 (s, 3H), 1.34–1.80 (m, 8H), 2.18–2.30 (m, 2H), 3.70 (s, 3H), 4.46 (s, 2H), 5.65 (s, 1H), 6.71 (d, J=10 Hz, 1H), 7.10 (dd, J=2, 10 Hz, 1H), 7.35 (d, J=2 Hz, 1H), 7.32–7.44 (m, 3H), 7.50–7.58 (m, 2H).

FAB-MS: m/e 433 (M+1).

Step C: Preparation of 3-[4-(1-carbomethoxy-1-phenyl-methoxy)-3-(1-methylcyclohex -1-yl)phenylmethyl]-5,7-dimethyl-2-ethyl-3H-imidazo[4,5-b]pyridine To a suspension of 18 mg (0.47 mmol) of a 60% oil dispersion of NaH in 1.0 mL of DMF was added 0.083 g (0.47 mmol) of 5,7-dimethyl -2-ethyl-3-[4-hydroxy-3-propylphenylmethyl]-3H-imidazo[4,5-b]pyridine (Example 43, Step A) and the mixture was stirred at room temperature. After 20 minutes, a solution of 0.203 g (0.47 mmol) of the product of Step B dissolved in 0.75 mL of DMF was added and the reaction mixture was stirred an additional 2 hours. The reaction was then partitioned between ethyl acetate and water, the organic layer was separated, washed with water, dried (MgSO4), filtered and evaporated in vacuo. The residue was purified on a silica gel flash chromatography column eluted with 50% ethyl acetate/hexane to afford 0.097 g (39%) of the title compound.

$^1$H NMR (300 MHz, CDCl3, ppm): δ1.28 (t, J=8 Hz, 3H), 1.33 (s, 3H), 1.20–1.70 (m, 8H), 2.13–2.24 (m, 2H), 2.55 (s, 3H), 2.60 (s, 3H), 2.82 (q, J=8 Hz, 2H), 3.66 (m, 3H), 5.34 (s, 2H), 5.58 (s, 1H), 6.53 (d, J=10 Hz, 1H), 6.77 (dd, J=2, 10 Hz, 1H), 6.85 (s, 1H), 7.26–7.40 (m, 4H), 7.50–7.58 (m, 2H).

FAB-MS: m/e 526 (M+1).

Step D: Preparation of 3-[4-(1-carboxy-1-phenylmethoxy)-3-(1-methylcyclohex-1-yl)phenylmethyl]-5,7-dimethyl-2-ethyl-3H -imidazo-[4,5 -b]-pyridine Using the general procedure for ester hydrolysis described in Step E of Example 19, 0.097 g (0.18 mmol) of the product of Step C was converted to 0.056 g (59%) of the title compound.

$^1$H NMR (300 MHz, CD3OD, ppm): δ1.01 (t, J=8 Hz, 1H), 1.34 (s. 3H), 1.20–1.70 (m, 8H), 2.08–2.20 (m, 2H), 2.40 (s, 3H), 2.54 (s, 3H), 2.88 (q, J=8 Hz, 2H), 5.25 (d, J=16 Hz, 1H), 5.37 (d, J=16 Hz, 1H), 5..60 (s, 1H), 6.73–6.86 (m, 3H), 7.32–7.47 (m, 4H), 7.64–7.74 (m, 2H).

FAB-MS: m/e 512 (M+1).

EXAMPLE 12

3 -[4-(1-Carboxy-1-(4-chlorophenyl)methoxy)-3 -propylphenylmethyl]-5.7-dimethyl-2-ethyl-3H-imidazo[4,5-b]pyridine Step A: Preparation of 3-[4-(1-carbomethoxy-1-(4-chlorophenyl)methoxy) -3-propyl-phenylmethyl]-5,7-dimethyl-2-ethyl-3H-imidazo [4,5-b]pyridine Using the K2CO3/acetone conditions for phenol alkylation described in Step A of Example 4; 5,7-dimethyl-2-ethyl-3-[4-hydroxy-3-propylphenyl methyl]-3H-imidazo[4,5-b]pyridine (Step A, Example 8) was alkylated with methyl 2-bromo-2-(4-chlorophenyl)acetate. Standard workup and purification by flash chromatography afforded a 50% yield of the title compound.

$^1$H NMR (200 MHz, CDCl3, ppm): δ7.49 (d, 2H), 7.36 (d, 2H), 7.02 (d, 1H), 6.90 (s, 1H), 6.82 (dd, 1H), 6.57 (d, 1H), 5.54 (s, 1H), 5.38 (br s, 2H), 3.67 (s, 3H), 2.86 (q, 2H), 2.66 (s, 3H), 2.6 (s, 3H), 2.5 (t, 2H), 1.7–1.5 (m, 2H), 1.15 (t, 3H), 0.9 (t, 3H).

FAB-MS: m/e 506 (M+1).

Step B: Preparation of 3-[4-(1-carboxy-1-(4-chlorophenyl)methoxy) -3-propylphenylmethyl]-5,7-dimethyl-2-ethyl-3H-imidazo-[4,5-b]pyridine Using the general procedure for ester hydrolysis described in Step D of Example 2, the product of Step A was converted to the title compound in 77% yield.

$^1$H NMR (200 MHz, CDCl3, ppm): δ7.56 (d, 2H), 7.25 (d, 2H), 7.15 (d, 1H), 6.988 (d, 2H), 6.8 (br s, 1H), 5.44 (s, 1H), 5.41 (s, 2H), 2.9–2.72 (q, 2H), 2.6 (s, 3H), 2.56 (s, 3H), 2.3–1.95 (br m, 2H), 1.65–1.44 (m, 2H), 1.27 (t, 3H), 0.84 (t, 3H).

FAB-MS: m/e 492 (M+1), 530 (M+K).

EXAMPLE 13

3-[4-(1-Carboxy-1-phenylmethoxy)-3,5-dipropyl-phenylmethyl]-5,7-dimethyl-2-ethyl-3H-imidazo[4,5-b]pyridine Step A: Preparation of methyl 3-(2-propen-1-yl)-4-(2-propen-1-yloxy)benzoate A solution of 3.04 g (15.8 mmol) of methyl 4-hydroxy-3-propenylbenzoate (Example 7, Step B) was refluxed with anhydrous potassium carbonate (4.37 g, 2 equiv) and allyl bromide (3.5 mL. 2.5 equiv) in acetone overnight. The mixture was filtered through celite and the filter cake was washed with more acetone and dichloromethane. After removing the solvents, the resulting oil was distilled under high vacuum to give 3.2 g (87%) of the title compound.

$^1$H NMR (400 MHz, CDCl3, ppm): δ7.87 (dd, 1H), 7.83 (d, 1H), (6.83 (d, 1H), 6.07–5.92 (m, 2H), 5.41 (dd, 1H), 5.27 (dd, 1H), 5.07 (dd, 1H), 5.05 (dd, 1H), 4.58 (d, 2H), 3.83 (s, 3H), 3.4 (d, 2H).

Step B: Preparation of methyl 4-hydroxy-3,5-di(2-propen-1-yl)benzoate

The product of Step A (3.2g, 13.8 mmol) was refluxed in 12-dichlorobenzene for 3 days in the presence of a catalytic amount of BHT (10 mg). Flash column chromatography of the mixture using hexane and then 10% and 20% ethyl acetate in hexane afforded 3.1 g (97%) of the title compound.

$^1$H NMR (200 MHz, CDCl3, ppm): δ7.73 (s, 2H), 6.12–5.92 (m, 2lt), 5.63 (s, 1H), 5.21 (dd, 2H), 5.15 (dd, 2H), 3.87 (s, 3H), 3.43 (dd, 4H).

FAB-MS: m/e 232 (M+1).

Step C: Preparation of methyl 4-tert-butyldimethyl-silyloxy-3,5-di(2-propen-1-yl)benzoate The product of Step B (3.1 g, 13.36 mmol) was treated with tert-butyldimethylsilyl chloride (2.22 g, 1.1 equiv), triethylamine (3 mL) and DMAP (0.1 equiv) in dichloromethane overnight. The mixture was concentrated and flash chromatographed with 5% and then 10% ethyl acetate in hexane to furnish 4.5 g (97%) of the title compound.

$^1$H NMR (200 MHz, CDCl3, ppm): δ7.72 (s, 2H), 6.02–5.30 (m, 2H), 5.12 (dd, 2H), 5.07 (dd, 2H), 3.86 (s, 3H), 3.38 (dd, 4H, 7 Hz), 1.02 (s, 9H), 0.21 (s, 6H).

Step D: Preparation of methyl 4-tert-butyldimethylsilyloxy-3,5-dipropylbenzoate A solution of 5.0 g (14.45 mmol) of the product of Step C in 250 mL ethanol containing 5% Rh/C (0.25 g) was shaken under a 40 psi pressure of hydrogen. Upon completion of reduction, the mixture was filtered through Celite, the filter cake was washed with methanol and dichloromethane. Removal of solvents afforded 4.55 g (90%) of the title compound.

$^1$H NMR (200 MHz, CDCl$_3$, ppm): δ7.66 (s, 2H), 3.84 (s, 3H), 2.54 (dd, 4H, 7.91 Hz, 7.41 Hz), 1.56 (sextet, 4H), 0.98 (s, 9H), 0.899 (t, 6H), 0.18 (s, 6H).

Step E: Preparation of 4-tert-butyldimethylsilyloxy-3,5-dipropylbenzyl alcohol Lithium aluminum hydride (9 mL of a 1M solution in THF) was added cautiously to a solution of the product of Step D at 0° C., and the reaction mixture was stirred overnight. Ethyl acetate was added to the mixture, cooled to 0° C. and treated with cold 1N HCl. After separating the organic phase, the aqueous phase was extracted with a mixture of ethyl acetate-ether-dichloromethane. The combined organic extracts were dried and concentrated. The concentrated material was purified by flash column chromatography using 20% ethyl acetate in hexane to afford 4.2 g (92%) of the title compound.

$^1$H NMR (400 MHz, CDCl$_3$, ppm): δ6.95 (s, 2H), 4.54 (s, 2H), 2.52 (dd, 4H), 1.55 (sextet, 4H), 0.99 (s, 9H), 0.90 (t, 6H), 0.16 (s, 6H).

Step F: Preparation of 3-[4-tert-butyldimethylsilyloxy-3,5-dipropylphenylmethyl]-5,7-dimethyl-2-ethyl-3H-imidazo-[4,5-b]pyridine To a solution of 4.2 g (13.0 mmol) of the product of Step E, 2.5 g (14.0 mmol) of 5,7-dimethyl-2-ethylimidazo[4,5-b]pyridine and 5.62 (20.0 mmol) of triphenylphosphine dissolved in 40 mL of THF, was added 3.396 g (20.0 mmol) of diethyl azodicarboxylate and the mixture was stirred for 1 hour. The reaction mixture was then concentrated in vacuo and the residual oil was purified on a silica gel flash chromatography column eluted with 25–40% ethyl acetate/hexane to afford 5 g (80%) of the title compound.

$^1$H NMR (400 MHz, CDCl$_3$, ppm): δ6.84 (s, 1H), 6.71 (s, 2H), 5.29 (s, 2H), 2.75 (q, 2H), 2.57 (s, 3H), 2.55 (s, 3H), 2.4 (dd, 4H), 1.42 (sextet, 4H), 1.27 (t, 3H), 0.94 (s, 9H), 0.8 (t, 6H), 0.10 (s, 6H).

Step G: Preparation of 5,7-dimethyl-2-ethyl-3-[4-hydroxy-3,5-dipropylphenylmethyl]-3H-imidazo[4,5-b]pyridine A THF solution of 5.0 g (10.44 mmol) of the product of Step F was treated with tetrabutylammonium fluoride (1.2 equiv, 1M solution in THF) overnight. THF was removed in vacuo and the residue was flash chromatographed using 30–50% ethyl acetate in hexane as eluent to afford 3.35 g (88%) of the title compound.

$^1$H NMR (400 MHz, CDCl$_3$, ppm): δ6.86 (s, 1H), 6.81 (s, 1H), 6.73 (s, 2H), 5.37 (s, 1H), 5.30 (s, 2H), 2.76 (q, 2H), 2.6 (s, 3H), 2.56 (s, 3H), 2.44 (dd, 4H), 1.52 (sextet, 4H), 1.23 (t, 3H), 0.88 (t, 6H).

Step H: Preparation of 3-[4-(1-carbomethoxy-1-phenylmethoxy)-3,5-dipropylphenylmethyl]-5,7-dimethyl-2-ethyl-3H-imidazo-[4,5-b]pyridine To a solution of (4.72 mmol) of the product of Step G and (5.19 mmol) of methyl 2-bromophenylacetate in 10 mL of acetone was added (9.44 mmol) of K$_2$CO$_3$ and the mixture was stirred and refluxed for 14 hours. The mixture was cooled, filtered and evaporated in vacuo and the residue was purified on a silica gel flash chromatography column to afford a 96% yield of the title compound.

$^1$H NMR (400 MHz, CDCl$_3$, ppm): δ7.44–7.42 (m, 2H), 7.37–7.31 (m, 3H), 6.88 (s, 1H), 6.74 (s, 2H), 5.38 (s, 1H), 5.33 (s, 2H), 3.7 (s, 3H), 2.80 (q, 2H), 2.62 (s, 3H), 2.57 (s, 3H), 2.38 (dd, 2H), 2.3–2.25 (m, 2H), 1.55–1.47 (m, 2H), 1.46–1.37 (m, 2H), 1.36 (t, 3H), 0.86 (t, 3H), 0.72 (t, 3H), FAB-MS: m/e 514 (M+1).

Step I: Preparation of 3-[4-(1-carboxy-1-phenylmethoxy)-3,5-dipropylphenylmethyl]-5,7-dimethyl-2-ethyl-3H-imidazo-[4,5-b]pyridine Using the general procedure for ester hydrolysis described in Step D of Example 2, the product of Step H was converted to the title compound in 80% yield.

$^1$H NMR (400 MHz, CDCl$_3$, ppm): δ7.47–7.34 (m, 2H), 7.33–7.22 (m, 3H), 6.92 (s, 1H), 6.69 (s, 2H), 5.35 (br s, 3H), 2.78 (q, 2H), 2.58 (s, 3H) 2.55 (s, 3H), 2.62–2.25 (m, 4H), 1.45–1.28 (m, 4H), 1.2 (t, 3H), 0.7 (t, 6H).

FAB-MS: m/e 500 (M+1).

EXAMPLE 14

3-[4-(1-Carboxy-1-(2-methylphenyl)methoxy)-3,5-dipropylphenylmethyl]-5,7-dimethyl-2-ethyl-3H-imidazo[4,5-b]pyridine The title compound was prepared according to the procedure described for the preparation of Example 13 (Step A-I) except for step H in which case the alkylating agent used was ethyl 2-bromo-(2-methyl)phenylacetate.

$^1$H NMR (400 MHz, CD$_3$OD/CDCl$_3$ ppm): δ7.47 (d, 1H), 7.14 (m, 2H), 7.07 (d, 1H), 6.95 (s, 1H), 6.7 (s, 2H), 5.39 (ABq, 2H), 5.15 (br s, 1H), 2.79 (q, 2H), 2.58 (s, 3H), 2.54 (s, 3H), 2.25 (t, H), 2.15 (s, 3H), 1.92–1.8 (m, 1H), 1.72 (m, 1H), 1.6 (m, 1H), 1.55–1.45 (m, 2H), 1.45–1.36 (m, 2H), 1.2 (t, 3H), 0.7 (t, 6H). 1.3–1.18 (m, 7H), 0.707 (t, 6H).

FAB-MS: m/e 514 (M+1).

EXAMPLE 15

3-[4-(1-Carboxy-1-(3-methylphenyl)methoxy)-3,5-dipropylphenylmethyl]-5,7-dimethyl-2-ethyl-3H-imidazo[4,5-b]pyridine The title compound was prepared according to the procedure described for the preparation of Example 13 (Step A-I) except for step H in which case the alkylating agent employed was ethyl 2-bromo-(3′-methylphenyl)acetate.

$^1$H NMR (400 MHz, CD$_3$OD/CDCl$_3$, ppm): δ7.22 (d, 1H), 7.154 (d, 2H), 7.09 (d, 1H), 6.94 (s, 1H), 6.69 (s, 2H), 5.36 (br s, 2H), 5.35 (s, 1H), 2.78 (q, 2H), 2.58 (s, 3H), 2.56 (s, 3H), 2.28 (s, 3H), 2.23 (m, 4H), 1.4 (m, 2H) 1.3–1.18 (m, 7H), 0.71 (t, 6H).

FAB-MS: m/e 514 (M+1).

EXAMPLE 16

3-[4-(1-Carboxy-1-(4-methylphenyl)methoxy)-3,5-dipropylphenylmethyl]-5,7-dimethyl-2-ethyl-3H-imidazo[4,5-b]pyridine The title compound was prepared according to the procedure described for the preparation of Example 13 (Step A-I) except for step H. The alkylating agent used in the step H was ethyl 2-bromo-(4′-methyl)phenylacetate.

¹H NMR (400 MHz, CD₃OD, ppm): δ7.28 (d, 2H, J=8.0 Hz); 7.15 (d, 2H, J=7.9 Hz); 6.99 (s, 1H); 6.73 (s, 1H); 4.97 (s, 1H); 2.82 (q, 2H. J=7.6 Hz); 2.60 (s, 3H); 2.57 (s, 3H); 2.33 (s, 3H); 2.27 (t, 4H, J=7.8 Hz); 1.43–1.27 (m, 4H); 1.20 (t, 23H, J=7.5 Hz); 0.72 (t, 6H, J=7.3 Hz).

FAB-MS: m/e 514 (M+1).

EXAMPLE 17

3-[4-(1-Carboxy-1-(2-chlorophenyl)methoxy)-3,5-dipropylphenylmethyl]-5,7-dimethyl-2-ethyl-3H-imidazo[4,5-b]pyridine The title compound was prepared according to the synthetic route described for Example 13 with appropriate modification in step H in which ethyl 2-bromo-(2'-chloro)phenylacetate was utilized as the alkylating agent.

¹H NMR (400 MHz, CD₃OD, ppm): δ7.68 (m, 1H); 7.39–7.33 (m, 3H); 7.02 (s, 1H); 6.76 (s, 2H); 5.50 (s, 1H); 5.45 (s, 2H); 2.83 (q, 2H, J=7.6 Hz); 2,60 (s, 3H); 2.57 (s, 3H); 2,32–2.27 (m, 4H); 1.43–1.28 (m, 4H); 1.19 (t, 3H, J=7.5 Hz); 0.73 (t, 6H, J=7.4 Hz).

FAB-MS: m/e 534 (M+1).

EXAMPLE 18

3-[4-(1-Carboxy-1-(3-chlorophenyl)methoxy)-3,5-dipropylphenylmethyl]-5,7-dimethyl-2-ethyl-3H-imidazo[4,5-b]pyridine The title compound was prepared according to the synthetic route described for Example 13 with appropriate modification in Step H where methyl 2-bromo-(3'-chlorophenyl)acetate was used as the alkylating agent.

¹H NMR (400 MHz, CD₃OD, ppm): δ7.48 (s, 1H); 7.35–7.31 (m, 3H); 6.99 (s, 1H); 6.75 (s, 1H); 5.41 (s, 2H); 4.99 (s, 1H); 2.82 (q, 2H, J=7.6 Hz); 2.60 (s, 3H); 2.57 (s, 3H); 2.29 (t, 4H, J=7.7 Hz); 1.45–1.27 (m, 4) 1.21 (t, 3H, J=7.6 Hz); 0.74 (t, 6H, J=7.4 Hz).

FAB-MS: m/e 534 (M+1).

EXAMPLE 19

3-[4-(1-Carboxy-1-(4-chlorophenyl)methoxy)-3,5-dipropylphenylmethyl]-5,7-dimethyl-2-ethyl-3H-imidazo[4,5-b]pyridine The title compound was prepared according to the synthetic route described for Example 13 with appropriate modification in step H where methyl 2-bromo-(4'-chloro)phenylacetate was used as the alkylating agent.

¹H NMR (400 MHz, CD₃OD, ppm): δ7.40 (d, 2H, 8.3 Hz); 7.229 (d, 2H, J=8.3 Hz); 6.97 (s, 1H); 6.72 (s, 2H); 5.39 (s, 2H); 4.91 (s, 1H); 2.80 (q, 2H, J=7.6 Hz); 2.59 (s, 3H); 2.57 (s, 3H); 2.28 (t, 4H, J=7.9 Hz); 1.44–1.28 (m, 4H); 1.21 (t, 3H, J=7.6 Hz); 0.73 (t, 6H, J=7.3 Hz).

FAB-MS: m/e 534 (M+1).

EXAMPLE 20

3-[4-(1-Carboxy-1-(3,4-dichlorophenyl)methoxy)-3,5-dipropylphenylmethyl]-5,7-dimethyl-2-ethyl-3H-imidazo[4,5-b]pyridine The title compound was prepared according to the synthetic route described for Example 13 except for an appropriate modification in Step H where methyl 2-bromo-(3',4'-dichlorophenyl)acetate was used as the alkylating agent.

¹H NMR (400 MHz, CD₃OD, ppm): δ7.64 (d, 1H, J=1.9 Hz); 7.50 (d, 1H, J=8.3 Hz); 7.37 (dd, 1H, J=2.0, 8.3 Hz); 7.00 (s, 1H); 6.77 (s, 2H); 5.43 (s, 2H); 5.02 (s, 1H); 2.84 (q, 2H, J=7.6 Hz); 2.62 (s, 3H); 2.60 (s, 3H); 2.33 (m, 4H); 1.40 (m, 4H); 1.24 (t, 3H, J=7.5 Hz); 0.77 (t, 6H, J=7.3 Hz).

FAB-MS: m/e 568 (M+1).

EXAMPLE 21

3-[4-(1-Carboxy-1-(3-bromophenyl)methoxy)-3,5-dipropylphenylmethyl]-5,7-dimethyl-2-ethyl-3H-imidazo[4,5-b]pyridine The title compound was prepared according to the synthetic route described for Example 13 except for an appropriate modification in Step H where methyl 2-bromo-(3'-bromo)phenylacetate was used as the alkylating agent.

¹H NMR (200 MHz, CD₃OD, ppm): δ7.65 (d, 1H, J=1.8 Hz); 7.53 (dd, 1H, J=1.2, 7.8 Hz); 7.41 (d, 1H, J=7.9 Hz); 7.28 (t, 1H, J=7.8 Hz); 7.03 (s, 1H); 6.78 (s, 2H); 5.45 (s, 2H); 5.03 (s, 1H); 2.85 (q, 2H, J=7.6 Hz); 2.60 (s, 3H); 2.58 (s, 3H); 2.31 (t, 4H, J=7.8 Hz); 1.46–1.28 (m, 4H); 1.22 (t, 2H, J=7.6 Hz); 0.75 (t, 6H, J=7.3 Hz).

FAB-MS: m/e 579 (M+1).

EXAMPLE 22

3-[4-(1-Carboxy-1-(2,5-difluorophenyl)methoxy)-3,5-dipropylphenylmethyl]-5,7-dimethyl-2-ethyl-3H-imidazo[4,5-b]pyridine The title compound was prepared according to the synthetic route described for Example 13 except for a modification in Step H where ethyl 2-bromo-(2',5'-difluorophenyl)acetate was used as the alkylating agent.

¹H NMR (400 MHz, CD₃OD, ppm): δ7.38 (m, 1H); 7.01 (m, 3H); 6.73 (s, 2H); 5.43 (s, 2H); 5.17 (s, 1H); 2.81 (q, 2H, J=7.6 Hz); 2.60 (s, 3h); 2.57 (s, 3H); 2.31 (t, 4H, J=8.0 Hz); 1.49–1.40 (m, 2H); 1.34–1.24 (m, 2H); 1.18 (t, 3H, J=7.6 Hz); 0.75 (t, 6H, J=7.3 Hz).

FAB-MS: m/e 564 (M+1).

EXAMPLE 23

3-[4-(1-Carboxy-1-(3,5-bis(trifluoromethylphenyl)methoxy)-3,5dipropylphenylmethyl]-5,7-dimethyl-2-ethyl-3H-imidazo[4,5-b]pyridine The title compound was prepared according to the synthetic route described for Example 13 except for Step H where methyl 2-bromo -(3',5'-bis-trifluoromethylphenyl)acetate was used as the alkylating agent.

¹H NMR (400 MHz, CD₃OD, ppm): δ8.07 (s, 2H); 7.93 (s, 1H); 7.01 (s, 1H); 6,79 (s, 2H); 5.43 (s, 2H); 5.24 (s, 1H); 2.84 (q, 2H, J=7.6 Hz); 2.60 (s, 3H); 5.7 (s, 3H); 2.32–2.23 (m, 4H); 1.46–1.31 (m, 4H); 1.23 (t, 3H, J=7.6 Hz); 0.72 (t, 6H, J=7.4 Hz).

FAB-MS: m/e 636 (M+1).

EXAMPLE 24

3-[4-(1-Carboxy-1-(3-N,N-dimethylaminophenyl)methoxy)-3,5dipropylphenylmethyl]-5,7-dimethyl-2-ethyl-3H-imidazo[4,5-b]pyridine The title compound was prepared according to the synthetic route described for Example 13 except for Step H where ethyl 2-bromo -(3'-nitro)-phenylacetate was used as the alkylating agent. The alkylated product was reduced by treatment with stannous chloride in concentrated hydrochloric acid and ethanol to the corresponding amino compound which was further converted to its dimethylamino derivative by alkylation with methyl iodide using potassium carbonate in DMF.

$^1$H NMR (200 MHz, CD$_3$OD, ppm): δ7.17 (t, 1H, J=7.9 Hz); 7.02 (s, 1H); 6.83–6.70 (m, 5H); 5.44 (s, 2H); 4.94 (s, 1H); 2.89 (s, 6H); 2.84 (q, 2H, J=7.6 Hz); 2.60 (s, 3H); 2.57 (s, 3H); 2.30 (t, 4H, J=7.9 Hz); 1.45–1.29 (m, 4H); 1.21 (t, 3H, J=7.6 Hz); 0.73 (t, 6H, J=7.3 Hz).

FAB-MS: m/e 531 (M+1).

EXAMPLE 25

3-[4-(N-(1-Carboxy-1-phenylmethyl)-N-methylamino)-phenylmethyl]-5,7-dimethyl-2-ethyl-3H-imidazo[4,5-b]pyridine Step A: Preparation of 5,7-dimethyl-2-ethyl-3-(4-nitrophenylmethyl) -3H-imidazo[4,5-b]pyridine To a solution of 5.0 g (1.0 eq, 28.6 mmol) 5,7-dimethyl-2ethylimidazo[4,5-b]pyridine in 30 mL DMF under N$_2$ at rt was added 1.37 g (1.2 eq, 34.3 mmol) of a 60% oil dispersion of NaH. After stirring for 5 minutes, 8.64 g (1.4 eq, 40.0 mmol) of p-nitrobenzyl bromide was added. The dark brown mixture was stirred for 2 hours under a blanket of N$_2$ at rt. The mixture was diluted with 1 L CH$_2$Cl$_2$ and washed with 500 mL H$_2$O and 500 mL saturated aqueous NaCl. The organic phase was dried is over MgSO$_4$ and concentrated to a yellow oil. The oil was flash chromatographed with 50% ethyl acetate/hexane. The product-containing fractions were combined and concentrated to a yellow oil which crystallized on standing, yielding 6.81 g (76.8%) of the title compound.

$^1$H NMR (300 MHz, CDCl$_3$, ppm): δ8.15 (d, 2H), 7.27 (d, 2H), 6.92 (s, 1H), 5.55 (s, 2H), 2.77 (q, 2H), 2.64 (s, 3H), 2.57 (s, 3H), 1.32 (H=3H).

FAB-MS: m/e 325 (M+1).

Step B: Preparation of 3-(4-aminophenylmethyl)-5,7-dimethyl-2-ethyl-3H-imidazo [4,5-b]pyridine To a solution of 6.81 g (21.0 mmol) of the product of Step A dissolved in 75 mL methanol in a high pressure reaction vessel was added 0.3 g 5% palladium on carbon. The resulting suspension was pressurized to 40 psi with H$_2$ and shaken for 2 hours. The solution was filtered through a pad of celite and the filtrate concentrated to a gray-green oil which crystallized on standing. The crude material was flash chromatographed with 50% ethyl acetate/hexane and 3% methanol/ethyl acetate to yield 5.0 g (85%) of the title compound.

$^1$H NMR (300MHz, CD$_3$OD, ppm): δ6.85 (s, 1H), 6.80 (d, 2I-I), 6.52 (d, 2H), 5.26 (s, 2H), 2.72 (q, 2H), 2.49 (s, 3H), 2.49 (s, 6H), 1.12 (t, 3H).

FAB-MS: m/e 281 (M+1).

Step C: Preparation of 3-(4-N-(tert-butyloxycarbonyl)aminophenylmethyl) -5,7-dimethyl-2-ethyl-3H-imidazo[4,5-b]pyridine To a solution of 1.0 g (3.57 mmol) of of the product of Step B dissolved in 20 mL CH$_2$Cl$_2$ was added 0.75 mL (5.36 mmol, 1.5 eq) of triethylamine and 1.23 mL (5.36 mmol, 1.5 eq) of di-tert-butyl dicarbonate. The resulting solution was stirred for 18 hours. The products had crystallized out of solution after that time period. The suspension was diluted with 500 mL of CH$_2$Cl$_2$ (which promoted dissolution of the products) and washed with 200 mL H$_2$O at pH 9 (NaOH). The organic phase was dried over Na$_2$SO$_4$, filtered and concentrated to a pale yellow oil. The oil was flash chromatographed with 50% ethyl acetate/hexane to yield 450 mg (33%) of the title compound as a white powder.

$^1$H NMR (300 MHz, CDCl$_3$, ppm): δ7.26 (d, 2H), 7.04 (d, 2H), 6.89 (s, 1H), 6.63 (br s, 1H), 5.39 (s, 2H), 2.77 (q, 2H), 2.62 (s, 3H), 2.59 (s, 3H), 1.49 (s, 9H), 1.29 (t, 3H).

FAB-MS: m/e 381 (M+1).

General procedure for alkylation of N-BOC protected amines:

Step D: Preparation of 3-[4-(N-tert-butyloxycarbonyl-N-methylamino)phenylmethyl]-5,7-dimethyl-2-ethyl-3H-imidazo[4,5-b]pyridine To a solution of 100 mg of the product of Step C dissolved in 4 mL of DMF was added 16 mg (0.39 mmol, 1.5 eq) of a 60% oil dispersion of NaH. This mixture was stirred for 5 minutes until evolution of hydrogen ceased, and then 32.8 mL (73.8 mg, 0.52 mmol, 2.0 eq) of methyl iodide was added. The solution was then stirred for 18 hours. The excess NaH was quenched with methanol and then all volatiles were removed in vacuo. The resultant brown oil was purified on a silica gel flash chromatography column eluted with 50% ethyl acetate/hexane. The product fractions were combined and concentrated to give a pale yellow oil which was used directly in the next step.

$^1$H NMR (400 MHz, CDCl$_3$, ppm): δ7,12 (d, 2H), 7.04 (d, 2H), 6.87 (s. 1H), 5.40 (s, 2H), 3.18 (s, 3H), 2.77 (q, 2H), 2.60 (s, 3H), 2.56 (s, 3H) 1.49 (s, 9H),1.27 (t, 3H).

FAB-MS: m/e 395 (M+1).

General procedure for deprotection of N-BOC amines:

Step E: Preparation of 5,7-dimethyl-2-ethyl-3-[4-(N-methylaminophenyl)methyl]-3H-imidazo[4,5-b]pyridine Dissolved the product of Step D in 2.0 mL CH$_2$Cl$_2$ and added 2.0 mL TFA. Solution was stirred for 3 hours. Volatiles were removed in vacuo and the compound was dissolved in methanol. 2.0 mL saturated aqueous NaHCO$_3$ was added to neutralize the excess TFA. The methanol was then concentrated and the H$_2$O azeotroped with toluene. The compound was taken up in CHCl$_3$ and the excess NaHCO$_3$ was filtered out through a celite pad. The solution was concentrated yield 9 mg (94%) of a pale yellow oil.

$^1$H NMR (400 MHz, CDCl$_3$, ppm): δ6.97 (d, 2H), 6.85 (s, 1H), 6.48 (d, 2H), 5.32 (s, 2H), 3.73 (br s, 3H), 2.79 (q, 2H), 2.76 (s, 3H), 2.61 (s, 3H), 2.59 (s, 3H), 1.28 (t, 3H).

FAB-MS: m/e 295 (M+1).

General procedure for phenylaminophenylacetic acid synthesis:

Step F: Preparation of 3-[4-(N-(1-carbomethoxy-1-phenylmethyl)-N-methyl)aminophenylmethyl]-5,7-dimethyl-2-ethyl-3H-imidazo[4,5-b]-pyridine To a solution of 72.3 mg (0.25 mmol) of the product of Step E dissolved in 2.0 mL DMF was added 15 mg (0.37 mmol, 1.5 eq) of a 60% oil dispersion of NaH, and the reaction mixture was stirred at room temperature. After evolution of hydrogen had ceased, 95.5 mL (0.49 mmol, 2.0 eq) of methyl-2-bromophenylacetate was added. The resulting solution was stirred for 80 hours under N$_2$ at rt. The excess NaH was quenched with methanol and the volatiles were removed in vacuo. The resultant oil was purified on a silica gel flash chromatography column eluted with 50% ethyl acetate/hexane to yield 80.7 mg (73%) of the title compound as a pale yellow oil.

$^1$H NMR (400 MHz, CDCl$_3$, ppm): δ7.29–7.38 (m, 3H), 7.22 (d, 2H), 7.05 (d, 2H), 6.87 (s, 1H), 6.74 (d, 2H), 5.69 (s, 1H), 5.36 (s, 2H), 3.74 (s, 3H), 2.82 (q, 2H), 2.73 (s, 3H), 2.61 (s, 3H), 2.59 (s, 3H), 1.51 (t, 3H).

FAB-MS: m/e 443 (M+1).

Step G: Preparation of 3-[4-(N-(1-carboxy-1-phenylmethyl)-N-methylamino)phenylmethyl]-5,7-dimethyl-2-ethyl-. 3H-imidazo[4,5-b]pyridine To a solution of the product of Step F dissolved in 3.0 mL methanol, was added 3.0 mL of 3N NaOH, and the solution was stirred for 7 days. The methanol was removed in vacuo and the H₂O was removed by azeotropic distillation with toluene. The product was taken up in CHCl₃ and the excess NaOH filtered through a celite pad. The CHCl₃ was concentrated and the resultant oil was purified on a 20 cm×20 cm×500 mm silica gel preparatory TLC plate, developed with a solution of CHCl₃/MeOH/NH₄OH (80:20:2). The product was extracted from the silica gel with 100 mL of 10% methanol/CHCl₃. The solution was concentrated and the resultant oil triturated with ether to yield 61 mg (78.2%) of the title compound as a white powder.

¹H NMR (400 MHz, CDCl₃, ppm): δ7.00 (s, 5H), 6.77 (s, 1H), 6.70 (d, 2H), 6.43 (d, 2H), 5.15 (s, 1H), 5.12 (s, 2H), 2.68 (q, 2H), 2.57 (s, 3H), 2.40 (s, 6H), 1.20 (t, 3H).

FAB-MS: m/e 429 (M+1).

EXAMPLE 26

3-[4-(N-(1-Carboxy-1-phenylmethyl)-N-ethylamino)phenylmethyl]-5,7-dimethyl-2-ethyl-3H-imidazo[4,5-b]pyridine Step A: Preparation of 5,7-dimethyl-2-ethyl-3-[4-(N-tertbutyloxycarbonyl -N-ethylamino)phenylmethyl]-3H-imidazo[4,5-b]pyridine Using the general procedure for the alkylation of N-BOC protected amines described in Step D of Example 25, 5.7-dimethyl-2-ethyl-3-[4-(N-tert-butyloxycarbonylamino)phenylmethyl]-3H-imidazo[4,5b]pyridine (Step C, Example 26) was alkylated with ethyl iodide. Standard workup and purification by flash chromatography afforded the title compound.

¹H NMR (300 MHz, CDCl₃, ppm): δ7.09 (s, 4H), 6.90 (s, 1H), 5.44 (s, 2H), 3.62 (q, 2H), 2.80 (q, 2H), 2.64 (s, 3H), 2.59 (s, 3H), 1.40 (s, 9H), 1.28 (t, 3H), 1.09 (t, 3H).

FAB-MS: m/e 409 (M+1).

Step B: Preparation of 5,7-dimethyl-2-ethyl-3-[4-N-ethylaminophenylmethyl]-3H-imidazo[4,5-b]pyridine Using the general procedure for deprotection of N-BOC amines described in Step E of Example 25, the product of Step A was converted to the title compound.

¹H NMR (300 MHz, CDCl₃, ppm): δ6.97 (d, 2H), 6.87 (s, 1H), 6.49 (d, 2H), 3.10 (q, 2H), 2.80 (q, 2H), 2.62 (s, 3H), 2.60 (s, 3H), 1.29 (t, 3H), 1.21 (t, 3H).

FAB-MS: m/e 308 (M+1).

Step C: Preparation of 3-[4-(N-(1-carbomethoxy-1-phenylmethyl)-N-ethylamino)phenylmethyl]-5,7-dimethyl-2-ethyl-3H-imidazo [4,5-b]pyridine Using the general procedure for the phenylaminophenyl-acetic acid synthesis described in Step F of Example 25, the product of Step B was alkylated with methyl 2-bromophenylacetate. Standard workup and purification by flash chromatography afforded the title compound.

¹H NMR (200 MHz, CDCl₃, ppm): δ7.24–7.40 (m 5H), 7.05 (d, 2H), 6.88 (s, 1H), 6.72 (d, 2H), 5.49 (s, 1H), 5.37 (s, 2H), 4.73 (s, 3H), 3.28 (q, 2H), 2.83 (q, 2H), 2.62 (s, 3H), 2.60 (s, 3H), 1.31 (t, 3H), 0.86 (t, 3H).

FAB-MS: m/e 457 (M+1).

Step D: Preparation of 3-[4-(N-(1-carboxy-1-phenylmethyl)-N-ethylamino)phenylmethyl]-5,7-dimethyl-2-ethyl-3H-imidazo[4,5-b]pyridine Using the general procedure for ester hydrolysis described in Step D of Example 2, the product of Step C was converted to the title compound.

¹H NMR (400 MHz, CDCl₃, ppm): δ7.05 (m, 5H), 6.75 (s, 1H), 5.72 (d, 2H), 6.42 (d, 2H), 5.21 (s, 1H), 5.14 (s, 2H), 3.12 (q, 2H), 2.73 (q, 2H), 2.58 (s, 3H), 2.37 (s, 3H), 1.24 (t, 3H).

FAB-MS: m/c 443 (M+1).

EXAMPLE 27

3-[4-(N-(1-Carboxy-1-phenylmethyl)-N-propylamino)phenylmethyl]-5,7-dimethyl -2-ethyl-3H-imidazo[4,5-b]pyridine Step A: Preparation of 3-[4-(N-(tert-butyloxycarbonyl)-N.

propylamino)phenylmethyl]-5,7-dimethyl-2-ethyl-3H imidazo[4,5-b]pyridine

Using the general procedure for the alkylation of N-BOC protected amines described in Step D of Example 25, 3-[4-N-(tert-butyloxy-carbonyl)aminophenylmethyl]-5,7-dimethyl-2-ethyl-3H-imidazo[4,5-b]pyridine (Step C, Example 25) was alkylated with propyl bromide. Standard workup and purification by flash chromatography afforded the title compound.

¹H NMR (300 MHz, CDCl₃, ppm): δ7.09 (s,4H), 6.89 (s, 1H), 5.44 (s, 2H), 3.52 (t, 2H), 2.79 (q, 2H), 2.63 (s, 3H), 2.59 (s, 3H), 1.50 (m, 2H), 1.40 (s, 9H), 1.28 (t, 3H), 0.84 (t, 3H).

FAB-MS: m/e 423 (M+1).

Step B: Preparation of 5,7-dimethyl-2-ethyl-3-[4-(N-propylamino)phenylmethyl]-3H-imidazo[4,5-b]pyridine Using the general procedure for deprotection of N-BOC amines described in Step E of Example 25, the product of Step A was converted to the title compound.

¹H NMR (300 MHz, CDCl₃, ppm): δ6.97 (d, 2H), 6.88 (s, 1H), 6.49 (d, 2H), 5.33 (s, 2H), 3.02 (t, 2H), 2.80 (q, 2H), 2.62 (s, 3H),2.60 (s, 3H), 1.60 (m, 2H), 1.30 (t, 3H), 0.98 (t, 3H).

FAB-MS: m/e 323 (M+1).

Step C: Preparation of 3-[4-(N-(1-carbomethoxy-1-phenyl)methyl)-N-propylamino)phenylmethyl]-5,7-dimethyl-2-ethyl-3H-imidazo[4,5-b]pyridine Using the general procedure for the phenylaminophenylacetic, acid synthesis described in Step F of Example 25, the product of Step B was alkylated with methyl 2-bromophenylacetate. Standard workup and purification by flash chromatography afforded the title compound.

¹H NMR (400 MHz, CDCl₃, ppm): δ7.22–7.38 (m, 5H), 7.04 (d, 2H), 6.88 (s, 1H), 6.70 (d, 2H), 5.49 (s, 1H), 5.37 (s, 2H), 3.72 (t, 2H), 2.83% (q, 2H), 2.62 (s, 3H), 2.60 (s, 3H), 1.44 (m, 2H), 1.33 (t, 3H), 0.89 (t, 3H).

FAB-MS: m/e 471 (M+1).

Step D: Preparation of 3-[4-(N-(1-carboxy-1-phenylmethyl)-N-propylamino)phenylmethyl]-5,7-dimethyl-2-ethyl-3H-imidazo[4,5-b]pyridine Using the general procedure for ester hydrolysis described in Step D of Example 2, the product of Step C was converted to the title compound.

¹H NMR (400 MHz, CDCl₃, ppm): δ7.20 (br s, 2H), 7.06 (br s, 3H), 6.78 (s, 1H), 6.73 (d, 2H), 6.52 (d, 2H), 5.11 (br s, 3H), 2.97 (m, 2H), 2.71 (q, 2H), 2.57 (s, 3H), 2.42 (s, 3H), 1.23 (t, 3H), 0.87 (m, 2H), 0.46 (t, 3H).

FAB-MS: m/e 457 (M+1).

EXAMPLE 28

3-[4-N-(1-Carboxy-1-phenylmethyl)aminophenylmethyl]-5,7-dimethyl-2-ethyl -3H-imidazo[4,5-b]pyridine Step A: Preparation of 3-[4-(N-(1-carbomethoxy-1-phenylmethyl)amino)phenylmethyl]-5,7-dimethyl-2-ethyl-3H-imidazo-[4,5-b]pyridine To a solution of 0.50 g (1.79 mmol) of 3-(4-aminophenylmethyl) -5,7-dimethyl-2-ethyl-3H-imidazo[4,5-b]pyridine (Step B, Example 25) in 4.0 mL DMF, was added 143 mg (3.57 mmol, 2.0 eq) of a 60% oil dispersion of NaH. When evolution of hydrogen ceased (approximately 5 min.), 1.04 mL (5.36 mmol, 3.0 eq) of methyl 2-bromophenylacetate was added, and the mixture was stirred for 18 hours. The DMF was removed in vacuo and the resultant brown oil was flash chromatographed with 2:1 ethyl acetate/hexane to yield 0.690 g (90%) of a yellow-green powder.

$^1$H NMR (400 MHz, CDCl$_3$, ppm): $\delta$7.42 (d, 2H), 7.23–7.35 (m, 3H), 6.89 (d, 2H), 6.85 (s, 1H), 6.43 (d, 2H), 5.28 (s, 2H), 4.97–5.01 (m, 1H), 3.69 (s, 3H), 2.77 (q, 2H), 2.60 (s, 3H), 2.56 (s, 3H), 1.25 (t, 3H).

FAB-MS: m/e 429 (M+1).

Step B: Preparation of 3-[4-(N-(1-carboxy-1-phenylmethyl)amino)phenylmethyl]-5,7-dimethyl-2-ethyl-3H-imidazo-[4,5-b]pyridine To a solution of 0.45 g of the product of Step A dissolved in 5.0 mL methanol, was added 3.0 mL of 3N NaOH solution, and the mixture was stirred for 30 minutes. The methanol was removed in vacuo and the water was removed by azeotropic distillation with toluene. The o toluene was removed in vacuo, then the product was redissolved in CHCl$_3$ and excess NaOH was removed by filtration of the suspension through a celite pad. The filtrate was concentrated to a clear oil and purified on a silica gel flash chromatography column eluted with CHCl$_3$/MeOH/NH$_4$OH (80:15:1). The product fractions were combined and concentrated. The resultant oil was triturated with ether to yield 396 mg (91%) of the title compound as a white powder.

$^1$H NMR (300 MHz, CDCl$_3$, ppm): $\delta$7.48 (d, 2H), 7.40 (s, 1H), 7.20–7.34 (m, 4H), 6.91 (s, 1H), 6.87 (d, 2H), 5.31 (s, 2H), 4.89 (br s, 1H), 2.78 (q, 2H), 2.59 (s, 6H), 1.24 (t, 3H).

FAB-MS: m/e 415 (M+1).

EXAMPLE 29

3-[4-(N-(1-Carboxy-1-phenylmethyl)-N-allylamino)-phenylmethyl]-5,7-dimethyl -2-ethyl-3H-imidazo[4,5-b]pyridine General procedure for alkylation of secondary amines with LiN(TMS)$_2$:

Step A: Preparation of 3-[4-(N-(1-carbomethoxy-1-phenylmethyl)-N-allylamino)phenylmethyl]-5,7-dimethyl-2-ethyl-3-imidazo[4,5-b]pyridine To a solution of 0.30 g (0.70 mmol) of 3-[4-(N-(1-carbomethoxy -1-phenylmethyl)amino)phenylmethyl]-5,7-dimethyl-2-ethyl-3H-imidazo[4,5-b]pyridine in 1.5 mL THF, 0.84 mL (0.84 mmol. 1.2 eq) of 1M lithium bis(-trimethylsilyl)amide in THF was added producing a dark brown solution with evolution of hydrogen gas. After stirring the solution for 5 minutes, 96.1 µL (1.05 mmol, 1.5 eq) of allyl iodide was added. The resultant yellow solution was stirred for 18 hours. The solution was concentrated to a yellow oil which was flash chromatographed with 50% ethyl acetate/hexane. The product fractions were combined and concentrated to yield 173 mg (53%) of a pale yellow oil.

$^1$H NMR (400 MHz, CDCl$_3$, ppm): $\delta$7.52 (d, 2H), 7.22–7.33 (m, 3H). 6.98 (s, 1H), 6.78 (d, 2H), 6.23 (d, 2H), 5.52–5.65 (ddd, 1H), 5.26 (s, 1H), 5.23 (s, 2H), 5.03 (dd, 1H), 4.96 (dd, 1H), 3.62 (s, 3H), 3.18 (d, 2H), 2.71 (q, 2H), 2.57 (s, 3H), 2.54 (s, 3H), 1.21 (t, 3H).

FAB-MS: m/e 469 (M+1).

Step B: Preparation of 3-[4-(N-(1-carboxy-1-phenylmethyl)-N-allylamino)phenylmethyl]-5,7-dimethyl-2-ethyl-3H-imidazo[4,5-b]pyridine Using the general procedure for ester hydrolysis described in Step D of Example 2, the product of Step A was converted to the title compound.

$^1$H NMR (400 MHz, CD$_3$OD, ppm): $\delta$7.53 (d, 2H), 7.22 (t, 3H), 7.12 (t, 1H), 6.97 (s, 1H), 6.68 (d, 2H), 6.22 (d, 2H), 5.67–5.74 (m, 1H), 5.29 (s, 2H), 3.36 (dd, 1H), 3.07 (dd, 1H), 2.78 (q, 2H), 2.57 (s, 3H), 2.56 (s, 3H), 1.15 (t, 3H).

FAB-MS: m/e 455 (M+1).

EXAMPLE 30

3-[4-(N-(1-Carboxy-1-phenylmethyl)-N-iso-butylamino)phenylmethyl]-5,7-dimethyl-2-ethyl-3H-imidazo[4,5-b]pyridine Step A: Preparation of 3-[4-(N-(1-carbomethoxy-1-phenylmethyl)-N-iso-butylamino)phenylmethyl]-5,7-dimethyl-2-ethyl-3H-imidazo[4,5-b]-pyridine Using the general procedure for the alkylation of secondary amines described in Step A of Example 29, 3-[4-(N-(1-carbomethoxy-1-phenylmethylamino)-phenylmethyl]-5,7-dimethyl-2-ethyl-3H-imidazo[4,5-b]pyridine (Step A, Example 28) was alkylated with iso-butyl bromide. Standard workup and purification by flash chromatography afforded the title compound.

$^1$H NMR (400 MHz, CDCl$_3$, ppm): $\delta$7.49 (d, 2H), 7.18–7.30 (m, 3H), 6.83 (s, 1H), 6.77 (d, 2H), 6.20 (d, 2H), 5.49 (s, 1H), 5.22 (s, 21.t), 3.61 (s, 3H), 2.70 (q, 2H), 2.57 (s, 3H), 2.54 (s, 3H), 2.45 (d, 2H), 1.63 (m, 1H), 1.18 (t, 3H), 0.81 (d, 3H),0.75 (d, 3H).

FAB-MS: m/e 485 (M+1).

Step B: Preparation of 3-[4-(N-(1-carboxy-1-phenylmethyl)-N-isobutylamino)phenylmethyl]-5,7-dimethyl-2-ethyl-3H-imidazo[4,5-b]pyridine Using the general procedure for ester hydrolysis described in Step D of Example 2, the product of Step A was converted to the title compound.

$^1$H NMR (400 MHz, CD$_3$OD, ppm): $\delta$7.49 (d, 2H), 7.17 (t, 2H), 7.08 (t, 1H), 6.96 (s, 1H), 6.68 (d, 2H), 6.21 (d, 2H), 5.27 (s, 2H), 2.76 (q, 2H), 2.57–2.63 (m, 1H), 2.56 (s, 3H), 2.55 (s, 3H), 2.31 (dd, 1H), 1.65–1.71 (m, 1H), 1.12 (t, 3H), 0.93 (d, 3H), 0.76 (d, 3H).

FAB-MS: m/e 47 1 (M+1).

EXAMPLE 31

3-[4-(N-(1-Carboxy-1-phenylmethyl)-N-cyclopropylmethylamino)phenylmethyl]-5,7-dimethyl-2-ethyl-3H-imidazo[4,5-b]pyridine Step A: Preparation of 3-[4-(N-(1-carbomethoxy-1-phenylmethyl)-N-cyclopropylmethylamino)phenylmethyl]-5,7-dimethyl-2-ethyl-3H-imidazo[4,5-b]pyridine Using the general procedure for the alkylation of secondary amines with LiN(TMS)$_2$ described in Step A of Example 29, 3-[4-(N-(1-carbomethoxy -1-phenylmethyl)amino)phenylmethyl]-5,7-dimethyl-2-ethyl-3H-imidazo[4,5-b]-pyridine (Step A, Example 28) was alkylated with cyclopropylmethyl bromide. Standard workup and purification by flash chromatography afforded the title compound.

$^1$H NMR (400 MHz, CDCl$_3$, ppm): δ7.49 (d, 2H), 7.29 (t, 2H), 7.24 (d, 1H), 6.83 (s, 1H), 6.78 (d, 2H), 6.22 (d, 2H), 5.52 (s, 1H), 5.23 (s, 2H), 3.63 (s, 3H), 2.73 (q, 2H), 2.67 (dd, 1H), 2.57 (s, 3H), 2.55 (s, 3H), 2.09 (dd, 1H), 1.22 (t, 3H), 0.55–0.65 (m, 1H), 0.36 (dt, 2H), −0.06 (m, 2H).

FAB-MS: m/e 483 (M+1).

Step B: Preparation of 3-[4-(N-(1-carboxy-1-phenylmethyl)-N-cyclopropylmethylamino)phenylmethyl]-5,7-dimethyl-2-ethyl-3H-imidazo[4,5-b]pyridine Using the general procedure for ester hydrolysis described in Step D of Example 2, the product of Step A was converted to the title compound.

FAB-MS: m/e 485 (M+1).

EXAMPLE 32

3-[4-(N-(1-Carboxy-1-phenylmethyl)-N-sec-butylamino)phenylmethyl]-5,7-dimethyl-2-ethyl-3H-imidazo[4,5-b]pyridine Step A: Preparation of 3-[4-(N-(1-carbomethoxy-1-phenylmethyl)-N-sec-butylamino)phenylmethyl]-5,7-dimethyl-2-ethyl-3H-imidazo[4,5-b]-pyridine Using the general procedure for the alkylation of secondary amines with LiN(TMS)$_2$ described in Step A of Example 29, 3-[4-(N-(1-carbomethoxy -1-phenylmethyl)amino)phenylmethyl]-5,7-dimethyl-2-ethyl-3H-imidazo[4,5-b]-pyridine (Step A, Example 28) was alkylated with sec-butyl bromide. Standard workup and purification by flash chromatography afforded the title compound.

$^1$H NMR (400 MHz, CDCl$_3$, ppm): δ7.53–7.59 (m, 3H), 7.20–7.30 (m, 2H), 6.82 (s, 1H), 6.79 (d, 2H), 6.24 (d, 2H), 5.23 (s, 2H), 4.36 (s, 1H), 3.55 (s, 3H), 2.72 (q, 2H), 2.58 (s, 3H), 2.55 (s, 3H), 2.10 (m, 1H), 1.20 (t 3H), 0.82–0.90 (m, SH), 0.80 (d, 3H).

FAB-MS: m/e 485 (M+1).

Step B: Preparation of 3-[4-(N-(1-carboxy-1-phenylmethyl)-N-sec-butylamino)phenylmethyl]-5,7-dimethyl-2-ethyl-3H-imidazo[4,5-b]-pyridine Using the general procedure for ester hydrolysis described in Step D of Example 2, the product of Step A can be convened to the title compound.

EXAMPLE 33

3-[4-(N-(1-Carboxy-1-phenylmethyl)-N-iso-propylamino)phenylmethyl]-5,7-dimethyl-2-ethyl-3H-imidazo[4,5-b]pyridine Step A: Preparation of 3-[4-(N-(1-carbomethoxy-1-phenylmethyl)-N-iso-propylamino)phenylmethyl]-5,7-dimethyl-2-ethyl-3H-imidazo[4,5-b]-pyridine Using the general procedure for the alkylation of secondary amines with LiN(TMS)$_2$ described in Step A of Example 29, 3-[4-(N-(1-carbomethoxy -1-phenylmethyl)amino)phenylmethyl]-5,7-dimethyl-2-ethyl-3H-imidazo[4,5-b]pyridine (Step A, Example 28) was alkylated with isopropyl bromide. Standard workup and purification by flash chromatography afforded the title compound.

$^1$H NMR (400 MHz, CDCl$_3$, ppm): δ7.57 (d, 2H), 7.21–7.30 (m, 3H), 6.90 (br s, 1H), 6.81 (d, 2H) 6.25 (d, 2H), 5.27 (s, 2H), 4.42 (s, 1H), 3.56 (s, 3H), 2.73–2.82 (m, 2H), 2.64 (s, 3H), 2.57 (s, 3H), 2.49 (m, 1H), 1.24 (m, 3H), 0.88 (d, 3H), 0.80 (d, 3H).

FAB-MS: m/e 47 1 (M+1).

Step B: Preparation of 3-[4-(N-(1-carboxy-1-phenylmethyl)-N-isopropylamino)phenylmethyl]-5,7-dimethyl-2-ethyl-3H-imidazo[4,5-b]pyridine Using the general procedure for ester hydrolysis described in Step D of Example 2, the product of Step A can be convened to the title compound.

EXAMPLE 34

3-[4-(N-(1-(Tetrazol-5-yl)-1-phenylmethyl)-N-methylamino)phenylmethyl]-5,7-dimethyl-2-ethyl-3H-imidazo[4,5-b]pyridine Step A: Preparation of 3-[4-(N-(1-cyano-1-phenylmethyl)-N- methylamino)phenylmethyl]-5,7-dimethyl-2-ethyl-3H-imidazo[4,5-b]pyridine To a solution of 75 mg (0.26 mmol) of 5,7-dimethyl-2-ethyl-3-(4-N-methylaminophenylmethyl)-3H-imidazo[4,5-b]pyridine (Step E, Example 26) dissolved in 1.0 mL methanol and 1.0 mL acetic acid was added 51.9 uL (0.51 mmol) benzaldehyde and 25 mg (0.38 mmol) potassium cyanide. The mixture was stirred for 24 hours at room temperature, then evaporated in vacuo. The residual oil was purified on a silica gel flash chromatography column to afford 101 mg (97%) of the title compound.

$^1$H NMR (400 MHz, CDCl$_3$, ppm): 15 7.32–7.40 (m, 3H), 7.24 (d, 2H), 7.08 (d, 2H), 6.90 (s, 1H), 6.75 (d, 2H), 5.65 (s, 1H), 5.35 (s, 2H), 2.88 (q, 2H) 2.75 (s, 3H), 2.62 (s, 3H), 2.58 (s, 3H), 1.50 (t, 3H).

FAB-MS: m/e 410 (M+1).

Step B: Preparation of 3-[4-(N-(1-(tetrazol-5-yl)-1-phenylmethyl)-N-methylamino)phenylmethyl]-5,7-dimethyl-2-ethyl-3H-imidazo[4,5-b]-pyridine To a solution of 101 mg (0.25 mmol) of the product of Step A dissolved in 5.0 mL toluene was added 154 mg (0.75 mmol) of trimethylstannyl azide, and the mixture was stirred and heated at reflux for 24 hours. The reaction mixture was evaporated in vacuo, the residue was redissolved in 5.0 mL THF and then treated with 0.5 mL of a 1.0N HCl solution at 0° C. After stirring for 10 minutes, the reaction mixture was concentrated in vacuo, and the water was removed by azeotropic distillation with toluene. After evaporation, the residue was purified on a silica gel preparative layer chromatography plate eluted with CHCl$_3$/MeOH/NH$_4$OH (80:20:2). The product bands were collected and the product removed from the silica gel by elution with 10% methanol/chloroform. Evaporation of the filtrate and recrystallization of the residue from dichloromethane/hexanes afforded 90 mg (80%) of the title compound as a white powder.

$^1$H NMR (400 MHz, CD$_3$OD, ppm): 15 7.20–7.30 (m, 3H), 7. 10 (d, 2H), 6.97 (d, 2H), 6.82 (d, 2H), 6.52 (s, 1H), 5.40 (s, 2H), 2.83 (q, 2H), 2.80 (s, 3H), 2.58 (s, 3H), 2.57 (s, 3H), 1.22 (t, 3H).

FAB-MS: m/e 453 (M+1).

EXAMPLE 35

3-[4-(1-Carboxy-1-phenyl)methoxy-3-propylphenylmethyl]-5-carbomethoxy -2-ethyl-7-methyl-3H-imidazo[4,5-b]pyridine Step A: Preparation of 2-ethyl-7-methylimidazo[4,5-b]pyridine-4-oxide A solution of 28 g (174 mmol) of 2-ethyl-7-methylimidazo[4,5-b]-pyridine (described in European Patent Application 400,974, 12 May, 90) and m-chloroperbenzoic acid (80–90%, 44.6 g) in CHCl$_3$ (300 mL) was heated at reflux for 0.5 hours. The mixture was concentrated and purified (SiO$_2$, 100% CH$_2$Cl$_2$ gradient to 30% CH$_2$Cl$_2$/MeOH) to give 29.8 g of the title compound as a solid.

$^1$H NMR (300 MHz, CD$_3$OD, ppm): δ8.13 (d, 1H, J=6 Hz), 7.13 (d, 1H, J=6 Hz), 3.01 (q, 2H, J=7.5 Hz), 2.60 (s, 3H), 1.46 (t, 3H, J=7.5 Hz).

Step B: Preparation of 5-chloro-2-ethyl-7-methylimidazo-[4,5-b]pyridine

A mixture of 29.75 g (0.168 mol) of the product of Step A, CHCl$_3$ (25 mL) and POCl$_3$ (160 mL) was heated to 80° C. for 1 hour. After pouring over ice, the mixture was neutralized by careful addition of NH$_4$OH and extracted with EtOAc. Concentration gave 23.8 g of the title compound as a solid.

$^1$H NMR (250 MHz, CDCl$_3$, ppm): δ7.07 (s, 1H) 3.10 (q, 2H, J=7.5 Hz), 2.67 (s, 3H), 1.48 (t, 3H, J=7.5 Hz).

Step C: Preparation of 5-bromo-2-ethyl-7-methylimidazo-[4,5-b]pyridine

A mixture of 22.2 g (0.113 mol) of the product of Step B in 30% HBr-HOAc was heated to 100° C. for 19 hours. The mixture was poured onto ice, neutralized with NH$_4$OH, extracted (5×EtOAc), and the organic layers were concentrated to give 15 g (1$^{st}$ crop) of the title compound as a solid after crystallization from EtOAc.

$^1$H NMR (300 MHz, CDCl$_3$, ppm): δ7.22 (s, 1H) 3.13 (q, 2H, J=7.5Hz), 2.66 (s, 3H), 1.47 (t, 3H, J=7.5 Hz).

Step D: Preparation of 3-benzyl-5-bromo-2-ethyl-7-methyl-imidazo[4,5-b]-pyridine To a solution of 10 g (39 mmol) of the product of Step C in DMF (70 mL) at rt was added NaH (1.3 g of an 80% oil dispersion, 43 mmol). After 20 minutes benzyl bromide (5.15 mL, 43 mmol) was added and the reaction was stirred for 16 hours. The mixture was poured onto 500 g of ice and the solid residue was filtered, washed with water and air dried to give 13 g of the title compound.

$^1$H NMR (300 MHz, CDCl$_3$, ppm): δ7.33–7.22 (m, 3H), 7.19 (s, 1H), 7.11–7.07 (m, 2H), 5.42 (s, 2H), 2.76 (q, 2H, J=7.5 Hz), 2.63 (s, 3H), 1.29 (t, 3H, J=7.5 Hz).

Step E: Preparation of 3-benzyl-5-cyano-2-ethyl-7-methylimidazo-[4,5-b]pyridine.

A mixture of 620 mg(1.8 mmol) of the product of Step D and CuCN (806 mg, 9.0 mmol) was heated in pyridine (4 mL) at reflux for 10 hours under nitrogen. The reaction was cooled, then water (50 mL), KCN (1.17 g), and EtOAc (20 mL) were added and the mixture was heated to 50° C. for 5 min. Cooling and extraction with EtOAc (2×50 mL) gave 467 mg of the title compound as a tan solid.

$^1$H NMR (400 MHz, CDCl$_3$, ppm): δ7.40 (s, 1H), 7.35–7.20 (m, 3H), 7.18–7.07 (m, 2H), 5.44 (s, 2H), 2.83 (q, 2H, J=7.5 Hz), 2.67 (s, 3H), 1.32 (t, 3H, J=7.5 Hz).

Step F: Preparation of methyl 3-benzyl-2-ethyl-7-methylimidazo[4,5-b]pyridine-5-carboxylate A solution of 440 mg(1.59 mmol) of the product of Step E in H$_2$SO$_4$ (4 mL) and H$_2$O (4 mL) was heated to 80° C. for 8 hours. The reaction was cooled, MeOH (150 mL) was added, then conc NH$_4$OH was added until the mixture turned basic. The white solid (NH$_4$)$_2$SO$_4$ was filtered and washed with MeOH. The water and MeOH were removed in vacuo and and the residue was taken up in MeOH and then filtered to remove any remaining (NH$_4$)$_2$SO$_4$. After concentrating, and removal of water from the residue by evaporation from toluene, anhydrous 3% HCl-MeOH (50 mL) was added and the mixture was stirred overnight at rt. Filtration, concentration, and extraction from 5% aqueous Na$_2$CO$_3$ with CH$_2$Cl$_2$ gave 750 mg of the crude title compound as a solid.

$^1$H NMR (300 MHz, CDCl$_3$, ppm): δ7.93 (s, 1H) 7.38–7.29 (m, 3H), 7.12–7.03 (m, 2H), 5.53 (s, 2H), 3.96 (s, 3H), 2.78 (% 2H, J=7.5 Hz), 2.70 (s, 3H), 1.29 (t, 3H, J=7.5 Hz).

Step G: Preparation of methyl 2-ethyl-7-methylimidazo[4,5-b]pyridine-5-carboxylate A mixture of 750 mg of the crude product of Step F in MeOH (30 mL), concentrated aqueous HCl (1 mL), and 100 mg of moist Pearlman's catalyst were shaken under 1 atm. H$_2$ for 24 hours. The reaction was incomplete so 100 mg more of the catalyst was added and the reaction was shaken as described above for an additional 24 hours. Filtration, concentration, and extraction from dilute NH$_4$OH with EtOAc followed by drying (Na$_2$SO$_4$), concentration, and purification (SiO$_2$, 5% MeOH/EtOAc) gave 250 mg of the title compound as a solid.

$^1$H NMR (400 MHz, CDCl$_3$, ppm): δ7.90 (s, 1H), 4.00 (s, 3H), 3.10 (q, 2H, J=7.5 Hz), 2.71 (s, 3H), 1.38 (t, 3H, J=7.5 Hz).

Step H: Preparation of 4-hydroxy-3-(2-propen-1-yl)benzyl alcohol

To a solution of approximately 7.26 g (2.6 mmol) of crude 4-tert-butyldimethylsilyloxy -3-(2-propen-1-yl)benzyl alcohol (Step D of Example 7) dissolved in 50 mL of anhydrous THF was added 26 mL (2.6 mmol) of tetra-n-butylammonium fluoride and the reaction mixture was stirred at room temperature for 16 hours. The mixture was then evaporated in vacuo and the residual oil was purified on a silica gel flash chromatography column eluted with 5% methanol/chloroform to afford 3.386 g (79%) of the title compound as a colorless oil.

$^1$H NMR (300 MHz, CDCl$_3$, ppm): δ2.12 (br s, 1H), 3.35 (d, J=8 Hz, 2H), 4.54 (s, 3H), 5.05–5.15 (m, 2H), 5.90 (br s, 1H), 5.90–6.05 (m, 1H). 6.70 (d, J=10 Hz, 1H), 7.02–7.10 (m, 2H).

FAB-MS: m/e 165 (M+1).

Step I: Preparation of 4-hydroxy-3-propylbenzyl alcohol

To a solution of 0.370 g (2.25 mmol) of the product of Step H dissolved in 25 mL of absolute ethanol was added 53 mg of a 5% rhodium on carbon catalyst and the mixture was shaken under a 40 psig pressure of hydrogen on a Parr apparatus. After 30 minutes, the reaction mixture was removed, filtered and evaporated in vacuo. The residue was purified on a silica gel flash chromatography column eluted with 35% ethyl acetate/hexane to afford the title compound.

$^1$H NMR (300 MHz, CDCl$_3$, ppm): δ0.95 (t, J=8 Hz, 3H), 1.55–1.68 (m, 2H), 2.22 (br s, 1H), 2.57 (t, J=8 Hz, 2H), 4.56 (s, 2H), 5.93 (br s, 1), 6.66 (d, J=10 Hz, 1H), 7.00 (dd, J=2, 10 Hz, 1H), 7.08 (d, J=2 Hz, 1H).

FAB-MS: m/e 167 (M+1).

Step J: Preparation of methyl (4-hydroxymethyl-2-propylphenoxy)-2-phenylacetate

To a solution of 0.484 g (2.91 mmol) of the product of Step I dissolved in 12 mL of acetone were added 0.667 g (2.91 mmol) of methyl 2-bromophenylacetate, 0.804 g (5.82 mmol) of anhydrous K$_2$CO$_3$ and the mixture was stirred and heated at reflux for 5 hours. The mixture was then cooled, filtered and evaporated in vacuo. The residual oil was purified on a silica gel flash chromatography column eluted with 30% ethyl acetate/hexane to afford 0.756 g (83%) of the title compound.

$^1$H NMR (300 MHz, CDCl$_3$, ppm): δ0.95 (t, J=8 Hz, 3H), 1.58 (br s, 1H), 1.60–1.75 (m, 2H), 2.70 (t, J=8 Hz, 2H), 3.68 (s, 3H), 4.57 (m, 2H), 5.62 (s, 1H), 6.68 (d, J=10 Hz, 1H), 7.07 (dd, J=2, 10 Hz, 1H), 7.16 (d, J=2 Hz, 1H), 7.32–7.44 (m, 3H), 7.55–7.60 (m, 2H).

FAB-MS: m/e 315 (M+1).

Step K: Preparation of methyl 2-(4-tert-butyldimethyl-silyloxymethyl-2-propylphenoxy)-2-phenylacetate To a solution of 2.34 g (7.45 mmol) of the product of Step J in DMF (30 mL) were added imidazole (609 mg, 8.94 mmol) and tertbutyldimethyl-chlorosilane (1.35 g, 8.94 mmol) at 0° C. The solution was stirred at room temperature for 18 hours, and was then poured into 100 mL of ethyl acetate and washed with $H_2O$ (2×). The water layer was extracted with ethyl acetate (2×). The combined organic layer was washed with $H_2O$ (3×) and brine, and was dried over anhydrous $MgSO_4$. After concentration the mixture was purified by flash chromatography (hexane: EtOAc=10:1) to give 1.96 g of the title compound as a clear oil.

$^1$H NMR (400 MHz, $CDCl_3$, ppm): δ7.58 (dd, 2H, J=8.4, 1.8 Hz), 7.42–7.30 (m, 3H), 7.09 (d, 1H, J=1.8 Hz), 7.03 (dd, 1H, J=8.4, 1.8Hz), 6.67 (d, 1H, J=8.3 Hz), 5.61 (s, 1H), 4.63 (s, 2H), 3.68 (s, 3H), 2.69 (t, 2H, J=7.8 Hz), 1.72–1.60 (m, 2H), 0.94 (t, 2H, J=7.4 Hz), 0.90 (s, 9H), 0.06 (s, 6H).

Step L: Preparation of 2-(4-tert-butyldimethylsilyloxymethyl-2-propylphenoxy)-2-phenylacetic acid To a solution of 1.875 g (4.38 mmol) of the product of Step K in methanol (20 mL) was added 1N NaOH (4.82 mL, 4.82 mmol) at rt. The solution was stirred at rt for 3 hours. After the solvent was evaporated under reduced pressure, the residue was dissolved in $H_2O$ (30 mL) and washed with ethyl acetate (30 mL). The aqueous layer was acidified to pH=3 with 2N HCl. A milky emulsion was extracted with ethyl acetate (3×). The combined organic layer was washed with brine, and was dried over anhydrous $MgSO_4$. Concentration afforded 0.929 g of the title compound as a colorless glass.

$^1$H NMR (400 MHz, $CDCl_3$, ppm): d 7.56 (d, 2H, J=6.2Hz), 7.42–7.32 (m, 3H), 7.09 (s, 1H), 7.02 (d, 1H, J=8.3 Hz), 6.67 (d, 1H, J=8.2 Hz), 5.60 (s, 1H), 4.62 (s, 2H), 2.67 (t, 2H, J=7.4 Hz), 1.70–1.57 (m, 2H), 0.93 (t, 3H, J=7.2 Hz), 0.90 (s, 9H), 0.05 (s, 6H).

Step M: Preparation of tert-butyl 2-(4-tert-butyldimethylsilyloxymethyl -2-propylphenoxy)-2-phenylacetate To a solution of 929 mg (2.24 mmol) of the product of Step L in benzene were added oxalyl chloride (234 mL, 2.69 mmol) and one drop of DMF at 0° C. The solution was stirred at rt for 45 minutes. After concentration the residue was dissolved in $CH_2Cl_2$ (10 mL). The solution was added to a solution of tert-butyl alcohol (253 mL, 2.69 mmol) and $Et_3N$ in $CH_2Cl_2$ (10 mL) at 0° C. The solution was stirred at rt for 3 hours. The mixture was poured into EtOAc (50 mL) and washed with $H_2O$ (1×) and brine, and dried over anhydrous $MgSO_4$. Concentration gave 778 mg of the title compound as a slightly yellow glass.

$^1$H NMR (300 MHz, $CDCl_3$, ppm): δ7.60–7.30 (m, 5H), 7.09 (s, 1H), 7.03 (d, 1H, J=8.3 Hz), 6.68 (d, 1H, J=8.2 Hz), 5.49 (s, 1H), 4.62 (s, 2H), 2.80–2.60 (m, 2H), 1.80–1.55 (m, 2H), 1.33 (s, 9H), 0.93 (t, 3H), 0.90 (s, 9H). 0.05 (s, 6H).

Step N: Preparation of tert-butyl 2-(4-hydroxymethyl-2-propylphenoxy)-2-phenylacetate To a solution of 778 mg(1.59 mmol) of the product of Step J in THF (5 mL) was added 1N tetra-n-butylammonium fluoride solution in THF (2.69 mL, 2.69 mmol). After the solution was stirred at rt for 2 hours, it was poured into EtOAc (50 mL) and washed with $H_2O$ and brine, and dried over anhydrous $MgSO_4$. Concentration afforded 839 mg of the title compound as a yellow glass.

$^1$H NMR (400 MHz, $CDCl_3$, ppm): δ7.60–7.30 (m, 5H), 7.20–7.08 (m, 2H), 6.68 (d, 1H, J=8.2 Hz), 5.18 (s, 1H), 4.52 (s, 2H), 2.75–2.60 (m, 2H), 1.75–1.60 (m, 2H), 1.33 (s, 9H), 0.93 (t, 3H).

Step O: Preparation of tert-butyl 2-(4-bromomethyl-2-propylphenoxy)-2-phenylacetate To a solution of 839 mg of the crude product from Step N in $CH_2Cl_2$ (20 mL) were added triphenylphosphine (525 mg, 2 mmol) and carbon tetrabromide (663 mg, 2 mmol) at 0° C. The solution was stirred at 0° C. for 1 hour and at rt for 15 hours. The solution was poured into EtOAc (100 mL). After the precipitate was removed, the filtrate was washed with $H_2O$ and brine, and dried over anhydrous $MgSO_4$. Concentration afforded 302 mg of the title compound as a white solid.

$^1$H NMR (400 MHz, $CDCl_3$, ppm): δ7.57 (d, 2H, J=6.2 Hz), 7.41–7.33 (m, 3H), 7.17 (d, 1H, J=2.0 Hz), 7.10 (dd, 1H, J=8.3, 2.0 Hz), 6.67 (d, 1H, J=8.2 Hz), 5.49 (s, 1H), 4.52 (s, 2H), 2.75–2.65 (m, 2H), 1.76–1.62 (m, 2H), 1.34 (s, 9H), 0.96 (t, 3H, J=7.2 Hz).

Step P: Preparation of 3-[4-(1-carbo-tert-butoxy-1-phenylmethoxy)-3-propylphenylmethyl]-5-carbomethoxy-2-ethyl-7-methyl-3H-imidazo[4,5-b]pyridine To a 25 mL round bottom flask were placed 41.8 mg (0.19 mmol) of methyl 2-ethyl-7-methylimidazo[4,5-b]pyridine-5-carboxylate (the product of Step G of this Example) and a 60% oil dispersion of NaH (5 mg, 0.21 mmol). The flask was evacuated and filled with nitrogen. Dry DMF (2 mL) was added to the mixture dropwise at 0° C. The solution was stirred at rt for 5 minutes. To the solution was added 80 mg (0.19 mmol) of tert-butyl 2-(4-bromomethyl-2-propyl- phenoxy)-2-phenylacetate (Step O) in dry DMF (2 mL) at rt. After the solution was stirred at rt for 15 hours, it was poured into EtOAc (10 mL) and washed with $H_2O$ and brine, and dried over anhydrous $MgSO_4$. Concentration followed by purification by flash chromatography (hexane: EtOAc=2:1) afforded 63.6 mg of the title compound as a colorless glass.

$^1$H NMR (400 MHz, $CDCl_3$, ppm): δ7.92 (s, 1H), 7.52 (d, 2H, J=7.0 Hz), 7.40–7.30 (m, 3H), 6.99 (d, 1H, J=2.0 Hz), 6.83 (dd, 1H, J=8.3, 2.0 Hz), 6.61 (d, 1H, J=8.4 Hz), 5.44 (s, 2H), 5.43 (s, 1H), 3.97 (s, 3H), 2.79 (q, 2H, J=7.5 Hz), 2.70 (s, 3H), 2.65–2.55 (m, 2H), 1.70–1.55 (m, 2H), 1.3 (s, 9H), 1.25 (t, 3H, J=8.3 Hz), 0.89 (t, 3H. J=7.3 Hz).

Step Q: Preparation of 3-[4-(1-carboxy-1-phenylmethoxy)-3-propylphenylmethyl]-5-carbomethoxy-2-ethyl-7-methyl-3H-imidazo[4,5-b]-pyridine To a solution of 21.4 mg (0.038 mmol) of the product of Step P in $CH_2Cl_2$ (1 mL) was added TFA (0.4 mL, 5.19 mmol) at rt. The solution was stirred at rt for 2 hours. The crude mixture was directly purified by flash chromatography eluted with $CHCl_3$/MeOH/$NH_4OH$ (100:10:1) to give 11 mg of the title compound as a white solid.

$^1$H NMR (400 MHz, $CD_3OD$, ppm): δ7.84 (s, 1H), 7.55–7.42 (br m, 2H), 7.25–7.13 (m, 3H), 6.96 (s, 1H), 6.88–6.62 (br m, 2H), 5.43 (s, 3H), 3.87 (s, 3H), 2.81 (q, 2H, J=7.5 Hz), 2.58 (s, 3H), 2.50–2.40 (m, 2H), 1.53–1.37 (m, 2H), 1.16 (t, 3H, J=7.5 Hz), 0.74 (t, 3H, J=6.6 Hz).

FAB-MS: m/e 524 (M+Na), 540 (M+K).

EXAMPLE 36

3-[4-(1-Carboxy-1-phenylmethoxy)-3-propylphenylmethyl]-5-carboxy-2-ethyl-7-methyl-3H-imidazo[4,5-b]pyridine Step A: Preparation of 3-[4-(1-carbo-tert-butoxy-1-phenylmethoxy)-3-propylphenylmethyl]-5-carboxy-2-ethyl-7-methyl-3H-imidazo[4,5-b]-pyridine To a solution of 63 mg(0.113 mmol) of the product of Step M of Example 35 in MeOH (2 mL) was added 1N NaOH (136 mL, 0.136 mmol) at rt. The solution was refluxed for 3 hours. After the evaporation of the solvent the residue was taken up in H₂O and acidified to pH=3 with 2N hydrochloric acid. A white precipitate was collected and dried in a vacuum oven (60° C.) for 3 hours to afford 47 mg of the title compound as a white solid.

$^1$H NMR (400 MHz, CDCl₃, ppm): δ8.0 (s, 1H), 7.52 (d, 2H, J=6.9 Hz), 7.38–7.32 (m, 3H), 6.93 (s, 1H), 6.79 (dd, 1H, J=6.8, 1.1 Hz), 6.63 (d, 1H, J=8.4 Hz), 5.44 (s, 1H), 5.37 (s, 2H), 2.85 (q, 2H, J=6.7 Hz), 2.72 (s, 3H), 2.67–2.60 (m, 2H), 1.68–1.56 (m, 2H), 1.30 (s, 9H), 1.30 (t, 3H, J=8.3 Hz), 0.90 (t, 3H, J=6.5 Hz).

FAB-MS: m/e 544 (M+1).

Step B: Preparation of 3-[4-(1-carboxy-1-phenylmethoxy)-3-propyl-phenylmethyl]-5-carboxy-2-ethyl-7-methyl-3H-imidazo[4,5-b]pyridine To a solution of 3-[4-(1-carbo-t-butoxy-1-phenylmethoxy)-3propylphenylmethyl]-5-carboxy-2-ethyl-7-methyl-3H-imidazo[4,5-b]pyridine (47 mg, 0.087 mmol) in CHCl₃ (3 mL) was added TFA (0.5 mL) at −20° C. The solution was warmed to rt and was stirred at rt for 12 hours. After evaporation of the solvent the crude mixture was purified by flash chromatography eluted with CHCl₃/MeOH/AcOH (90:5:5) to give 31 mg of the title compound as a white solid.

$^1$H NMR (400 MHz, CD₃OD, ppm): δ7.90 (br s, 1H), 7.52 (d, 2H, J=7.1 Hz), 7.30–7.20 (m, 3H), 6.97 (s, 1H), 6.90–6.80 (m, 1H), 6.78–6.68 (m, 1H), 5.49 (br s, 2H), 5.47 (s, 1H), 2.90–2.75 (m, 2H), 2.61 (s, 3H), 2.54–2.45 (m, 2H), 1.55–1.45 (m, 2H), 1.17 (t, 3H, J=7.5 Hz), 0.;77 (t, 3H, J=7.3 Hz).

FAB-MS: m/e 510 (M+Na), 526 (M+K).

EXAMPLE 37

3-[4-(1-Carboxy-1-phenylmethoxy)-3-propylphenylmethyl]-5-carbobenzyloxy-2-ethyl-7-methyl-3H-imidazo[4,5-b]pyridine Step A: Preparation of 3-[4-(1-carbo-tert-butoxy-1-phenylmethoxy)-3-propylphenylmethyl]-5-carbobenzyloxy-2-ethyl-7-methyl-3H-imidazo [4,5-b]pyridine To a solution of 23.3 mg (0.043 mmol) of the product of Step A in Example 36 and bis(2-oxo-3-oxazolidinyl)-phosphinic chloride (13.1 mg, 0.052 mmol) in CH₂Cl₂ (2 mL) were added triethylamine (7.2 mL, 0.052 mmol) and benzyl alcohol (5.4 mL, 0.052 mmol) at rt. The solution was stirred at rt for 15 hours. The solution was poured into EtOAc (20 mL) and was washed with H₂O and brine, and dried over anhydrous MgSO₄. After evaporation of the solvent, the mixture was purified by mg, 0.052 mmol) in CH₂Cl₂ (2 mL) were added triethylamine (7.2 mL, compound as a colorless glass.

$^1$H NMR (400 MHz, CDCl₃): δ7.91 (s, 1H), 7.53–7.29 (m, 10H), 7.40–7.30 (m, 3H), 6.99 (s, 1H), 6.87 (d, 1H, J=8.4 Hz), 6.61 (d, 1H, J=8.4 Hz), 5.43 (s, 5H), 2.79 (q, 2H, J=7.5 Hz), 2.68 (s, 3H), 2.65–2.55 (m, 2H), 1.70–1.55 (m, 2H), 1.3 (s, 9H), 1.28 (t, 3H, J=8.3 Hz), 0.88 (t, 3H. J=7.3 Hz).

Step B: Preparation of 3-[4-(1-carboxy-1-phenylmethoxy)-3-propylphenylmethyl]-5-carbobenzyloxy-2-ethyl-7-methyl-3H-imidazo[4,5-b]-pyridine To a solution of the product of Step A (9 mg, 0.014 mmol) CH₂Cl₂ (1 mL) was added TFA (0.4 mL) at rt dropwise. The solution was stirred at rt for 2.5 hours. After evaporation of the solvent the crude mixture was purified by flash chromatography eluted with CHCl₃/MeOH/NH₄OH (80:15:1), to give 3.8 mg of the title compound as a white solid.

$^1$H NMR (400 MHz, CD₃OD, ppm): δ7.90 (s, 1H), 7.54 (d, 2H, J=7.0), 7.43 (d, 2H, J=7.1 Hz), 7.35–7.20 (m, 6H), 7.0 (s, 1H), 6.95–6.85 (m, 1H), 6.75–6.70 (m, 1H), 5.46 (s, 2H), 5.38 (s, 3H), 2.86 (q, 2H, J=7.6 Hz), 2.61 (s, 3H), 2.70–2.60 (m, 1H), 2.50–2.40 (m, 1H), 1.48–1.37 (m, 2H), 1.20 (t, 3H, J=8.3 Hz), 0.73 (t, 3H. J=7.3 Hz).

FAB-MS: m/e 600 (M+Na), 616 (M+K).

EXAMPLE 38

3-14-(1-Carboxy-1-(4-methyl-3-nitrophenyl)methoxy)-3,5-di-n-propylphenylmethyl]-5,7-dimethyl-2-ethyl-3H-imidazo[4,5-b]pyridine The title compound was prepared following the synthetic route described for the synthesis of Example 13 except for Step H where methyl 2-bromo-(4-methyl-3-nitro)phenylacetate was used as the alkylating agent.

$^1$H NMR (400 MHz, CD₃OD, ppm): d 8.06 (d, 1H, J=1.8 Hz); 7.68 (dd, 1H, J=1.7, 8.0 Hz); 7.47 (d, 1H, J=7.9 Hz); 7.15 (s, 1H); 6.88 (s, 2H); 5.51 (s, 2H); 5.20 (s, 1H); 2.96 (q, 2H, J=7.6 Hz); 2.62 (s, 3H); 2.56 (s, 3H); 2.36–2.32 (m, 4H); 1.45–1.28 (m, 4H); 1.25 (t, 3H, J=7.6 Hz); 0.75 (t, 6H, J=7.4 Hz).

EXAMPLE 39

3-[4-(1-Phenyl-1-phenylsulfonylaminocarbonylmethoxy)-3-propylphenylmethyl]-5,7-dimethyl-2-ethyl-3H-imidazo[4,5-b]pyridine Step A: Preparation of 3-[4-(1-phenyl-1-phenylsulfonylaminocarbonyl)methoxy)-3-propylphenylmethyl]-5,7-dimethyl-2-ethyl-3H-imidazo[4,5-b]pyridine A 15 mL capacity high pressure vessel equipped with a magnetic stir bar was charged with a solution of 0.118 g (0.26 mmol) of the product of Step C in Example 8 in 2.5 mL of anhydrous THF and 0.063 g (0.39 mmol) of 1,1′-carbonyldiimidazole was added. The vessel was sealed and the contents were stirred and heated at 80° C. for 1.5 hours. The reaction was then cooled to room temperature, opened and 0.061 g (0.39 mmol) of benzenesulfonamide and 77 μL (0.52 mmol) of 1,8-diazabicyclo [5.4.0]undec-7-ene were added. The reaction vessel was resealed and then stirred and heated at 80° C. for an additional 2 hours. The reaction vessel was then cooled, opened and the contents were partitioned between water and EtOAc. The organic layer was separated washed with 10% aqueous NaHSO₄, brine, dried (MgSO₄), filtered and evaporated. The residual oil was purified on a silica gel flash chromatography column eluted with 5% MeOH/CHCl₃ to 0.074 g (48%) of the title compound.

$^1$H NMR (400 MHz, CD₃OD, ppm): δ0.81 (t, J=7.60 Hz, 3H), 1.21 (t, J=7.60 Hz, 3H), 1.45–1.55 (m, 2H), 2.46–2.53 (m, 2H), 2.60 is, 3H), 2.61 (s, 3H), 2.83 (q, J=7.60 Hz, 2H), 5.41 (s, 1H), 5.42 (s, 2H), 6.46 (d, J=8.80 Hz, 1H), 6.64 (dd, J=2.40, 8.80 Hz, 1H), 6.98 (d, J=2.40 Hz, 1H), 7.05 (s, 1H), 7.26–7.60 (m, 6H), 7.76 (dd, J=1.60, 8.80 Hz, 2H), 7.89 (dd, J=1.60, 8.40 Hz, 2H).

FAB-MS: m/e 597 (M+1).

EXAMPLE 40

3-[4-(1-Carboxy-1-phenylmethoxy)-3-chloro-5-(prop-2-ene-1-yl)phenylmethyl]-5,7-dimethyl-2-ethyl-3H-imidazo [4,5-b]pyridine Step A: Preparation of methyl 3-chloro-4-hydroxy-5-(prop-2-ene-1-yl)benzoate To a 250 mL round-bottom flask equipped with a magnetic stir bar and a reflux condenser was added a solution of 10.33 g (55.4 mmol) of methyl 3-chloro-4-hydroxybenzoate dissolved in 110 mL of acetone and 5.27 mL (60.9 mmol) of allyl bromide and 15.30 g (111 mmol) of powdered potassium carbonate was added. The reaction was stirred and refluxed for 6 hours, then cooled and filtered. The filtrate was evaporated in vacuo and the residue was purified on a silica gel flash chromatography column eluted with 10% EtOAc-hexane to afford 10.462 g (84%) of the title compound.

$^1$H NMR (400 MHz, CDCl$_3$, ppm): δ3.43 (d, J=6.80 Hz, 2H), 3.87 (s, 3H), 5.07–5.11 (m, 2H), 5.92–6.03 (m, 2H), 7.74 (d, J=2.40 Hz, 1H), 7.91 (d, J=2.40 Hz, 1H).

Step B: Preparation of 3-chloro-4-hydroxy-5-(prop-2-en-1-yl)benzyl alcohol

To a stirred solution of 10.00 g (44.1 mmol) of the product of Step A in 100 mL methylene chloride was added 6.468 g (52,9 mmol) of 4-dimethyl-aminopyridine, 7.980 g (52.9 mmol) of tert-butyldimethylchlorosilane and the mixture was stirred at room temperature for 3 hours. The reaction mixture was partitioned between methylene chloride and water, the organic layer was separated washed with 1.0N HCl, 5% NaHCO$_3$, dried (MgSO$_4$), filtered and evaporated. The residue was dissolved in 35 mL of anhydous THF, magnetically stirred at 0° C., and then treated with 100 mL of a 1.0M solution of lithium triethylborohydride under a nitrogen atmosphere. The reaction was allowed to warm to room temperature, and treated with several mL water until hydrogen evolution ceased. The reaction mixture was evaporated in vacuo, redissolved in methylene chloride, dried (MgSO$_4$), filtered and reevaporated in vacuo. The residue was finally redissolved in 30 mL THF and treated with 45 mL of a 1.0M solution of tetrabutylammonium fluoride in THF while stirring for 12 hours at room temperature. The reaction mixture was then evaporated to an oil and purified on a silica gel flash chromatography column eluted with methylene chloride to afford 4.992 g (57%) of the title compound.

$^1$H NMR (400 MHz, CDCl$_3$, ppm): δ3.40 (d, J=6.80 Hz, 2H), 4.54 (s, 2H), 5.05–5.10 (m, 2H), 5.91–6.01 (m, 1H), 7.01 (d, J=1.60 Hz, 1H), 7.19 (d, J=1.60 Hz, 1H).

Step C: Preparation of methyl 2-(2-chloro-4-hydroxymethyl-6-(prop-2-en-1-yl)phenoxy)-2-phenylacetate To a magnetically stirred solution of 0.545 g (2.74 mmol) of the product of Step B in 10 mL acetone was added 0.628 g (2.74 mmol) of methyl α-bromophenylacetate, 0.757 g (5.48 mmol) of potassium carbonate and the reaction mixture was heated at reflux for 2.5 hours. The reaction mixture was cooled to room temperature, filtered and evaporated. The residue was purified on a silica gel flash chromatography column eluted with 15% EtOAc-hexane. Evaporation of the purified fractions and drying in vacuo afforded 0.789 g (83%) of the title compound.

$^1$H NMR (400 MHz, CDCl$_3$, ppm): δ1.97 (br s, 1H), 3.11 (dd, J=6.80, 15.60 Hz, 1H), 3.23 (dd, J=6.80, 15.60 Hz, 1H), 3.72 (s, 3H), 4.55 (s, 2H), 4.86–4.97 (m, 2H), 5.55–5.66 (m, 1H), 5.59 (s, 1H), 6.96 (d, J=2.00 Hz, 1H), 7.22 (d, J=2.00 Hz, 1H), 7.34–7.37 (m, 3H), 7.44–7.47 (m, 2H).

Step D: Preparation of 3-[4-(1-carbomethoxy-1-phenylmethoxy)-3-chloro -5-(prop-2-ene-1-yl)phenylmethyl]-5,7-dimethyl-2-ethyl -3H-imidazo-[4,5-b]pyridine To a magnetically stirred solution of 0.541 g (2.06 mmol) of triphenylphosphine in 4 mL anhydrous THF was added 406 μL (2.06 mmol) of diisopropylazodicarboxylate at −20° C. The reaction mixture was stirred for 1 hour, followed by addition of a solution of 0.301 g (1.72 mmol) of 5,7-dimethyl-2-ethylimidazo[4,5-b]pyridine and 0.596 g (1.72 mmol) of the product of Step C in 6 mL THF. The reaction mixture was stirred 20 min at −20° C., then warmed to room temperature and stirred an additional 1 hour. The reaction mixture was then evaporated in vacuo and applied to a silica gel flash chromatography column. Elution with 50% EtOAc-hexane, evaporation of the purified fractions and drying in vacuo afforded 0.440 g (51%) of the title compound.

$^1$H NMR (400 MHz, CDCl$_3$, ppm): δ1.26 (t, J=7.60 Hz, 3H), 2.56 (s, 3H), 2.61 (s, 3H), 2.74 (q, J=7.60 Hz, 2H), 3.08 (dd, J=6.80, 15.60 Hz, 1H), 3.20 (dd, J=6.80, 15.60 Hz, 1H), 3.71 (s, 3H), 4.82–4.94 (m, 2H), 5.30 (s, 2H), 5.53–5.60 (m, 1H), 5.58 (s, 1H), 6.86 (d, J=2.00 Hz, 1H), 6.88 (s, 1H), 6.93 (d, J=2.00 Hz, 1H), 7.32–7.35 (m, 3H), 7.41–7.43 (m, 2H).

FAB-MS: m/e 503 (M+1).

Step E: Preparation of 3-[4-(1-carboxy-1-phenylmethoxy )-3-chloro-5-(prop -2-ene-1-yl)phenylmethyl]-5,7-dimethyl-2-ethyl-3H-imidazo[4,5-b]-pyridine To a magnetically stirred solution of 0.230 g (0.46 mmol) of the product of Step D in 5.0 mL methanol was added 0.5 mL of a 5.0N solution of sodium hydroxide and the reaction was stirred at room temperature 3 hours. The reaction mixture was adjusted to pH=6 with 1.0N hydrochloric acid and then concentrated in vacuo. The residue was then purified on a silica gel flash chromatography column eluted with CHCl$_3$MeOH—NH$_4$OH (80:15:1). Evaporation of the purified fractions and drying in vacuo afforded 0.181 g (81%) of the title compound.

$^1$H NMR (400 MHz, CD$_3$OD, ppm): δ1.22 (t, J=7.60 Hz, 3H), 2.56 (s, 3H), 2.59 (s, 3H), 2.82 (q, J=7.60 Hz, 2H), 2.86 (dd, J=6.80, 15.60 Hz, 1H), 3.07 (dd, J=6.80, 15.60 Hz, 1H), 4.74–4.83 (m, 2H), 4.89 (s, 2H), 5.36 (s, 1H), 5.40–5.48 (m, 1H), 6.80 (d, J=2.00 Hz, 1H), 7.00 (s, 1H), 7.01 (d, J=2.00 Hz, 1H), 7.25–7.29 (m, 3H), 7.37–7.39 (m, 2H).

FAB-MS: m/e 490 (M+1).

EXAMPLE 41

3-[4-(1-Carboxy-1-(3-chlorophenyl)methoxy)-3-chloro-5-propylphenylmethyl]-5,7-dimethyl-2-ethyl-3H-imidazo[4,5-b]pyridine Step A: Preparation of methyl 3-chloro-4-hydroxy-5-propylbenzoate A Parr flask was charged with a solution of 14.784 g (65.2 mmol) of the product of Step A in example 40 disolved in 80 mL ethanol and 0.485 g of 5% rhodium on alumina catalyst was added. The rection mixture was mounted in a Parr hydrogenation apparatus, pressurized to 40 psig hydrogen and shaken for 30 minutes. The reaction vessel was then removed from the apparatus, the contents were filtered and the filtrate was evaporated and dried in vacuo to afford 14.878 (99%) of the title compound.

$^1$H NMR (400 MHz, CDCl$_3$, ppm): δ0.93 (t, J=7.60 Hz, 3H), 1.57-1.70 (m, 2H), 2.63 (t, J=7.60 Hz, 2H), 3.86 (s, 3H), 6.05 (s, 1H), 7.72 (d, J=1.60 Hz, 1H), 7.86 (d, J=1.60 Hz, 1H).

EI-MS: m/e 228 (M+1).

Step B: Preparation of 3-chloro-4-hydroxy-5-propylbenzyl alcohol

To a stirred solution of 14.878 g (65.1 mmol) of the product of Step A in 100 mL methylene chloride was added 8.796 g (72.0 mmol) of 4-dimethylaminopyridine, 10.787 g (71.6 mmol) of tertbutyldimethylchlorosilane and the mixture was stirred at room temperature for 3 hours. The reaction mixture was partitioned between methylene chloride and water, the organic layer was separated washed with 1.0N HCl, 5% NaHCO$_3$, dried (MgSO$_4$), filtered and evaporated. The residue (20.293 g) was dissolved in 60 mL of anhydrous THF, magnetically stirred at 0° C., and then treated with 130 mL of a 1.0M solution of lithium triethylborohydride under a nitrogen atmosphere. The reaction was allowed to warm to room temperature, and treated with several mL water until hydrogen evolution ceased. The reaction mixture was evaporated in vacuo, redissolved in methylene chloride, dried (MgSO$_4$), filtered and reevaporated in vacuo. The residue (16.767 g) was finally redissolved in 50 mL THF and treated with 53.2 mL of a 1.0M solution of tetrabutylammonium fluoride in THF while stirring for 12 hours at room temperature. The reaction mixture was then evaporated to an oil and purified on a silica gel flash chromatography column eluted with 25% EtOAc-hexane to afford 8.877 g (70%) of the title compound.

$^1$H NMR (400 MHz, CDCl$_3$, ppm): δ0.93 (t, J=7.60 Hz, 3H), 1.57-1.63 (m, 2H), 2.59 (t, J=7.60 Hz, 2H), 4.10 (br s, 2H), 4.51 (d, J=3.60 Hz, 2H), 6.98 (s, 1H), 7.14 (s, 1H).

EI-MS: m/e 200 (M+1).

Step C: Preparation of methyl 2-(2-chloro-4-hydroxymethyl-6-propyl-phenoxy) -2-(3-chlorophenyl)acetate To a magnetically stirred solution of 0.600 g (2.99 mmol) of the product of Step B in 6 mL acetone was added 0.869 g (3.30 mmol) of methyl α-bromo-(3-chlorophenyl)acetate, 0.829 g (6.00 mmol) of potassium carbonate and the reaction mixture was heated at reflux for 4 hours. The reaction mixture was cooled to room temperature, filtered and evaporated. The residue was purified on a silica gel flash chromatography column eluted with 15% EtOAc-hexane. Evaporation of the purified fractions and drying in vacuo afforded 0.925 g (80%) of the title compound.

$^1$H NMR (400 MHz, CDCl$_3$, ppm): δ0.79 (t, J=7.60 Hz, 3H), 1.25-1.37 (m, 1H), 1.42-1.53 (m, 1H), 2.27-2.35 (m, 1H), 2.38-2.46 (m, 1H), 3.73 (s, 3H), 4.56 (s, 2H), 5.48 (s, 1H), 6.98 (d. J=2.00 Hz, 1H), 7.21 (d, J=2.00 Hz, 1H), 7.24-7.38 (m, 3H), 7.51-7.53 (m, 1H).

Step D: Preparation of methyl 2-(4-bromomethyl-2-chloro-6-propylphenoxy) -2-(3-chlorophenyl)acetate To a solution of 0.925 g (2.41 mmol) of the product of Step B dissolved in 5.0 mL of carbon tetrachloride was added 115 μL (1.21 mmol) of phosphorous tribromide and the reaction mixture was stirred at room temperature for 20 minutes. Carbon tetrachloride was evaporated from the reaction mixture several times to remove the hydrogen bromide, then the residue was purified on a silica gel flash chromatography column eluted with 10% EtOAc-hexane. The purified fractions were evaporated in vacuo affording 0.814 g (76%) of the title compound.

$^1$H NMR (400 MHz, CDCl$_3$, ppm): δ0.80 (t, J=7.60 Hz, 3H), 1.25-1.36 (m, 1H), 1.43-1.53 (m, 1H), 2.28-2.37 (m, 1H), 2.42-2.50 (m, 1H), 3.73 (s, 3H), 4.35 (s, 2H), 5.49 (s, 1H), 7.03 (d, J=2.00 Hz, 1H), 7.24 (d, J=2.00 Hz, 1H), 7.28-7.39 (m 3H), 7.51-7.54 (m, 1H).

Step E: Preparation of 3-[4-(1-carbomethoxy-1-(3-chlorophenyl)methoxy) -3-chloro-5-propylphenylmethyl]-5,7-dimethyl-2-ethyl -3H-imidazo-[4,5-b]pyridine To a solution of 0.085 g (0.49 mmol) of 5,7-dimethyl-2-ethylimidazo[4,5-b]pyridine in 1.0 mL anhydrous DMF was added 21.0 mg (0.54 mmol) of a 60% oil dispersion of sodium hydride and the reaction mixture was stirred under a nitrogen atmosphere at room temperature for 1 hour. A solution of 0.250 g (0.56 mmol) of the product of Step C in 0.5 mL of DMF was added and the reaction was stirred an additional 2 hours at room temperature. The reaction mixture was partitioned between EtOAc and water, separated, dried (MgSO$_4$), filtered and evaporated. The residue was purified on a silica gel flash chromatography column eluted with 50% EtOAc-hexane. Evaporation of the purified fractions and drying in vacuo afforded 0.150 g (58%) of the title compound.

$^1$H NMR (400 MHz, CDCl$_3$, ppm): δ0.74 (t, J=7.60 Hz, 3H), 1.22-1.31 (m, 1H), 1.27 (t, J=7.60 Hz, 3H), 1.34-1.44 (m, 1H), 2.24-2.31 (m, 1H), 2.34-2.42 (m, 1H), 2.56 (s, 3H), 2.62 (s, 3H), 2.75 (q, J=7.60 Hz, 2H), 3.71 (s, 3H), 5.31 (s, 2H), 5.45 (s, 1H), 6.81 (d, J=2.00 Hz, 1H), 6.88 (s, 1H), 6.94 (d, J=2.00 Hz, 1H), 7.24-7.35 (m, 3H), 7.46-7.48 (m, 1H).

FAB-MS: m/e 540 (M+1).

Step F: Preparation of 3-[4-(1-carboxy-1-(3-chlorophenyl)methoxy) -3-chloro-5-propylphenylmethyl]-5,7-dimethyl-2-ethyl-3H-imidazo[4,5-b]pyridine To a magnetically stirred solution of 0.150 g (0.28 mmol) of the product of Step D in 3.0 mL methanol was added 0.5 mL of a 5.0N solution of sodium hydroxide and the reaction was stirred at room temperature for 6 hours. The reaction mixture was adjusted to pH=6 with 1.0N hydrochloric acid and then concentrated in vacuo. The residue was then purified on a silica gel flash chromatography column eluted with CHCl$_3$-MeOH—NH$_4$OH (80: 15:1). Evaporation of the purified fractions and drying in vacuo afforded 0.105 g (72%) of the title compound.

$^1$H NMR (400 MHz, CD$_3$OD, ppm): δ0.71 (t, J=7.60 Hz, 3H). 1.06-1.18 (m, 1H), 1.23 (t, J=7.60 Hz, 3H), 1.34-1.43 (m, 1H), 2.22-2.28 (m, 2H), 2.56 (s, 3H), 2.59 (s, 3H), 2.83 (q, J=7.60 Hz, 2H), 5.29 (s, 1H), 5.43 (s, 2H), 6.84 (d, J=2.00 Hz, 1H), 6.98 (d, J=2.00 Hz, 1H), 7.00 is, 1H), 7.23-7.34 (m, 3H), 7.47-7.49 (m, 1H).

FAB-MS: m/e 526 (M+1).

EXAMPLE 42

3-[4-(1-(3-Chlorophenyl)-1-phenylsulfonylaminocarbonyl)methoxy-3,5-dipropylphenylmethyl]-5,7-dimethyl-2-ethyl-3H-imidazo 4,5 -b]pyridine Step A: Preparation of 3-[4-(1-(3-chlorophenyl)-1-phenylsulfonyl-aminocarbonyl)methoxy -3,5-dipropylphenylmethyl]-5,7-dimethyl-2-ethyl-3H-imidazo[4,5-b]pyridine A 15 mL capacity high pressure vessel equipped with a magnetic stir bar was charged with a solution of 0.114 g (0.27 mmol) of the product of Example 17 in 2.0 mL of anhydrous THF and 0.066 g (0.41 mmol) of 1,1'-carbonyldiimidazole was added. The vessel was sealed and the contents were stirred and heated at 80° C. for 1 hour. The reaction was then cooled to room temperature, opened and 0.064 g (0.41 mmol) of benzenesulfonamide and 81 μL (0.53 mmol) of 1,8-diazabicyclo[5.4.-0]undec-7-ene were added. The reaction vessel was resealed and then stirred and heated at 80° C. for an additional 2 hours. The reaction vessel was then cooled, opened and the contents were partitioned between water and EtOAc. The organic layer was separated washed with 10% aqueous NaHSO$_4$, brine, dried (MgSO$_4$), filtered and evaporated. The residual oil was purified on a silica gel flash chromatography column eluted with CHCl$_3$-MeOH—NH$_4$OH (90:10:1) to afford 0.074 g (50%) of the title compound.

$^1$H NMR (400 MHz, CD$_3$OD, ppm): δ0.66 (t, J=7.60 Hz, 6H), 1.19 (t, J=7.60 Hz, 3H), 1.15–1.24 (m, 2H), 1.27–1.40 (m, 2H), 2.10–2.25 (m, 4H 2.56 (s, 3H), 2.59 (s, 3H), 2.81 (q, J=7.60 Hz, 2H), 4.95 (s, 2H), 5.41 (s, 1H), 6.71 (s, 1H), 6.99–7.56 (m, 8H), 7.74–7.90 (m, 3H).

FAB-MS: m/e 673 (M+1).

EXAMPLE 43

3-[4-(1-(3–Chlorophenyl)-1-(5-tetrazolyl)aminocarbonyl)methoxy-3,5-dipropylphenylmethyl]-5,7-dimethyl-2-ethyl-3H-imidazo[4,5-b]pyridine Step A: Preparation of 3-[4-(1-(3-chlorophenyl)-1-(5-tetrazolyl)aminocarbonyl)methoxy-3,5-dipropylphenylmethyl]-5,7-dimethyl -2-ethyl-3H-imidazo[4,5-b]pyridine A 15 mL capacity high pressure vessel equipped with a magnetic stir bar was charged with a solution of 0.121 g (0.23 mmol) of the product of Example 17 in 1.0 mL of anhydrous DMF and 0.083 g (0.51 mmol) of 1,1'-carbonyldiimidazole was added. The vessel was sealed and the contents were stirred and heated at 80° C. for 1 hour. The reaction was then cooled to room temperature, opened and 0.024 g (0.28 mmol) of 5-aminotetrazole and 85 μL (0.57 mmol) of 1,8-diazabicyclo[5.4.-0]undec-7-ene were added. The reaction vessel was resealed and then stirred and heated at 80° C. for an additional 1 hour. The reaction vessel was then cooled, opened and the contents were partitioned between water and EtOAc. The organic layer was separated washed with 10% aqueous NaHSO$_4$, brine, dried (MgSO$_4$), filtered and evaporated. The residual oil was purified on a silica gel flash chromatography column eluted with CHCl$_3$—MeOH—NH$_4$OH (85:15:1) to afford 0.051 g (37%) of the title compound.

$^1$H NMR (400 MHz, CD$_3$OD, ppm): δ0.74 (t, J=7.60 Hz, 6H), 1.20 (t, J=7.60 Hz, 3H), 1.25–1.48 (m, 4H), 2.30 (t, J=7.60 Hz, 4H), 2.57 (s, 3H), 2.60 (s, 3H), 2.83 (q, J=7.60 Hz, 2H), 4.93 (s, 1H), 5.43 (s, 2H), 6.75 (s, 2H), 7.01 (s, 1H), 7.28–7.36 (m, 3H), 7.43 (s, 1H), 7.51 (s, 1H).

FAB-MS: m/e 607 (M+Li).

EXAMPLE 44

3-[4-(1-Phenyl-1-(5-tetrazolyl)methoxy)-3,5-dipropylphenylmethyl]-5,7-dimethyl-2-ethyl-3H-imidazo[4,5-b]pyridine Step A: Preparation of 3-[4-(1-cyano-1-phenylmethoxy)-3,5-dipropylphenylmethyl]-5,7-dimethyl-2-ethyl-3H-imidazo[4,5-b]pyridine To a solution of 0.250 g (0.50 mmol) of the product of Step I in Example 13 dissolved in 2.0 mL methylene chloride was added 46 μL (0.53 mmol) of chlorosulfonylisocyanate and the mixture was stirred and refluxed under a nitrogen atmosphere for 2.5 hours. The reaction was cooled to room temperature, 80 μL (1.03 mmol) of DMF was added and the reaction mixture was stirred overnight. Methanol (0.5 mL) was added, the reaction mixture was stirred briefly and then evaporated in vacuo. The residue was purified on a silica gel flash chromatography column eluted with 40% EtOAc-hexane. Evaporation of the purified fractions and drying in vacuo afforded 0.073 g (30%) of the title compound.

$^1$H NMR (400 MHz, CDCl$_3$, ppm): Consistent with structure.

FAB-MS: m/e 481 (M+1).

Step B: Preparation of 3-[4-(1-phenyl-1-(5-tetrazolyl)methoxy)-3,5-dipropylphenyl]methyl-5,7-dimethyl-2-ethyl-3H-imidazo[4,5-b]-pyridine To a solution of 0.130 g (0.27 mmol) of the product of Step A in 0.5 mL toluene was added 0.111 g (0.54 mmol) of trimethyltinazide and the reaction mixture was stirred and heated at reflux for 12 hours. The reaction was cooled to room temperature, evaporated in vacuo and the residue was purified on a silica gel flash chromatography column eluted with CHCl$_3$—MeOH—AcOH (100:2:1). The semi-purified fractions were combined evaporated and further purified on a second flash chromatography column eluted with CHCl$_3$—McOH—NH$_4$OH (80:15:1). Evaporation of the purified fractions and drying in vacuo afforded 0.047 g (33%) of the title compound.

$^1$H NMR (400 MHz, CD$_3$OD, ppm): δ0.72 (t, J=7.60 Hz, 6H), i.20 (t, J=7.60 Hz, 3H), 1.25–1.46 (m, 4H), 2.28 (t, J=7.60 Hz, 4H), 2.57 (s, 3H), 2.60 (s, 3H), 2.82 (q, J=7.60 Hz, 2H), 4.93 (s, 1H), 5.43 (s, 2H), 6.74 (s, 2H), 7.01 (s, 1H), 7.28–7.33 (m, 3H), 7.42–7.46 (m, 2H).

FAB-MS: m/e 524 (M+1).

General procedure for resolution of phenoxyphenylacetic acids:

EXAMPLE 45

(+)-3-[4-(1-Carboxy-1-(3-chlorophenyl)methoxy)-3,5-dipropylphenylmethyl]-5,7-dimethyl-2-ethyl-3H-imidazo[4,5-b]pyridine Step A: Preparation of diastereoisomeric oxazolidinones A magnetically stirred solution of 1.532 g (2.87 mmol) of the product of Example 18 in 22 mL of THF was cooled to −78° C. and 0.52 mL (3.73 mmol) of triethylamine followed by 0.39 mL (3.16 mmol) of pivaloyl chloride were added by syringe. The resulting slurry was stirred at −78° C. for 15 min and 0° C. for 45 min and then recooled to −78° C. In a separate flask, 0.915 g (5.16 mmol) of (4S)-4-benzyl-2-oxazolidinone was dissolved in 11.5 mL THF, cooled to −78° C. and 2.07 mL of a 2.5M solution of η-butyllithium in hexane was added. The lithiated oxazolidinone was added to the stirred slurry in the first reaction mixture by cannula, stirred at −78° C. for 15 min and then allowed to warm to room temperature over 2 hours. The reaction was quenched by addition of 25 mL of 1N aqueous NaHSO$_4$, and the THF was removed in vacuo. The remaining aqueous layer was extracted with EtOAc, the organic layer was separated, washed with saturated brine, dried (MgSO$_4$), filtered and evaporated. The residue was purified by MPLC on an E. Merck LiChroprep silica gel column (25×3 10 mm, 40–63 μM) eluted with 35% EtOAc-hexane and monitored with a Waters Associates R[403] refractive index detector. Center fractions of the two eluted bands were separately evaporated and dried in vacuo to afford 0.320 g of the less polar diastereoisomer and 0.218 g of the more polar diastereoisomer. The remainder of the acyloxazolidinone fractions were combined, evaporated and dried in vacuo to afford an additional 0.931 g (73% total) of the title compounds.

Step B: Hydrolysis of diastereoisomerically pure oxazolidinones. Preparation of (+)-3-[4-(1-carboxy-1-(3-chlorophenyl)methoxy) -3,5-dipropylphenylmethyl]-5,7-dimethyl-2-ethyl-3H-imidazo[4,5-b]-pyridine To a solution of 0.110 g (0.16 mmol) of the purified less polar diastereoisomer from Step A in 3.2 mL of a 3:1 mixture of THF-water was added 97 μL (0.95 mmol) of 30% aqueous hydrogen peroxide with stirring at 0° C. Lithium hydroxide monohydrate (0.013 g, 0.32 mmol) was then added and the reaction .mixture was stirred over 30 min and allowed to warm to room temperature. The reaction was then recooled to 0° C. and the excess peroxide was quenched by addition of 0.7 mL (10% excess) of 1.5N $Na_2SO_3$. The reaction mixture was adjusted to pH=6 with $NaHSO_4$, then filtered and the filtrate was injected directly onto a Waters Radial-Pak HPLC column (Delta-Pak $C_{18}$ 10 mm×25 cm cartridge). The column was then eluted isocratically at 15 mL/min with 60/40 A/B (where A=95/5 $H_2O/CH_3CN$ containing 0.1% HOAc and B=95/5 $CH_3CN/H_2O$ containing 0.1% HOAc) for 10 min to desalt and elute the cleaved chiral auxilliary. The solvent composition was then stepped to 20/80 A/B and eluted for approximately 5 min which eluted the product. Excess acetonitrile was removed from the product containing fractions and the residue was lyophilized to afford 0.041 g (48%) of the title compound.

[α]D = +104.5° (c=1.1, $CHCl_3$).

$^1$H NMR (400 MHz, $CD_3OD$, ppm): δ0.74 (t, J=7.60 Hz, 6H), 1.21 (t, J=7.60 Hz, 3H), 1.26–1.49 (m, 4H), 2.28–2.34 (m, 4H), 2.57 (s, 3H), 2.60 (s, 3H), 2.86 (q, J=7.60 Hz, 2H), 5.05 (s, 1H), 5.45 (s, 2H), 6.79 is, 2H), 7.04 (s, 1H), 7.34–7.39 (m, 3H), 7.50 (br s, 1H).

FAB-MS: m/e 534 (M+1).

EXAMPLE 46

(−)-3-[4-(1-Carboxy-1-(3-chlorophenyl)methoxy)-3,5-dipropylphenylmethyl]-5,7-dimethyl-2-ethyl-3H-imidazo[4,5-b]pyridine Step A: Hydrolysis of diastereoisomerically pure oxazolidinones. Preparation of (−)-3-[4-(1-carboxy-1-(3-chlorophenyl)methoxy) -3,5-dipropylphenylmethyl]-5,7-dimethyl-2-ethyl3H-imidazo[4,5 -b]-pyridine The more polar diastereoisomer (0.094 g, 0.14 mmol) obtained in Step A of Example 45 was hydrolyzed in 2.7 mL of 3:1 THF/$H_2O$ using 30% $H_2O_2$ (84 μL) and LiOH.$H_2O$ (0.0115 g, 0.27 mmol), quenched with 0.55 mL of 1.5N $Na_2SO_3$, and purified according to the procedure described in Step B of Example 45 to afford 0.039 g (53%) of the title compound.

[α]D = −100.8° (c=1.0, $CHCl_3$).

$^1$H NMR (400 MHz, $CD_3OD$, ppm): identical to dextrorotatory enantiomer.

FAB-MS: m/e 534 (M+1).

EXAMPLE 47

3-[4-(1-Carboxy-1-(3-chlorophenyl)methoxy)-3,5-dimethylphenylmethyl]-5,7-dimethyl-2-ethyl-3H-imidazo[4,5-b]pyridine Step A: Preparation of methyl 2-(2,6-dimethyl-4-formylphenoxy)-2-(3-chlorophenyl)acetate To a solution of 1.260 g (4.80 mmol) of methyl α-bromo-(3-chlorophenyl)acetate and 0.600 g (4.00 mmol) of 3,5-dimethyl-4-hydroxybenzaldehyde in 16 mL acetone was added 1.10 g (8.00 mmol) of potassium carbonate and the resulting mixture was stirred and heated at reflux for 3.5 hours. The reaction mixture was cooled to room temperature, filtered and concentrated in vacuo. The residue was purified on a silica gel flash chromatography column eluted with 30% EtOAc-hexane. The purified fractions were combined, evaporated and dried in vacuo to afford 1.260 g (95%) of the title compound.

$^1$H NMR (400 MHz, $CDCl_3$, ppm): δ2.20 (s, 6H), 3.74 (s, 3H), 5.23 (s, 1H), 7.33–7.37 (m, 3H), 7.50–7.51 (br s, 3H), 9.85 (s, 1H).

EI-MS: m/e 332 (M+).

Step B: Preparation of methyl 2-(2,6-dimethyl-4-hydroxymethylphenoxy)-2-(3-chlorophenyl)acetate To a solution of 1.260 g (3.79 mmol) of the product of Step A in 8 mL methanol was added 0.072 g (1.90 mmol) of sodium borohydride and the reaction mixture was stirred at room temperature for 15 minutes. Excess borohydride was quenched with water, and the reaction mixture was extracted into EtOAc. The organic layer was dried ($MgSO_4$), filtered, evaporated, and then purified on a silica gel flash chromatography column eluted with 30% EtOAc-hexane. The purified fractions were combined, evaporated and dried in vacuo to afford 0.790 g (63%) of the title compound.

$^1$H NMR (400 MHz, $CDCl_3$, ppm): δ2.10 (s, 6H), 3.73 (s, 3H), 4.55 (s, 2H), 5.15 (s, 1H), 6.95 (s, 2H), 7.30–7.38 (m, 3H), 7.50 (br s, 1H).

EI-MS: m/e 334 (M+).

Step C: Preparation of methyl 2-(4-bromomethyl-2,6-dimethylphenoxy) -2-(3-chlorophenyl)acetate To a solution of 0.560 g (1.62 mmol) of the product of Step B dissolved in 5.0 mL of carbon tetrachloride was added 154 μL (1.62 mmol) of phosphorous tribromide and the reaction mixture was stirred at room temperature for 5 minutes. Carbon tetrachloride was evaporated from the reaction mixture several times to remove the hydrogen bromide, then the residue was purified on a silica gel flash chromatography column eluted with 5% EtOAc-hexane. The purified fractions were evaporated in vacuo affording 0.523 g (81%) of the title compound.

$^1$H NMR (400 MHz, $CDCl_3$, ppm): δ2.09 (s, 6H), 3.73 (s, 3H), 4.38 (s, 2H), 5.15 (s, 1H), 6.99 (s, 2H), 7.30–7.38 (m, 3H), 7.50 (br s, 1H).

EI-MS: m/e 396, 398 (M+, 1:1 ratio).

Step D: Preparation of 3-[4-(1-carbomethoxy-1-(3-chlorophenyl)methoxy) -3,5-dimethylphenylmethyl]-5,7-dimethyl-2-ethyl-3H-imidazo[4.5-b]-pyridine To a solution of 0.142 g (0.81 mmol) of 5,7-dimethyl-2-ethylimidazo [4,5-β]pyridine in 4.0 mL anhydrous DMF was added 32.5 mg (0.81 mmol) of a 60% oil dispersion of sodium hydride and the reaction mixture was stirred under a nitrogen atmosphere at room temperature for 30 minutes. A solution of 0.323 g (0.81 mmol) of the product of Step C in 6.2 mL of DMF was added and the reaction was stirred an additional 1 hour at room temperature. The reaction mixture was partitioned between EtOAc and water, separated, dried (MgSO₄), filtered and evaporated. The residue was purified on a silica gel flash chromatography column eluted with 50% EtOAc-hexane. Evaporation of the purified fractions and drying in vacuo afforded 0.284 g (71%) of the title compound.

¹H NMR (400 MHz, CDCl₃, ppm): δ1.26 (t, J=7.60 Hz, 3H), 2.00 (s, 6H), 2.58 (s, 3H), 2.63 (s, 3H), 2.76 (q, J=7.60 Hz, 2H), 3.71 (s, 3H), 5.11 (s, 1H), 5.32 (s, 2H), 6.69 (s, 2H), 6.90 (s, 1H), 7.25–7.34 (m, 3H), 7.45 (br s, 1H).

FAB-MS: m/e 492 (M+1).

Step E: Preparation of 3-[4-(1-carboxy-1-(3-chlorophenyl)methoxy) -3,5-dimethylphenylmethyl]-5,7-dimethyl-2-ethyl-3H-imidazo[4,5-b]-pyridine To a magnetically stirred solution of 0.280 g (0.56 mmol) of the product of Step D in 4.0 mL methanol was added 0.5 mL of a 5.0N solution of sodium hydroxide and the reaction was stirred at room temperature for 1.5 hours. The reaction mixture was adjusted to pH=6 with 1.0N hydrochloric acid and then concentrated in vacuo. The residue was then purified on a silica gel flash chromatography column eluted with CHCl₃—MeOH—NH₄OH (80:15:1). Evaporation of the purified fractions and drying in vacuo afforded 0.238 g (87%) of the title compound.

¹H NMR (400 MHz, CD₃OD, ppm): δ1.21 (t, J=7.60 Hz, 3H), 1.96 (s, 6H), 2.57 (s, 3H), 2.59 (s, 3H), 2.81 (q, J=7.60 Hz, 2H), 5.00 (s, 1H), 5.40 (s, 2H), 6.70 (s, 2H), 7.01 (s, 2H), 7.27–7.30 (m, 3H), 7.43 (br s. 1H).

EI-MS: m/e 478 (M⁺).

EXAMPLE 48

3-[4-(1-Carboxy-1-(2-phenylethyl)methoxy)-3,5-dipropylphenylmethyl]-5,7-dimethyl-2-ethyl-3H-imidazo[4,5-b]pyridine Step A: Preparation of 3-[4-(1-carboethoxy-1-(2-phenylethyl)methoxy) -3,5-dipropylphenylmethyl]-5,7-dimethyl-2-ethyl-3H-imidazo[4,5-b]-pyridine To a stirred solution of 0.150 g (0.41 mmol) of 5,7-dimethyl-2-ethyl -3-[4-hydroxy-3,5-dipropylphenyl]-methyl-3H-imidazol[4,5-β]pyridine (Step G of Example 13) and 0.127 g (0.49 mmol) of ethyl α-bromo-4-phenylbutanoate in 2 mL anhydrous DMF was added 0.290 g (0.82 mmol) cesium carbonate and the reaction mixture was stirred and heated at 60° C. for 4 hours under a nitrogen atmosphere. The reaction mixture was cooled to room temperature, diluted with methylene chloride, filtered, and evaporated in vacuo. The residue was then purified on a silica gel flash chromatography column eluted with 30% EtOAc-hexane. The purified fractions were combined, evaporated and dried in vacuo to afford 0.145 g (64%) of the title compound.

¹H NMR (200 MHz, CDCl₃, ppm): δ0.85 0, J=7.6 Hz, 6H), 1.20 (t, J=7.6 Hz, 3H), 1.25 (t, J=7.6 Hz, 3H), 1.42–1.55 (m, 4H), 2.16–2.30 (m, 2H), 2.45–2.70 (m, 6H), 2.56 (s, 3H), 2.62 (s, 3H), 2.80 (q, J=7.6 Hz, 2H), 4.12 (q, J=7.6 Hz, 2H), 4.35 (t, J=6.8 Hz, 1H), 5.36 (s, 2H), 6.79 (s, 2H), 6.90 (s, 1H), 7.10–7.42 (m, 5H).

FAB-MS: m/e 556 (M+1).

Step B: Preparation of 3-[4-(1-carboxy-1-(2-phenylethyl)methoxy) -3,5-dipropylphenylmethyl]-5,7-dimethyl-2-ethyl-3H-imidazo [4,5-b]-pyridine To a magnetically stirred solution of 0.138 g (0.25 mmol) of the product of Step A in 1.0 mL ethanol was added 0.5 mL of a 5.0N solution of sodium hydroxide and the reaction was stirred at room temperature overnight. The reaction mixture was adjusted to pH=6 with 1.0N hydrochloric acid and then concentrated in vacuo. The residue was then purified on a silica gel flash chromatography column eluted with CHCl₃—MeOH—NH₄OH (80:15:1). Evaporation of the purified fractions and drying in vacuo afforded 0.103 g (79%) of the title compound.

¹H NMR (400 MHz, CD₃OD, ppm): δ0.84 (t, J=7.20 Hz, 6H), 1.20 (t, J=7.60 Hz, 3H), 1.45–1.55 (m, 4H), 2.08–2.14 (m, 2H), 2.50–2.68 0n, 6H), 2.57 (s, 3H), 2.60 (s, 3H), 2.83 (q, J=7.60 Hz, 2H), 4.27 (dd, J=5.20, 6.80 Hz, 1H), 5.44 (s, 2H), 6.77 (s, 2H), 7.01 (s, 1H), 7.11–7.15 (m, 3H), 7.20–7.24 (m, 2H).

FAB-MS: m/e 528 (M+1).

What is claimed is:

1. A method of treating asthma in a mammal, the treatment of which is effected or facilitated by a decrease in endothelin mediated actions, comprising the administration, in an amount that is effective for antagonizing the effect of endothelin, of a compound of structural formula II, wherein:

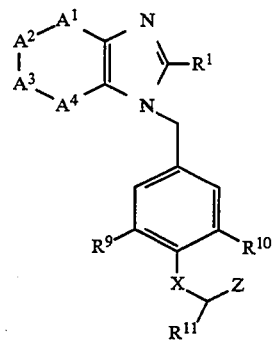

wherein,
—A¹—A²—A³—A⁴— is:

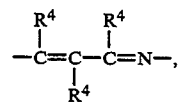
(a)

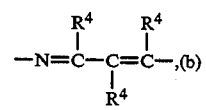
(b)

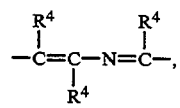
(c)

or

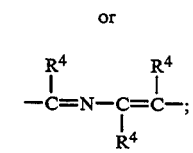
(d)

E is a single bond; and
R¹ is:
 (a) (C₁–C₆)-alkyl, (C₂–C₆)-alkenyl or (C₂–C₆)-alkynyl each of which is unsubstituted or substituted with a substituent selected from the group consisting of:
  i) phenyl or naphthyl as defined in R¹(b), ii) $(C_3-C_7)$-cycloalkyl,
iii) Cl, Br, I, F,
iv) OH,
v) $NH_2$,
vi) $NH(C_1-C_4)$-alkyl,
vii) $N[(C_1-C_4)$-alkyl$]_2$,
viii) $NHSO_2R^2$,
ix) $CF_3$,
x) $COOR^2$, or
xi) $SO_2NHR^{2a}$; and
(b) phenyl or naphthyl which is unsubstituted, mono- or disubstituted with substituents selected from the group consisting of:
i) Cl, Br, I, F,
ii) $(C_1-C_4)$-alkyl,
iii) $(C_1-C_4)$-alkoxy,
iv) $NO_2$,
v) $CF_3$,
vi) $SO_2NR^{2a}R^{2a}$,
vii) $(C_1-C_4)$-alkylthio,
viii) hydroxy,
ix) amino,
x) $(C_3-C_7)$-cycloalkyl,
xi) $(C_3-C_{10})$-alkenyl; and $R^2$ is:
(a) H,
(b) $(C_1-C_6)$-alkyl; and $R^{2a}$ is:
(a) $R^2$,
(b) benzyl, or
(c) phenyl; and $R^4$ groups are independently:
(a) H,
(b) $(C_1-C_6)$-alkyl, which is unsubstituted or substituted with:
i) OH,
ii) $CO_2R^{2a}$,
iii) $NH_2$,
iv) $(C_1-C_4)$-alkylamino,
v) di[$(C_1-C_4)$-alkyl]amino,
(c) Cl, Br, I, F,
(d) $CF_3$,
(e) $CO_2R^{2a}$,
(f) $C(=O)NR^{2a}R^{2a}$,
(g) $(C_3-C_7)$-cycloalkyl,
(h) —C(=O)-phenyl or —C(=O)-naphthyl,
(i) —$OR^{22}$,
(j) —$N[(C_1-C_4)$-alkyl$]_2$,
(k) —$NHC(=O)(C_1-C_4)$-alkyl,
(l) —$NHCO_2(C_1-C_4)$-alkyl,
(m) —$SO_2NH$—$(C_1-C_4)$-alkyl,
(n) —$SO_2NH$-aryl,
(o) —$NO_2$,
(p) —$NHSO_2CH_3$, $R^5$ is:
(a) H, or
(b) $(C_1-C_6)$-alkyl, unsubstituted or substituted with: hydroxyl, or $CO_2R^2$; and $R^{5a}$ is
(a) H,
(b) $(C_1-C_4)$-alkyl, or
(c) $(C_1-C_4)$-acyl; and $R^{6a}$ is:
(a) H, or
(b) $(C_1-C_4)$-alkyl; and $R^9$ and $R^{10}$ are independently:
(a) H,
(b) $(C_1-C_6)$-alkyl, unsubstituted or substituted with $(C_3-C_7)$-cycloalkyl,
(c) $(C_2-C_6)$-alkenyl,
(d) $(C_2-C_6)$-alkynyl,
(e) Cl, Br, F, I,
(f) $(C_1-C_6)$-alkoxy,
(g) when $R^9$ and $R^{10}$ are on adjacent carbons, they can be joined to form an aryl ring,
(C_1-C_6)-perfluoroalkyl,
(i) $(C_3-C_7)$-cycloalkyl, unsubstituted or substituted with $(C_1-C_6)$-alkyl, or
(j) phenyl; and X is:
(a) —O—,
(b) —$S(O)_n$—,
(c) —$NR^{13}$—
(d) —$CH_2O$—,
(e) —$CH_2S(O)_n$,
(f) —$CH_2NR^{13}$—, or
(g) single bond; and $R^{11}$ is:
(a) phenyl or naphthyl which is unsubstituted, mono- or disubstituted with substituents selected from the group consisting of:
i) Cl, Br, I, F,
ii) $(C_1-C_4)$-alkyl,
iii) $(C_1-C_4)$-alkoxy,
iv) $NO_2$,
v) $CF_3$,
vi) $SO_2NR^{2a}R^{2a}$,
vii) $(C_1-C_4)$-alkylthio,
viii) hydroxy,
ix) amino,
x) $(C_3-C_7)$-cycloalkyl,
xi) $(C_3-C_{10})$-alkenyl;
(b) phenyl-$(C_1-C_2)$-alkyl or naphthyl-$(C_1-C_2)$-alkyl which is unsubstituted, mono- or disubstituted with the substituents defined in $R^{11}$ (a) above, or $R^{13}$ is:
(a) H,
(b) $(C_1-C_6)$-alkyl,
(c) phenyl or naphthyl as defined in $R^1$(b),
(d) phenyl-$(C_1-C_6)$-alkyl-$(C=O)$— or naphthyl-$(C_1-C_6)$-alkyl -$(C=O)$—, or
(e) $(C_1-C_6)$-alkyl—$(C=O)$—; and Z is:
(a) —$CO_2H$,
(b) —$CO_2$—$(C_1-C_6)$-alkyl,
(c) -tetrazol-5-yl,
(d) —$CONH$(tetrazol-5-yl),
(e) —$CONHSO_2$-phenyl or —$CONHSO_2$-naphthyl, wherein phenyl or naphthyl is unsubstituted or substituted as defined in $R^1$(b),
(f) —$CONHSO_2$—$(C_1-C_4)$-alkyl,
(g) —$CONHSO_2$—$(C_1-C_4)$-perfluoroalkyl,
(h) —$CONHSO_2$-heteroaryl, where in heteroaryl is a 5 or 6 membered aromatic ring containing one or two heteroatoms selected from the group consisting of O, N, or S, or
(i) —$CONHSO_2NR^{2a}R^{2a}$.

2. The method as recited in claim 1, wherein the compound is selected from the formula:

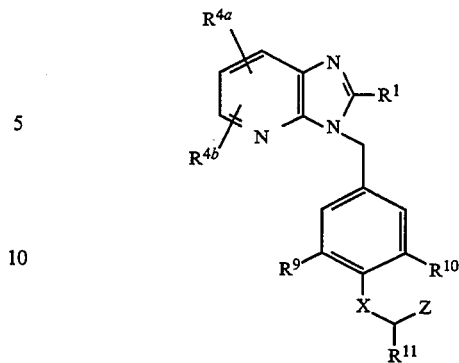

wherein X is 0 in the table below:

| R¹ | R$^{4a}$ | R$^{4b}$ | R⁹ | R¹⁰ | R¹¹ | Z |
|---|---|---|---|---|---|---|
| Et | 5-Me | 7-Me | Pr | Pr | Ph | COOH |
| Et | 5-Me | 7-Me | Me | Me | (3-Me)Ph | COOH |
| Pr | 6-PhCONH | H | Bu | H | (3-Me)Ph | COOH |
| Et | 5-Me | 7-Me | Pr | H | (3-Me)Ph | COOH |
| Et | 5-Me | 7-Me | Cl | H | (3-Me)Ph | COOH |
| Et | 5-Me | 7-Me | Br | Br | (3-Me)Ph | COOH |
| Ph | H | H | Cl | Cl | (3-Me)Ph | COOH |
| Me | H | H | Br | Br | (3-Me)Ph | COOH |
| Et | 5-Me | 7-Me | Pr | Pr | (3-Me)Ph | COOH |
| Et | 5-Me | 7-Me | Pr | Pr | (4-Me)Ph | COOH |
| Et | 5-Me | 7-Me | Me | Me | (3-Cl)Ph | COOH |
| Et | 5-Me | 7-Me | Bu | H | (3-Cl)Ph | COOH |
| Bu | H | H | Cl | Cl | (3-Cl)Ph | COOH |
| Me | 5-Me | 7-Me | Br | Br | (3-Cl)Ph | COOH |
| Et | 5-Me | 7-Me | Pr | Pr | (3-Cl)Ph | COOH |
| Pr | 5-Me | 7-Me | Pr | H | (4-Cl)Ph | COOH |
| Pr | 5-Me | 7-Me | Pr | H | (2-Cl)Ph | COOH |
| Pr | 5-Me | 7-M3 | Pr | H | (3-Cl)Ph | COOH |
| Et | 5-Me | 7-Me | Pr | H | (2-Me)Ph | COOH |
| Et | 5-Me | 7-Me | Me | Me | (3-Br)Ph | COOH |
| Pr | 6-PhCONH | H | Bu | H | (3-Br)Ph | COOH |
| Et | 5-Me | 7-Me | Cl | Cl | (3-Br)Ph | COOH |
| Me | 5-Me | H | Br | Br | (3-Br)Ph | COOH |
| Ph | H | H | Pr | Pr | (3-Br)Ph | COOH |
| Et | 5-Me | 7-Me | Me | Me | (3-NO₂)Ph | COOH |
| Pr | 6-PhCONH | H | Bu | H | (3-NO₂)Ph | COOH |
| Ph | H | H | Cl | Cl | (3-NO₂)Ph | COOH |
| Me | H | H | Br | Br | (3-SMe)Ph | COOH |
| Ph | H | H | Pr | Pr | (3-SMe)Ph | COOH |
| Bu | H | H | Pr | Pr | (3-Cl)Ph | tetrazol-5-yl |
| Et | 5-Me | 7-Me | Pr | Pr | (3-Cl)Ph | CONHSO₂Me |
| Ph | H | H | Pr | Pr | (3-Br)Ph | CONHSO₂Me |
| Ph | H | H | Pr | Pr | (3-Me)Ph | CONHSO₂Me |
| Me | 5-Me | 7-Me | Pr | Pr | (3-Cl)Ph | CONHSO₂Ph |
| Et | 5-Me | 7-Me | Pr | Pr | (3-Br)Ph | CONHSO₂Ph |
| Et | 5-Me | 7-Me | Pr | H | (3-Cl)Ph | CONHSO₂Ph |
| Et | 5-Me | 7-Me | Br | Br | (3-Cl)Ph | CONHSO₂Ph |
| Et | 5-Me | 7-Me | Pr | Pr | (3,4-di-Cl)Ph | COOH |
| Et | 5-Me | 7-Me | Pr | Pr | (3,4-di-Cl)Ph | CONHSO₂Me |
| Et | 5-Me | 7-Me | Pr | Pr | (3,4-di-Br)Ph | COOH |
| Et | 5-Me | 7-Me | Pr | Pr | (3,4-di-Br)Ph | CONHSO₂Me |
| Et | 5-Me | 7-Me | Pr | Pr | (3-NBn₂)Ph | COOH |
| Et | 5-Me | 7-Me | Pr | Pr | (3-NBn₂)Ph | CONHSO₂Me |
| Et | 5-Me | 7-Me | Pr | Pr | (3-NMe₂)Ph | CONHSO₂Me |
| Ph | 5-Me | H | Pr | Pr | (3,4-di-Cl)Ph | COOH |
| Ph | 5-Me | H | Pr | Pr | (3,4-di-Cl)Ph | CONHSO₂Me |
| Ph | 5-Me | H | Pr | Pr | (3,4-di-Br)Ph | COOH |
| Ph | 5-Me | H | Pr | Pr | (3,4-di-Br)Ph | CONHSO₂Me |
| Ph | 5-Me | H | Pr | Pr | (3-NBn₂)Ph | COOH |
| Ph | 5-Me | H | Pr | Pr | (3-NBn₂)Ph | CONHSO₂Me |
| Et | 5-Me | 7-Me | C₆H₁₁CH₂- | H | Ph | COOH |
| Et | 5-Me | 7-Me | Pr | H | (4-Cl)Ph | COOH |
| Et | 5-Me | 7-Me | Pr | H | (2-MeO)Ph | COOH |
| Et | 5-Me | 7-Me | Pr | H | (2,5-di-Br-3,4-di-MeO)Ph | COOH |
| Et | 5-Me | 7-Me | Pr | Pr | (3-NMe2)Ph | CONHSO₂Me |
| Et | 5-Me | 7-Me | Pr | Pr | 2-Naphthyl | COOH |
| Et | 5-Me | 7-Me | Pr | Pr | 2-Naphthyl | CONHSO₂Me |
| Pr | H | 7-Me | Pr | Pr | 2-Naphthyl | CONHSO₂Me |
| Et | 5-Me | 7-Me | Pr | Pr | (3-OPr)Ph | COOH |
| Et | 5-Me | 7-Me | Pr | Pr | (3-OPr)Ph | CONHSO₂Me |

-continued

| R¹ | R⁴ᵃ | R⁴ᵇ | R⁹ | R¹⁰ | R¹¹ | Z |
|---|---|---|---|---|---|---|
| Pr | H | 7-Me | Pr | Pr | (3-OPr)Ph | CONHSO₂Me |
| Et | H | 7-Me | Pr | Pr | (3-OEt)Ph | COOH |
| Et | H | 7-Me | Pr | Pr | (3-OEt)Ph | CONHSO₂Me |
| Et | 5-Me | 7-Me | Pr | Pr | (3-OEt)Ph | CONHSO₂Me |
| Et | 5-Me | 7-Me | Pr | Pr | (3-OEt)Ph | COOH |
| Et | 5-Me | 7-Me | Pr | Pr | (3-NHCOMe)Ph | COOH |
| Et | 5-Me | 7-Me | Pr | Pr | (3-OiPr)Ph | COOH |
| Et | 5-Me | 7-Me | Pr | Pr | (3-NHCOOMe)Ph | COOH |
| Et | 5-Me | 7-Me | Pr | Pr | (3-Et)Ph | COOH |
| Et | 5-Me | 7-Me | Pr | Pr | (3-NMe₂)Ph | COOH |
| Pr | H | 7-Me | Pr | H | (2,6-diCl)Ph | COOH |
| Pr | H | 7-Me | Cl | H | (2-NO₂)Ph | COOH |
| Pr | H | 7-Me | Pr | H | cyclohexyl | COOH |
| Pr | H | 7-Me | H | H | ProPrl | COOH |
| Pr | H | 7-Me | Cl | Pr | (2-COOH)Ph | COOH |
| Pr | H | 7-Me | Bu | H | (3-Me)Ph | Tetrazol-5-yl |
| Et | 5-Me | 7-Me | Cl | H | (2-Me)Ph | COOH |
| Et | 5-Me | 7-Me | Cl | OMe | Ph | COOH |
| Et | 5-Me | 7-Me | Cl | Cl | Ph | COOH |
| Et | 5-Me | 7-Me | Cl | H | Ph | COOH |
| Et | 5-Me | 7-Me | allyl | H | Ph | COOH |
| Et | 5-Me | 7-Me | Pr | H | Ph | COOH |
| Et | 5-Me | 7-Me | Pr | Pr | (2-Me)Ph | COOH |
| Et | 5-Me | 7-Me | Pr | Pr | (2-Cl)Ph | COOH |
| Et | 5-Me | 7-Me | Pr | Pr | (2-Cl)Ph | COOH |
| Et | 5-Me | 7-Me | Pr | Pr | (4-Cl)Ph | COOH |
| Et | 5-Me | 7-Me | Pr | Pr | (3-Br)Ph | COOH |
| Et | 5-Me | 7-Me | Pr | Pr | (2,5-di-F)Ph | COOH |
| Et | 5-Me | 7-Me | Pr | H | (2,5-di-F)Ph | COOH |
| Et | 5-Me | 7-Me | Pr | Pr | (3,5-di-CF₃)Ph | COOH |
| Et | 5-Me | 7-Me | Pr | Pr | (2-MeO)Ph | COOH |
| Et | 5-Me | 7-Me | Pr | Pr | (3-NMe₂)Ph | COOH |
| Et | 5-COOMe | 7-Me | Pr | H | Ph | COOH |
| Et | 5-COOH | 7-Me | Pr | H | Ph | COOH |
| Et | 5-COOBzl | 7-Me | Pr | H | Ph | COOH | or wherein X is NR¹³ as defined in the table below:

| X | R¹ | R⁴ᵃ | R⁴ᵇ | R⁹ | R¹⁰ | R¹¹ | Z |
|---|---|---|---|---|---|---|---|
| —NMe | Et | 5-Me | 7-Me | H | H | Ph | COOH |
| —NEt | Et | 5-Me | 7-Me | H | H | Ph | COOH |
| —NPr | Ft | 5-Me | 7-Me | H | H | Ph | COOH |
| —NH | Et | 5-Me | 7-Me | H | H | Ph | COOH |
| —N-allyl | Et | 5-Me | 7-Me | H | H | Ph | COOH |
| —N-i-Bu | Et | 5-Me | 7-Me | H | H | Ph | COOH |

-continued

| X | R¹ | R⁴ᵃ | R⁴ᵇ | R⁹ | R¹⁰ | R¹¹ | Z |
|---|---|---|---|---|---|---|---|
| —N—C—Pr | Et | 5-Me | 7-Me | H | H | Ph | COOH |
| —N-Sec-Bu | Et | 5-Me | 7-Me | H | H | Ph | COOH |
| —N-i-Pr | Et | 5-Me | 7-Me | H | H | Ph | COOH |
| —NMe | Et | 5-Me | 7-Me | H | H | Ph | tetrazol-5-yl. |

3. The method as recited in claim 1, wherein the compound is selected from the formula:

| R¹ | R⁴ᵃ | R⁴ᵇ | R⁹ | R¹⁰ | R¹¹ | Z |
|---|---|---|---|---|---|---|
| Bu | 4-Me | H | Me | Me | (3-Me)Ph | COOH |
| Bu | 6-PhCONH | H | Bu | H | (3-Me)Ph | COOH |
| Pr | 4-Me | 7-Me | Pr | H | (3-Me)Ph | COOH |
| Ph | 4-Cl | H | Cl | H | (3-Me)Ph | COOH |
| Ph | 4-Cl | H | Br | Br | (3-Me)Ph | COOH |
| Pr | H | 7-Cl | Cl | Cl | (3-Me)Ph | COOH |
| Me | 4-Cl | H | Br | Br | (3-Me)Ph | COOH |
| Ph | 4-Me | H | Pr | Pr | (3-Me)Ph | COOH |
| Bu | H | H | Pr | H | (4-Me)Ph | COOH |
| Pr | 4-Me | H | Me | Me | (3-Cl)Ph | COOH |

-continued

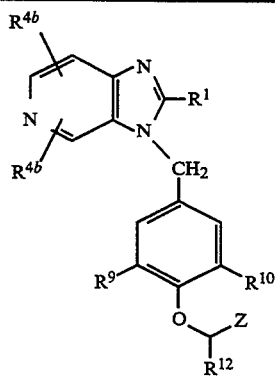

| R¹ | R⁴ᵃ | R⁴ᵇ | R⁹ | R¹⁰ | R¹¹ | Z |
|---|---|---|---|---|---|---|
| Pr | H | 7-Me | Bu | H | (3-Cl)Ph | COOH |
| Ph | 4-Cl | H | Cl | Cl | (3-Cl)Ph | COOH |
| Me | 4-Cl | H | Br | Br | (3-Cl)Ph | COOH |
| Ph | 4-Cl | H | Pr | Pr | (3-Cl)Ph | COOH |
| Et | 4-Me | H | Pr | H | (2-Me)Ph | COOH |
| Ph | 4-Cl | H | Cl | Cl | (3-Br)Ph | COOH |
| Me | 4-Cl | H | Br | Br | (3-Br)Ph | COOH |
| Me | 4-Cl | H | Pr | Pr | (3-Br)Ph | COOH |
| Ph | 4-Cl | H | Me | Me | (3-NO₂)Ph | COOH |
| Me | H | H | Br | Br | (3-SMe)Ph | COOH |
| Ph | H | 7-Cl | Pr | Pr | (3-SMe)Ph | COOH |
| Ph | 4-Cl | H | Pr | Pr | (3-Cl)Ph | tetrazol-5-yl |
| Et | 4-Me | H | Pr | Pr | (3-Cl)Ph | CONHSO₂Me |
| Ph | 4-Cl | H | Pr | Pr | 2-Naphthyl | COOH |
| Ph | 4-Cl | H | Me | Me | 2-Naphthyl | COOH |
| Me | H | H | Br | Br | 2-Naphthyl | COOH |
| Ph | H | 7-Cl | Pr | Pr | 2-Naphthyl | COOH. |

4. The method as recited in claim 1 wherein the compound is selected from the formula:

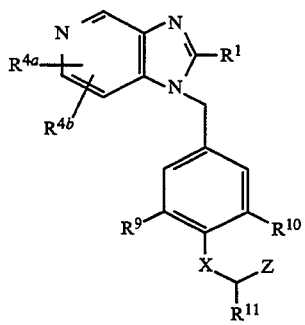

| R¹ | R⁴ᵃ | R⁴ᵇ | R⁹ | R¹⁰ | R¹¹ | Z |
|---|---|---|---|---|---|---|
| Bu | 4-Me | H | Me | Me | (3-Me)Ph | COOH |
| Bu | 6-PhCONH | H | Bu | H | (3-Me)Ph | COOH |
| Pr | 4-Me | 7-Me | Pr | H | (3-Me)Ph | COOH |
| Ph | 4-Cl | H | Cl | H | (3-Me)Ph | COOH |
| Ph | 4-Cl | H | Br | Br | (3-Me)Ph | COOH |
| Pr | H | 7-Cl | Cl | Cl | (3-Me)Ph | COOH |
| Me | 4-Cl | H | Br | Br | (3-Me)Ph | COOH |
| Ph | 4-Me | H | Pr | Pr | (3-Me)Ph | COOH |
| Bu | H | H | Pr | H | (4-Me)Ph | COOH |
| Pr | 4-Me | H | Me | Me | (3-Cl)Ph | COOH |
| Pr | H | 7-Me | Bu | H | (3-Cl)Ph | COOH |
| Ph | 4-Cl | H | Cl | Cl | (3-Cl)Ph | COOH |
| Me | 4-Cl | H | Br | Br | (3-Cl)Ph | COOH |
| Ph | 4-Cl | H | Pr | Pr | (3-Cl)Ph | COOH |
| Et | 4-Me | H | Pr | H | (2-MePh | COOH |
| Ph | 4-Cl | H | Cl | Cl | (3-Br)Ph | COOH |
| Me | 4-Cl | H | Br | Br | (3-Br)Ph | COOH |
| Me | 4-Cl | H | Pr | Pr | (3-Br)Ph | COOH |
| Ph | 4-Cl | H | Me | Me | (3-NO₂)Ph | COOH |
| Me | H | H | Br | Br | (3-SMe)Ph | COOH |
| Ph | H | 7-Cl | Pr | Pr | (3-SMe)Ph | COOH |

-continued

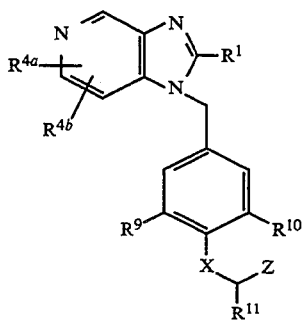

| R¹ | R⁴ᵃ | R⁴ᵇ | R⁹ | R¹⁰ | R¹¹ | Z |
|---|---|---|---|---|---|---|
| Ph | 4-Cl | H | Pr | Pr | (3-Cl)Ph | tetrazol-5-yl |
| Et | 4-Me | H | Pr | Pr | (3-Cl)Ph | CONHSO₂Me |
| Ph | 4-Cl | H | Pr | Pr | 2-Naphthyl | COOH |
| Ph | 4-Cl | H | Me | Me | 2-Naphthyl | COOH |
| Me | H | H | Br | Br | 2-Naphthyl | COOH |
| Ph | H | 7-Cl | Pr | Pr | 2-Naphthyl | COOH. |

5. The method as recited in claim 1, wherein the mammal is human.

6. The method of treating asthma as recited in claim 1, comprising a pharmaceutical composition of a therapeutically effective amount a compound of formula of claim 1 and a pharmaceutically acceptable carrier.

* * * * *